(12) United States Patent
Kim et al.

(10) Patent No.: US 11,447,480 B2
(45) Date of Patent: Sep. 20, 2022

(54) COMPOUND EXHIBITING ENTEROPEPTIDASE INHIBITORY ACTIVITY

(71) Applicant: LG CHEM, LTD., Seoul (KR)

(72) Inventors: Young Kwan Kim, Daejeon (KR); Ohhwan Kwon, Daejeon (KR); Heedong Park, Daejeon (KR); Junggyu Park, Daejeon (KR); Hwan Geun Choi, Seoul (KR); Jung Beom Son, Incheon (KR); Eunhwa Ko, Daegu (KR); So Young Kim, Daegu (KR); Seungyeon Lee, Daegu (KR); Seock Yong Kang, Seoul (KR); Yi Kyung Ko, Daegu (KR); Jin-Hee Park, Mokpo-si (KR)

(73) Assignee: LG CHEM, LTD., Seoul (KR)

( * ) Notice: Subject to any disclaimer, the term of this patent is extended or adjusted under 35 U.S.C. 154(b) by 0 days.

(21) Appl. No.: 17/054,084

(22) PCT Filed: May 8, 2019

(86) PCT No.: PCT/KR2019/005997
§ 371 (c)(1),
(2) Date: Nov. 9, 2020

(87) PCT Pub. No.: WO2019/216742
PCT Pub. Date: Nov. 14, 2019

(65) Prior Publication Data
US 2021/0284634 A1    Sep. 16, 2021

(30) Foreign Application Priority Data

May 9, 2018  (KR) .................. 10-2018-0053315
May 9, 2018  (KR) .................. 10-2018-0053316

(51) Int. Cl.
C07D 417/04    (2006.01)
C07D 277/56    (2006.01)
C07D 277/82    (2006.01)

(52) U.S. Cl.
CPC ......... C07D 417/04 (2013.01); C07D 277/56 (2013.01); C07D 277/82 (2013.01)

(58) Field of Classification Search
CPC ... C07D 417/04; C07D 277/56; C07D 277/82
See application file for complete search history.

(56) References Cited

U.S. PATENT DOCUMENTS

| | | | |
|---|---|---|---|
| 9,115,107 | B2 | 8/2015 | Konishi et al. |
| 9,346,821 | B2 | 5/2016 | Suzuki et al. |
| 2004/0259923 | A1 | 12/2004 | Inoue et al. |
| 2005/0065143 | A1 | 3/2005 | Chakka et al. |
| 2009/0105250 | A1* | 4/2009 | Sim ................ A61P 11/06 514/235.8 |
| 2010/0029690 | A1 | 2/2010 | Atobe et al. |

FOREIGN PATENT DOCUMENTS

| | | | |
|---|---|---|---|
| EP | 2206707 | A1 | 7/2010 |
| EP | 2511271 | A1 | 7/2010 |
| EP | 2316827 | A1 | 5/2011 |
| KR | 10-2006-0036107 | A | 4/2006 |
| KR | 10-2012-0030601 | A | 3/2012 |
| KR | 10-2016-0113299 | A | 9/2016 |
| RU | 2477281 | C2 | 3/2013 |
| WO | 1994-000434 | A1 | 1/1994 |
| WO | 2004-071440 | A2 | 8/2004 |
| WO | WO 2004/071440 | * | 8/2004 |
| WO | 2004-000806 | A1 | 12/2004 |
| WO | 2008-124393 | A1 | 10/2008 |
| WO | 2011-071048 | A1 | 6/2011 |
| WO | 2012-169579 | A1 | 12/2012 |
| WO | 2015-122187 | A1 | 8/2015 |
| WO | 2015-122188 | A1 | 8/2015 |
| WO | 2016-104630 | A1 | 6/2016 |

(Continued)

OTHER PUBLICATIONS

Extended European Search Report dated Feb. 25, 2021, of the corresponding European Patent Application No. 19800582.9, 14 pages.
Bueno, et al., "Design, synthesis and antimalarial evaluation of novel thiazole derivatives", Biorganic & Medicinal Chemistry Letters, vol. 26, No. 16, Jul. 5, 2016, pp. 3938-3944.
STN Registry Database Results: CAS Registry No. 2185871-05-8, Mar. 2018, 15 pages.
International Search Report issued for International Application No. PCT/KR2019/005997 dated Aug. 7, 2019, 6 pages.
STN express, RN 1787822-89-2 (Entered STN: Jun. 24, 2015), 1 page.
STN express, RN 884820-28-4 (Entered STN: May 18, 2006), 1 page.
STN express, RN 906254-06-6 (Entered STN: Sep. 10, 2006), RN 906225-41-0 (Entered STN: Sep. 10, 2006), RN 664350-47-4 (Entered STN: Mar. 18, 2004), 1 page.

*Primary Examiner* — Jared Barsky
(74) *Attorney, Agent, or Firm* — Rothwell, Figg, Ernst & Manbeck, P.C.

(57) ABSTRACT

The present invention relates to a novel compound exhibiting enteropeptidase-inhibiting activity, a pharmaceutically acceptable salt thereof, a pharmaceutical composition for preventing and treating metabolic diseases such as obesity, diabetes mellitus or hyperlipidemia, etc. comprising the compound or pharmaceutically acceptable salt, and a method for preventing or treating metabolic disease using the above novel compound. The compound of the present invention has excellent inhibitory activity against enteropeptidase, and thus is not absorbed into the body, but are excreted outside the body. However, since not only fat but also protein are discharged together, it has few side effects such as fat stools and acts only in the gastrointestinal tract, so it has few side effects such as depression, and is very useful as a therapeutic or prophylactic drug for various metabolic diseases such as obesity, diabetes mellitus, and hyperlipidemia.

11 Claims, No Drawings

(56) References Cited

FOREIGN PATENT DOCUMENTS

WO     2016-158788 A1    10/2016
WO     2018-071343 A1     4/2018

* cited by examiner

COMPOUND EXHIBITING ENTEROPEPTIDASE INHIBITORY ACTIVITY

CROSS-REFERENCE TO RELATED APPLICATION(S)

This application is a 35 U.S.C. 371 National Phase Entry Application from PCT/KR2019/005997 filed on May 8, 2019, designating the United States, which claims the benefit of Korean Patent Application Nos. 10-2018-0053315 and 10-2018-0053316 filed on May 9, 2018 with the Korean Intellectual Property Office, the disclosures of which are herein incorporated by reference in their entirety.

TECHNICAL FIELD

The present invention relates to a novel compound exhibiting enteropeptidase-inhibiting activity, a pharmaceutically acceptable salt thereof and a pharmaceutical composition for preventing and treating metabolic diseases such as obesity, diabetes mellitus or hyperlipidemia, etc. comprising the compound or pharmaceutically acceptable salt.

BACKGROUND ART

Enteropeptidase is a serine protease that converts trypsinogen, which is secreted from the pancreas after a meal, to trypsin. Trypsin activated by enteropeptidase then activates protease precursors such as chymotrypsinogen, procarboxypeptidase and proelastase. These active forms of proteases degrade dietary proteins into amino acid units, and the resulting amino acids are absorbed from the small intestine. Thus, it is reported that enteropeptidase inhibitors are capable of suppressing protein degradation and absorption, and are useful as a therapeutic drug for obesity.

Among conventional oral obesity therapeutic drugs, Xenical has a mechanism of action for suppressing the action of lipolytic enzymes in a gastrointestinal tract. Due to such an action, fat is not absorbed into the body and is extracted outside the body. At this time, there is a side effect that the patient has a fat stool movement without knowing it beforehand.

On the other hand, drugs such as Belviq, Contrave, and Qsymia are used as anti-obesity drugs through appetite-inhibiting action in the brain, but they have serious adverse effects such as depression and suicidal impulses.

In this regard, U.S. Pat. No. 9,346,821 discloses a heterocyclic carboxylic acid ester derivative showing serine protease-inhibiting activity for the treatment or prevention of obesity, and Korean Unexamined Patent Publication No. 10-2016-0113299 discloses a fused heterocyclic compound having an enteropeptidase-inhibiting action and its use as a medicament for treatment or prophylaxis of obesity and diabetes mellitus, etc.

Under these circumstances, there is a continuing need to develop a compound that still exhibits excellent enteropeptidase-inhibiting activity, and is useful for the prevention or treatment of metabolic diseases such as obesity, diabetes mellitus or hyperlipidemia, etc.

BRIEF SUMMARY OF THE INVENTION

Therefore, the present invention is to provide a novel compound having enteropeptidase-inhibiting activity, and useful for the prevention and treatment of metabolic diseases such as obesity, diabetes mellitus or hyperlipidemia, etc., or a pharmaceutically acceptable salt thereof, a pharmaceutical composition comprising the same and a method for preventing or treating metabolic disease using the novel compound or pharmaceutically acceptable salt thereof.

A compound having the following Chemical Formula 1, an optical isomer thereof, or a pharmaceutically acceptable salt thereof is provided herein. The compound of Chemical Formula 1 exhibits excellent enteropeptidase-inhibiting activity, and thus is useful for the treatment of various metabolic diseases such as obesity, diabetes mellitus, and hyperlipidemia, etc.

[Chemical Formula 1]

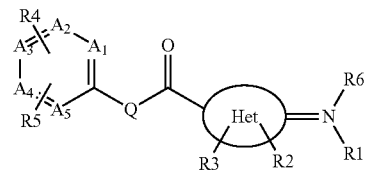

wherein,

Het is a 4- to 10-membered mono- or di-heterocyclic group having one or two heteroatoms selected from the group consisting of N, O and S;

a dotted line represents the presence or absence of a bond, A1, A2, A3, A4 and A5 are each independently C or N;

Q is O or N;

R1, and R6 are each independently H, or an unsubstituted or substituted alkyl, or R1 and R6 together with the nitrogen atom to which they are attached form an unsubstituted or substituted a 5- to 7-membered heterocyclic ring;

R2 is hydrogen or an unsubstituted or substituted alkyl;

R3 and R4 are each independently H, halo or an unsubstituted or substituted alkyl; and R5 is amidine, guanidine, amide or an unsubstituted or substituted alkylamine.

Regarding the "presence or absence of a bond" in the Chemical Formula 1, when the bond is present, it means that a bond between a carbon atom bonded to an exocyclic nitrogen atom (i.e., N of NR1R6) among carbon atoms of Het, and the exocyclic nitrogen atom forms a double bond (wherein the exocyclic nitrogen atom bonded to a carbon atom in the Het group connected to the NR1R6 becomes an imino group as a substituent for the Het, and R6 is not present).

Also, preferably, the Het is a 5- to 9-membered mono- or di-heterocyclic group having one or two heteroatoms selected from the group consisting of N and S, and more preferably, it may be thiazole or benzothiazole.

Further, preferably, the substituent may be one to three selected from the group consisting of —$(CR^a_2)_nR^b$, —C(O)OR$^a$, —$(CH_2)_n$—C(O)OR$^a$, —$(CH_2)_n$—C(O)NR$^a$R$^b$, —C(O)NR$^a$R$^b$, and —NR$^a$C(O)R$^b$, where R$^a$ and R$^b$ are each independently hydrogen, halo, —C(O)OR$^c$, —C(O)NR$^c$R$^d$, C1-C4 alkyl or phenyl, n is an integer from 1 to 4, the C1-C4 alkyl or phenyl is unsubstituted or substituted with one or two —C(O)OR$^c$, C1-C4 alkoxy, and Rc may be hydrogen, C1-C4 alkyl or benzyl.

ADVANTAGEOUS EFFECTS

The novel compound according to the present invention reduces the digestive ability of proteins, lipids and carbohydrates through excellent enteropeptidase-inhibiting activity, and are useful as a therapeutic or prophylactic drug for various metabolic diseases such as obesity or diabetes mellitus and hyperlipidemia.

DETAILED DESCRIPTION OF THE EMBODIMENTS

The present invention is described in more detail in the following

The definition of each substituent used in the present specification is described in detail in the following. Unless otherwise specified, each substituent has the following definition.

In the present specification, examples of the "halo" include fluoro, chloro, bromo and iodo.

In the present specification, "alkyl" means a linear or branched aliphatic saturated hydrocarbon group. Preferably, it may be an alkyl having 1 to 6 carbons, more preferably alkyl having 1 to 4 carbons. Examples of such alkyl include methyl, ethyl, propyl, isopropyl, butyl, isobutyl, sec-butyl, tert-butyl, pentyl, isopentyl, neopentyl, 1-ethylpropyl, hexyl, isohexyl, 1,1-dimethyl butyl, 2,2-dimethylbutyl, 3,3-dimethylbutyl and 2-ethylbutyl.

In the present specification, "heterocycle" means an aromatic or non-aromatic ring containing a heteroatom selected from nitrogen atoms, sulfur atoms and oxygen atoms other than carbon atoms as ring constituent atoms, and it includes preferably 4- to 10-membered, more preferably 5- to 9-membered aromatic or non-aromatic ring containing 1 to 4 of the heteroatoms. Examples of such aromatic ring include thienyl, furyl, pyrrolyl, imidazolyl, pyrazolyl, thiazolyl, isothiazolyl, oxazolyl, isoxazolyl, pyridyl, pyrazinyl, pyrimidinyl, pyridazinyl, 1,2,4-oxadiazolyl, 1,3,4-oxadiazolyl, 1,2,4-thiadiazolyl, 1,3,4-thiadiazolyl, triazolyl, tetrazolyl, triazinyl and benzothiazolyl. Further, examples of such non-aromatic ring include tetrahydrothienyl, tetrahydrofuranyl, pyrrolinyl, pyrrolidinyl, imidazolinyl, imidazolidinyl, oxazolinyl, oxazolidinyl, pyrazolinyl, pyrazolidinyl, thiazolinyl, thiazolidinyl, tetrahydroisothiazolyl, tetrahydrooxazolyl, tetrahydroisoxazolyl, piperidinyl, piperazinyl, tetrahydropyridinyl, dihydropyridinyl, dihydrothiopyranyl, tetrahydropyrimidinyl, tetrahydropyridazinyl, dihydropyranyl, tetrahydropyranyl, tetrahydrothiopyranyl, morpholinyl, thiomorpholinyl, azepanyl, diazepanyl and azepinyl.

In the present specification, examples of the "substituent" include a halogen atom, a cyano group, a nitro group, an unsubstituted or substituted amino group including an unsubstituted or substituted alkyl group and an unsubstituted or substituted carboxyl group, an unsubstituted or substituted hydrocarbon group, an unsubstituted or substituted heterocyclic group, an acyl group, an unsubstituted or substituted amino group, an unsubstituted or substituted carbamoyl group, an unsubstituted or substituted thiocarbamoyl group, an unsubstituted or substituted sulfamoyl group, an unsubstituted or substituted hydroxy group, an unsubstituted or substituted sulfanyl (SH) group and an unsubstituted or substituted silyl group.

In a preferred embodiment, the compound of the Chemical Formula 1 may be a compound of the following Chemical Formula 1a.

[Chemical Formula 1a]

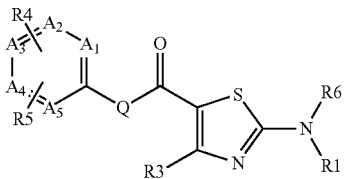

wherein,
A1, A2, A3, A4 and A5 are each independently C or N;
Q is O or N;
R1 and R6 are each independently H, or an unsubstituted or substituted alkyl, or R1 and R6 together with the nitrogen atom to which they are attached form an unsubstituted or substituted 5- to 7-membered heterocyclic ring;
R3 and R4 are each independently H, halo or an unsubstituted or substituted alkyl; and
R5 is amidine, guanidine, amide, or an unsubstituted or substituted alkylamine.

In a preferred embodiment, in the Chemical Formula 1a, the A1, A2, A3, A4 and A5 may be each independently C.

The R1 and R6 may be each independently H or an unsubstituted or substituted C1-C6 alkyl, more preferably H or C1-C3 alkyl.

In addition, R1 and R6 may also, together with the nitrogen atom to which they are attached, form an unsubstituted or substituted 5- or 6-membered heterocyclic ring, more preferably pyrrolidinyl or piperidinyl.

Further, R3 and R4 may be each independently H, F, Cl, Br, I, or an unsubstituted or substituted C1-C6 alkyl, and more preferably, it may be H, F or an unsubstituted or substituted C1-C3 alkyl.

Further, R5 may be amidine, guanidine, amide, or an unsubstituted or substituted C1-C4 alkylamine.

Further, the substituent may be one or more, preferably one to three, selected from the group consisting of —(CR$^a_2$)$_n$—R$^b$, —C(O)OR$^a$, —(CH$_2$)$_n$—C(O)OR$^a$, —(CH$_2$)$_n$—C(O)NR$^a$R$^b$, —C(O)NR$^a$R$^b$, and —NR$^a$C(O)R$^b$, where R$^a$ and R$^b$ may be each independently hydrogen, halo, —C(O)OR$^c$, —C(O)NR$^c$R$^d$, C1-C4 alkyl or phenyl, n may be an integer from 1 to 4, the C1-C4 alkyl or phenyl may be unsubstituted or substituted with one or two —C(O)OR$^c$, C1-C4 alkoxy, and
R$^c$ may be hydrogen, C1-C4 alkyl or benzyl.

In another preferred embodiment, the compound of Chemical Formula 1 may be a compound of the following Chemical Formula 1b:

[Chemical Formula 1b]

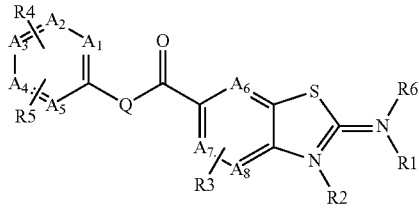

wherein,
a dotted line represents the presence or absence of a bond,
A1, A2, A3, A4, A5, A6, A7 and A8 are each independently C or N;
Q is O or N;

R1 and R6 are each independently H, or an unsubstituted or substituted alkyl, or R1 and R6 together with the nitrogen atom to which they are attached form an unsubstituted or substituted 5- to 7-membered heterocyclic ring;

R2 is an unsubstituted or substituted alkyl;

R3 and R4 are each independently H, halo or an unsubstituted or substituted alkyl; and R5 is amidine, guanidine, amide, or an unsubstituted or substituted alkylamine.

The dotted line in the compound of the Chemical Formula 1b represents the presence or absence of a bond, and when the bond is present, a double bond forms between S and N in 5-membered heterocycle consisting of S and N combined with benzene ring and a nitrogen atom in the heterocycle (wherein the exocyclic nitrogen atom bound to the carbon atom (i.e., N of NR1R6) becomes an amino group as a substituent for the 5-membered hetero ring, and R2 is not present), or a double bond forms between a carbon atom between S and N in 5-membered heterocycle and an exocyclic nitrogen atom, and thus, the exocyclic nitrogen atom becomes an imino group and R6 is not present.

Preferably, the Chemical Formula 1b according to the present invention may be a compound of the following Chemical Formula 1b-1:

[Chemical Formula 1b-1]

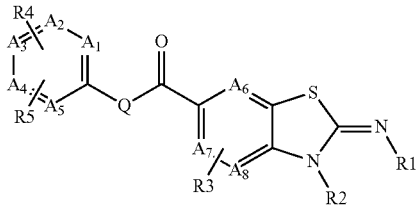

wherein,

A1, A2, A3, A4, A5, A6, A7 and A8 are each independently C or N;

Q is O or N;

R1 and R6 are each independently H or an unsubstituted or substituted alkyl;

R1 and R2 are each independently H or an unsubstituted or substituted alkyl;

R3 and R4 are each independently H, halo or an unsubstituted or substituted alkyl; and R5 is amidine, guanidine, amide, or an unsubstituted or substituted alkylamine.

Further, preferably, the Chemical Formula 1b according to the present invention may be a compound of the following Chemical Formula 1b-2:

[Chemical Formula 1b-2]

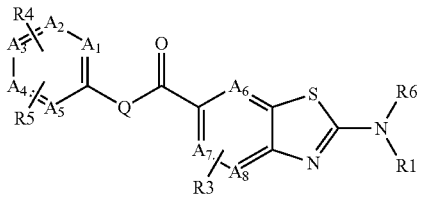

wherein,

A1, A2, A3, A4, A5, A6, A7 and A8 are each independently C or N;

Q is O or N;

R1, and R6 are each independently H or an unsubstituted or substituted alkyl, or R1 and R6 together with the nitrogen atom to which they are attached form an unsubstituted or substituted 5- to 7-membered heterocyclic ring;

R3 and R4 are each independently H, halo or an unsubstituted or substituted alkyl; and R5 is amidine, guanidine, amide, or an unsubstituted or substituted alkylamine, In a preferred embodiment, in the Chemical Formulas 1, 1b-1 and 1b-2, the A1, A2, A3, A4, A5, A6, A7 and A8 may be each independently C.

The R1 and R6 may be each independently H or an unsubstituted or substituted C1-C6 alkyl, and more preferably H or C1-C3 alkyl.

Further, R1 and R6 may, together with the nitrogen atom to which they are attached, form an unsubstituted or substituted 6-membered heterocyclic ring, more preferably piperidinyl.

Further, R2 may be H or an unsubstituted or substituted C1-C6 alkyl, and more preferably H or an unsubstituted or substituted C1-C3 alkyl.

Further, R3 and R4 may each independently be H, F, Cl, Br, I, or an unsubstituted or substituted C1-C6 alkyl, more preferably H, F or an unsubstituted or substituted C1-C3 alkyl.

Further, R5 may be amidine, guanidine, amide or an unsubstituted or substituted C1-C4 alkylamine.

Further, the substituent may be C1-C4 alkyl, —C(O)OR', —C(O)NR'R" or —NR'C(O)R", where R' and R" may be each independently hydrogen, halo, C1-C4 alkyl or phenyl, and the number of these substituents may be one or more, preferably one to three.

Representative compounds of the Chemical Formula 1 according to the present invention may include the following compounds, but are not limited to thereto.

1] 3-((5-((4-carbamimidoyl-2-fluorophenoxy)carbonyl)thiazol-2-yl)(ethyl)amino)propanoic acid;

2] 1-(5-((4-carbamimidoylphenoxy)carbonyl)thiazol-2-yl)piperidine-4-carboxylic acid;

3] 4-carbamimidoylphenyl 2-(4-(methoxycarbonyl)piperidin-1-yl)thiazole-5-carboxylate;

4] 4-carbamimidoyl-2-fluorophenyl 2-(4-(methoxycarbonyl)piperidin-1-yl)thiazole-5-carboxylate;

5] 4-guanidinophenyl 2-(4-(methoxycarbonyl)piperidin-1-yl)thiazole-5-carboxylate;

6] 1-(5-((4-guanidinophenoxy)carbonyl)thiazol-2-yl)piperidine-4-carboxylic acid;

7] 1-(5-((4-carbamimidoyl-2-fluorophenoxy)carbonyl)thiazol-2-yl)piperidine-4-carboxylic acid;

8] 4-carbamimidoylphenyl 2-((3-methoxy-3-oxopropyl)(methyl)amino)thiazole-5-carboxylate;

9] 3-((5-((4-carbamimidoyl)phenoxy)carbonyl)thiazol-2-yl)(methyl)amino)propanoic acid;

10] 4-carbamimidoylphenyl 2-((3-methoxy-3-oxopropyl)amino)thiazole-5-carboxylate;

11] 4-carbamimidoylphenyl 2-((4-methoxy-4-oxobutyl)(methyl)amino)thiazole-5-carboxylate;

12] 4-carbamimidoylphenyl 2-(ethyl(3-methoxy-3-oxopropyl)amino)thiazole-5-carboxylate;

13] 3-((5-((4-carbamimidoyl)phenoxy)carbonyl)thiazol-2-yl)amino)propanoic acid;

14] 3-((5-((4-carbamimidoyl)phenoxy)carbonyl)thiazol-2-yl)(ethyl)amino)propanoic acid;

15] 4-((5-((4-carbamimidoyl)phenoxy)carbonyl)thiazol-2-yl)(methyl)amino)butanoic acid;
16] 4-carbamimidoylphenyl 2-(3-(methoxycarbonyl)pyrrolidin-1-yl)thiazole-5-carboxylate;
17] 1-(5-((4-carbamimidoylphenoxy)carbonyl)thiazol-2-yl)pyrrolidine-3-carboxylic acid;
18] 4-carbamimidoylphenyl 2-((3-methoxy-2,2-dimethyl-3-oxopropyl)(methyl)amino)thiazole-5-carboxylate;
19] 3-((5-((4-carbamimidoylphenoxy)carbonyl)thiazol-2-yl)(methyl)amino)-2,2-dimethylpropanoic acid;
20] 4-carbamimidoyl-2-fluorophenyl 2-(ethyl(3-methoxy-3-oxopropyl)amino) thiazole-5-carboxylate;
21] 4-carbamimidoyl-2-fluorophenyl 2-((4-methoxy-4-oxobutyl)(methyl)amino)thiazole-5-carboxylate;
22] 4-((5-((4-carbamimidoyl-2-fluorophenoxy)carbonyl)thiazol-2-yl)(methyl)amino)butanoic acid;
23] methyl 1-(5-((4-guanidinophenyl)carbamoyl)thiazol-2-yl)piperidine-4-carboxylate;
24] 4-carbamimidoylphenyl 2-((3-methoxy-2,2-dimethyl-3-oxopropyl)amino)thiazole-5-carboxylate;
25] (1-(5-((4-carbamimidoyl) phenoxy)carbonyl)thiazol-2-yl)piperidine-4-carbonyl)-L-aspartic acid;
26] (1-(5-((4-carbamimidoyl-2-fluorophenoxy)carbonyl)thiazol-2-yl)piperidine-4-carbonyl)-L-aspartate;
27] 4-carbamimidoylphenyl 2-(4-(phenylcarbamoyl)piperidin-1-yl)thiazole-5-carboxylate;
28] 4-carbamimidoylphenyl 2-(4-benzamidopiperidin-1-yl)thiazole-5-carboxylate;
29] 4-carbamimidoylphenyl 2-(4-((2-methoxy-2-oxoethyl)carbamoyl)piperidin-1-yl)thiazole-5-carboxylate;
30] 4-carbamimidoylphenyl 2-(4-((3-methoxy-3-oxopropyl)carbamoyl)piperidin-1-yl)thiazole-5-carboxylate;
31] 4-carbamimidoylphenyl 2-(4-((4-methoxy-4-oxobutyl)(methyl)carbamoyl) piperidin-1-yl)thiazole-5-carboxylate;
32] 4-carbamimidoylphenyl 2-(4-((3-methoxy-2,2-dimethyl-3-oxopropyl)carbamoyl)piperidin-1-yl)thiazole-5-carboxylate;
33] (1-(5-((4-carbamimidoylphenoxy)carbonyl)thiazol-2-yl)piperidine-4-carbonyl)glycine;
34] 3-(1-(5-((4-carbamimidoylphenoxy)carbonyl)thiazol-2-yl)piperidine-4-carboxamido)propanoic acid;
35] 4-(1-(5-((4-carbamimidoylphenoxy)carbonyl)thiazol-2-yl)-N-methylpiperidine-4-carboxamido)butanoic acid;
36] 3-(1-(5-((4-carbamimidoylphenoxy)carbonyl)thiazol-2-yl)piperidine-4-carboxamido)-2,2-dimethyl propanoic acid;
37] 4-carbamimidoyl-2-fluorophenyl 2-(4-((2-methoxy-2-oxoethyl)carbamoyl)piperidin-1-yl)thiazole-5-carboxylate;
38] 4-carbamimidoyl-2-fluorophenyl 2-(4-((3-methoxy-3-oxopropyl)carbamoyl)piperidin-1-yl)thiazole-5-carboxylate;
39] 4-carbamimidoyl-2-fluorophenyl 2-(4-((3-methoxy-2,2-dimethyl-3-oxopropyl) carbamoyl)piperidin-1-yl)thiazole-5-carboxylate;
40] 4-carbamimidoylphenyl 2-(4-((4-methoxyphenyl)carbamoyl)piperidin-1-yl)thiazole-5-carboxylate;
41] 4-carbamimidoyl-2-fluorophenyl 2-(4-((4-methoxy-4-oxobutyl)(methyl)carbamoyl) piperidin-1-yl)thiazole-5-carboxylate;
42] (1-(5-((4-carbamimidoyl-2-fluorophenoxy)carbonyl)thiazol-2-yl)piperidine-4-carbonyl)glycine;
43] 3-(1-(5-((4-carbamimidoyl-2-fluorophenoxy)carbonyl)thiazol-2-yl)piperidine-4-carboxamido)propanoic acid;
44] 4-(1-(5-((4-carbamimidoyl-2-fluorophenoxy)carbonyl)thiazol-2-yl)-N-methylpiperidine-4-carboxamido)butanoic acid;
45] 3-(1-(5-((4-carbamimidoyl-2-fluorophenoxy)carbonyl)thiazol-2-yl)piperidine-4-carboxamido)-2, 2-dimethylpropanoic acid;
46] di-tert-butyl(3-((5-((4-carbamimidoyl-2-fluorophenoxy)carbonyl)thiazol-2-yl)(ethyl)amino)propanoyl)-L-aspartate;
47] (3-((5-((4-carbamimidoyl-2-fluorophenoxy)carbonyl)thiazol-2-yl)(ethyl)amino)propanoyl)-L-aspartic acid;
48] di-tert-butyl (3-((5-((4-carbamimidoyl)-2-fluorophenoxy)carbonyl)thiazol-2-yl)(ethyl)amino)propanoyl)-D-glutamate;
49] (3-((5-((4-carbamimidoyl-2-fluorophenoxy)carbonyl)thiazol-2-yl)(ethyl)amino)propanoyl)-D-glutamic acid;
50] 4-carbamimidoyl-2-fluorophenyl 2-(ethyl(3-((4-(methoxycarbonyl)phenyl)amino)-3-oxopropyl)amino)thiazole-5-carboxylate;
51] 4-carbamimidoyl-2-fluorophenyl 2-(ethyl(3-((3-(methoxycarbonyl)phenyl)amino)-3-oxopropyl) amino)thiazole-5-carboxylate;
52] 4-carbamimidoyl-2-fluorophenyl 2-((3-((4-(tert-butoxycarbonyl)phenyl)amino)-3-oxopropyl) (ethyl)amino)thiazole-5-carboxylate;
53] 4-carbamimidoyl-2-fluorophenyl 2-((tert-butoxycarbonyl)phenyl)amino)-3-oxopropyl) (ethyl)amino)thiazole-5-carboxylate;
54] 3-(3-((5-((4-carbamimidoyl-2-fluorophenoxy)carbonyl)thiazol-2-yl)(ethyl)amino)propanamido)benzoic acid;
55] 4-(3-((5-((4-carbamimidoyl-2-fluorophenoxy)carbonyl)thiazol-2-yl)(ethyl)amino)propanamido)benzoic acid;
56] 3-((6-((4-carbamimidoyl-2-fluorophenoxy)carbonyl)benzo[d]thiazol-2-yl)amino)-2,2-dimethylpropanoic acid;
57] 4-carbamimidoylphenyl 2-(4-(methoxycarbonyl)piperidin-1-yl)benzo[d]thiazole-6-carboxylate;
58] 1-(6-((4-carbamimidoylphenoxy)carbonyl)benzo[d]thiazol-2-yl)piperidine-4-carboxylic acid;
59] 4-carbamimidoylphenyl 2-((3-methoxy-3-oxopropyl)amino)benzo[d]thiazole-6-carboxylate;
60] 4-carbamimidoylphenyl 2-((3-methoxy-3-oxopropyl)(methyl)amino)benzo[d]thiazole-6-carboxylate;
61] 4-carbamimidoylphenyl 2-(ethyl(3-methoxy-3-oxopropyl)amino)benzo[d]thiazole-6-carboxylate;
62] 3-((6-((4-carbamimidoylphenoxy)carbonyl)benzo[d]thiazol-2-yl)(methyl)amino)propanoic acid;
63] 4-carbamimidoylphenyl 2-((4-methoxy-4-oxobutyl)(methyl)amino)benzo[d]thiazole-6-carboxylate;
64] 4-((6-((4-carbamimidoylphenoxy)carbonyl)benzo[d]thiazol-2-yl)(methyl)amino)butanoic acid;
65] 3-((6-((4-carbamimidoylphenoxy)carbonyl)benzo[d]thiazol-2-yl)amino)propanoic acid;
66] 3-((6-((4-carbamimidoylphenoxy)carbonyl)benzo[d]thiazol-2-yl)(ethyl)amino)propanoic acid;
67] 4-carbamimidoylphenyl 2-((3-methoxy-2,2-dimethyl-3-oxopropyl)amino)benzo[d]thiazole-6-carboxylate;
68] 4-carbamimidoylphenyl 2-((3-methoxy-2,2-dimethyl-3-oxopropyl)(methyl)amino)benzo[d]thiazole-6-carboxylate;
69] 4-carbamimidoylphenyl 2-(ethyl(3-methoxy-2,2-dimethyl-3-oxopropyl)amino)benzo[d]thiazole-6-carboxylate;
70] 4-carbamimidoyl-2-fluorophenyl 2-(ethyl(3-methoxy-2, 2-dimethyl-3-oxopropyl)amino)benzo[d]thiazole-6-carboxylate;
71] 4-carbamimidoyl-2-fluorophenyl 2-((4-methoxy-4-oxobutyl)(methyl)amino)benzo[d]thiazole-6-carboxylate;

72] 4-carbamimidoyl-2-fluorophenyl 2-((3-methoxy-3-oxopropyl)(methyl)amino)benzo[d]thiazole-6-carboxylate;
73] 3-((6-((4-carbamimidoylphenoxy)carbonyl)benzo[d]thiazol-2-yl)amino)-2,2-dimethylpropanoic acid;
74] 3-((6-((4-carbamimidoylphenoxy)carbonyl)benzo[d]thiazol-2-yl)(ethyl) amino)-2,2-dimethylpropanoic acid;
75] 3-((6-((4-carbamimidoyl-2-fluorophenoxy)carbonyl) benzo[d]thiazol-2-yl)(ethyl)amino)-2,2-dimethyl propanoic acid;
76] 4-((6-((4-carbamimidoyl-2-fluorophenoxy)carbonyl) benzo[d]thiazol-2-yl)(methyl)amino)butanoic acid;
77] 3-((6-((4-carbamimidoyl-2-fluorophenoxy)carbonyl) benzo[d]thiazol-2-yl)(methyl) amino)propanoic acid;
78] 4-carbamimidoyl-2-fluorophenyl 2-(4-(methoxycarbonyl piperidin-1-yl)benzo[d]thiazole-6-carboxylate;
79] 1-(6-((4-carbamimidoyl-2-fluorophenoxy)carbonyl) benzo[d]thiazol-2-yl)piperidine-4-carboxylic acid;
80] 4-carbamimidoylphenyl 2-(4-(phenylcarbamoyl)piperidin-1-yl)benzo[d]thiazole-6-carboxylate;
81] 4-carbamimidoyl-2-fluorophenyl 2-(4-(phenylcarbamoyl)piperidin-1-yl)benzo[d]thiazole-6-carboxylate;
82] 4-carbamimidoyl-2-fluorophenyl 2-(4-benzoamidopiperidin-1-yl)benzo[d]thiazole-6-carboxylate;
83] 4-carbamimidoylphenyl 2-(4-benzoamidopiperidin-1-yl)benzo[d]thiazole-6-carboxylate;
84] 4-carbamimidoyl-2-fluorophenyl 2-(ethyl(3-methoxy-3-oxopropyl)amino)benzo[d]thiazole-6-carboxylate;
85] 3-((6-((4-carbamimidoyl-2-fluorophenoxy)carbonyl) benzo[d]thiazol-2-yl)(ethyl)amino)propanoic acid;
86] 3-((6-((4-carbamimidoylphenoxy)carbonyl)benzo[d]thiazol-2-yl)(methyl)amino)-2,2-dimethylpropanoic acid;
87] 4-carbamimidoyl-2-fluorophenyl (Z)-3-ethyl-2-((3-methoxy-2,2-dimethyl-3-oxopropyl)imino)-2,3-dihydrobenzo[d]thiazole-6-carboxylate; and
88] (Z)-3-((6-((4-carbamimidoyl-2-fluorophenoxy)carbonyl)-3-ethylbenzo[d]thiazole-2(3H)-ylidine)amino)-2,2-dimethylpropanoic acid.

Meanwhile, the novel compounds according to the one embodiment may have an asymmetric carbon center and may exist as racemates or individual optical isomers. It goes without saying that any form of isomers, including these optical isomers, also fall within the category of the compound of one embodiment. As used herein, the term "isomer" may collectively refer to different compounds having the same molecular formula, and the "optical isomer" may refer to any stereoisomer that may exist for a compound of one embodiment, including the same geometric isomers.

It is understood that in the compound of Chemical Formula 1 according to one embodiment, each substituent may be attached to a chiral center of carbon atoms. Any asymmetric carbon atom on the compound according to the one embodiment may be present in any form of (R)-, (S)- or (R,S)-configuration. Suitably, the compound may be present in (R)- or (S)-configuration. Further, the compound according to one embodiment may take the form of any possible isomer or a mixture of possible isomers, for example, a pure geometrical isomer, a diastereomer, an enantiomer, a racemate, or a mixture thereof. In addition, when the compound according to one embodiment has a double bond, substituents attached to the double bond may take E or Z configuration. Moreover, when the compound of one embodiment contains a bi-substituted cycloalkyl, each substituent on the cycloalkyl moiety may take cis- or trans-configuration.

Meanwhile, the term "pharmaceutically acceptable salt" as used herein refers to any salt which possesses the same biological activity and properties of the compound of Chemical Formula 1 according to one embodiment and which is preferable in terms of pharmaceutical, biological or other characteristics. Non-limiting examples of the salt include inorganic or organic base addition salts or acid addition salts of the compound of Chemical Formula 1. Examples of the organic acid applicable to the formation of an acid addition salt include acetic acid, propionic acid, glycolic acid, pyrubic acid, oxalic acid, maleic acid, malonic acid, succinic acid, furmaric acid, tartaric acid, citric acid, benzoic acid, cinnamic acid, mandelic acid, methanesulfonic acid, ethanesulfonic acid, p-toluene sulfonic acid, and salicylic acid. Examples of the inorganic acids may include hydrochloric acid, hydrobromic acid, sulfonic acid, nitric acid, phosphoric acid, and the like.

The pharmaceutically acceptable salt of the compound according to the above-mentioned one embodiment may be synthesized by a typical chemical method from either a compound in the form of a free base, or an alkaline or acidic residue derived therefrom. Further, a second pharmaceutically acceptable salt may be synthesized from a first pharmaceutically acceptable salt. As specific examples, a compound in a free base form may be reacted with a stoichiometric amount of a suitable acid to give an acid addition salt of the compound of one embodiment. In this regard, the reaction may be carried out in water, an organic solvent or a mixture thereof, for example, in a non-aqueous medium such as ether, ethyl acetate, ethanol, isopropanol or acetonitrile. Furthermore, other pharmaceutically acceptable salts may be obtained using typical reactions obvious to those skilled in the art.

The compound of the Chemical Formula 1 of the present invention exhibits an inhibitory activity against enteropeptidase, and thus has an activity of effectively inhibiting protein digestive enzymes as well as fat in the gastrointestinal tract. Food ingested is not absorbed into the body but is excreted outside the body. However, since protein as well as fat is excreted together, there are few side effects such as fatty stools. Moreover, since it acts only in the gastrointestinal tract, it is characterized by not having side effects such as depression.

Meanwhile, according to another embodiment of the present invention, a pharmaceutical composition comprising the compound of Chemical Formula 1, an isomer thereof, or a pharmaceutically acceptable salt thereof as an active ingredient, and exhibiting enteropeptidase-inhibiting activity is provided. Such pharmaceutical composition exhibits excellent enteropeptidase-inhibiting activity, and thus can be suitably used for the prevention or treatment of any disease associated with enteropeptidase enzyme activity, for example, metabolic diseases such as obesity and diabetes. Specifically, the compound of the present invention, or a pharmaceutically acceptable salt thereof can be used as a drug for the prophylaxis or treatment of obesity based on symptomatic obesity or simple obesity, disease states or diseases associated with obesity, eating disorder, diabetes mellitus (e.g., type 1 diabetes mellitus, type 2 diabetes mellitus, gestational diabetes mellitus, obese diabetes mellitus), hyperlipidemia (e.g., hypertriglyceridemia, hypercholesterolemia, high LDL-cholesterolemia, low HDL-cholesterolemia, postprandial hyperlipemia), hypertension, cardiac failure, diabetic complications [e.g., neuropathy, nephropathy, retinopathy, diabetic cardiomyopathy, cataract, macroangiopathy, osteopenia, hyperosmolar diabetic coma, infectious disease (e.g., respiratory infection, urinary tract infection, gastrointestinal infection, dermal soft tissue infections, inferior limb infection), diabetic gangrene, xerostomia, hypacusis, cerebrovascular disorder, peripheral blood circulation disorder], metabolic syndrome (disease states having 3 or more selected from hypertriglycerid(TG)emia, low HDL cholesterol(HDL-C)emia, hypertension, abdominal obesity and impaired glucose tolerance), sarcopenia, reflux esophagitis and the like.

Such pharmaceutical compositions can be used in the form of conventional pharmaceutical preparations. That is, the pharmaceutical composition may be administered in various formulations including an oral formulation and a parenteral formulation at the time of actual clinical administration, and it may be suitably administered in an oral administration. In addition, production is made by further including diluents or excipients such as conventional fillers, extenders, binding agents, wetting agents, disintegrating agents, or surfactants depending on the preparation.

The solid preparation for oral administration may include a tablet, a pill, a powder preparation, a granule, a capsule or the like, and such solid preparation may be provided by mixing an active ingredient with starch, calcium carbonate, sucrose, lactose, or gelatin, and the like. Further, in addition to the excipients, lubricants such as magnesium stearate or talc may be used. And, the liquid preparation for oral administration may include a suspension, a solution preparation for internal use, an emulsion, a syrup preparation, or the like. The liquid preparation for oral administration may include various kinds of vehicles such as moisturizing agent, sweetening agent, aromatic agent, or preservatives in addition to water or liquid paraffin as a commonly used simple diluent. Additionally, a preparation for parenteral administration may include a sterilized aqueous solution, a non-soluble agent, a suspension agent, an emulsion, a freeze-drying agent, a suppository agent, and the like. Such a preparation for parenteral administration may include a water insoluble solvent, and as a suspending solvent, propylene glycol, polyethylene glycol, or vegetable oil such as olive oil, and injectable ester such as ethylolate can be used. As a base for a suppository, witepsol, macrogol, Tween 61, cacao butter, laurin butter, glycerol, gelatin, or the like can be used.

According to another embodiment of the present invention, there is provided a method for inhibiting enteropeptidase, or a method for preventing or treating metabolic diseases, the method comprising the step of administrating a compound of the Chemical Formula 1, an isomer thereof, or a pharmaceutically acceptable salt thereof in a pharmaceutically effective amount in the form of the above-mentioned pharmaceutical composition. As used herein, the term "pharmaceutically effective amount" refers to an amount sufficient to treat diseases at a reasonable benefit/risk ratio applicable to any medical treatment. An effective dose level may be determined depending on a variety of factors comprising patient's health condition, type of diseases, severity, drug activity, drug sensitivity, administration method, administration time, administration route, excretion rate, the duration of treatment, combination or co-administered drugs, and other factors well known in the medical field. The pharmaceutical composition of the present invention comprising a compound of the Chemical Formula 1, an isomer thereof, or a pharmaceutically acceptable salts thereof may be administered as an individual therapeutic agent or in combination with other therapeutic agents, and may be administered sequentially or simultaneously with conventional therapeutic agents. The composition can be administered at single or multiple times. It important to administer the composition in the minimum possible amount sufficient to obtain the greatest therapeutic effect without side effects, in consideration of all the above-described factors, which can be easily determined by those skilled in the art. For example, since the dosage can be increased or decreased according to routes of administration, severity of diseases, sex, body weight, age and the like, the dosage does not limit the scope of the present invention in any way. The preferred dosage of the compound of the present invention depends on the patient's condition and body weight, the severity of disease, the type of drug, the route and duration of administration, but can be appropriately selected by those skilled in the art. Administration can be performed can be once daily or in divided doses via the oral or parenteral routes.

In addition, when the compound of the Chemical Formula 1 of the present invention contains a thiazole ring, it can be prepared by the preparation method of the following Reaction Scheme 1.

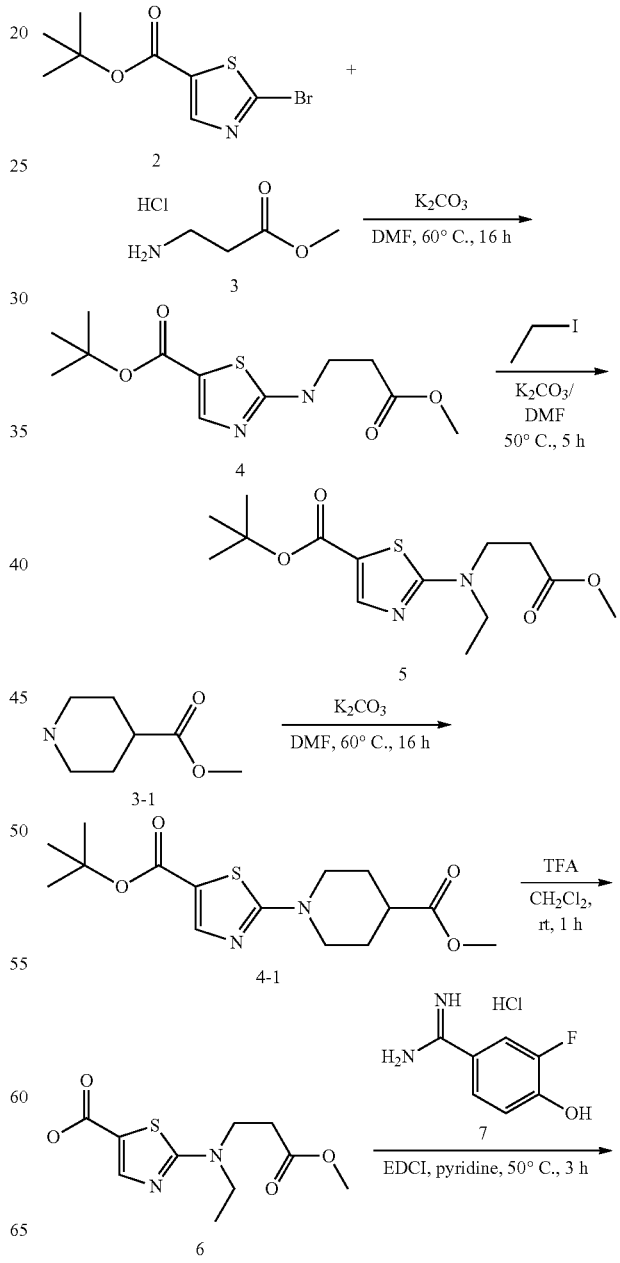

[Reaction Scheme 1]

-continued

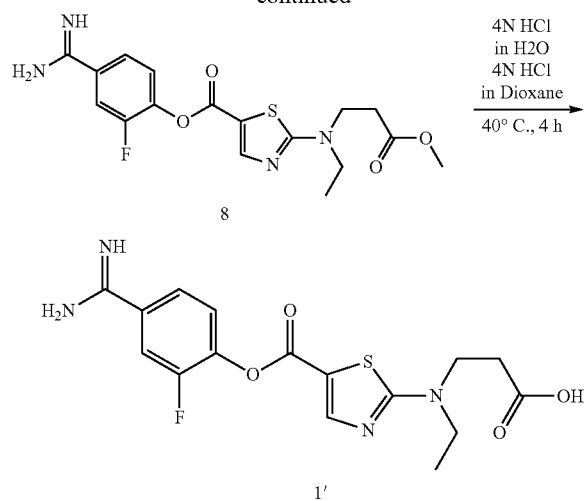

As shown in Reaction Scheme 1 above, tert-butyl 2-bromobenzo[d]thiazole-6-carboxylate (Chemical Formula 2) as a starting material and an amino alkanoic acid (Chemical Formula 3) are heated in the presence of a base such as potassium carbonate and subjected to a coupling reaction, to give a compound of the Chemical Formula 4, which is further treated with an alkylhalogen such as iodoethyl in the presence of a base such as potassium carbonate to synthesize a compound of the Chemical Formula 5.

At this time, the obtained compound is treated in the presence of an organic or inorganic acid such as trifluoro acetic acid (TFA) to selectively remove a carboxylic acid protecting group such as tert-butyl, thereby obtaining a compound of the Chemical Formula 6. Then, the obtained compound is subjected to a coupling reaction with a compound of Chemical Formula 7 using a coupling reagent such as ethyl carbodiimide hydrochloride (EDCl) to prepare a compound of Chemical Formula 8. In the final step, the alkyl carboxylic acid ester is selectively hydrolyzed in the presence of an acid to obtain the compound of Chemical Formula 1' as the desired compound.

On the other hand, in the case of the compound having the structure of forming a substituted or substituted 5- to 7-membered heterocyclic ring together with the nitrogen atom to which R1 and R6 in the compound of Chemical Formula 1 are bonded, the compound is synthesized using a secondary aminoalkanoic acid such as the compound of Chemical Formula 3-1 in the same manner as in the preparation method of Chemical Formula 4, which is an intermediate, to produce the compound of Chemical Formula 4-2. The target compound can be obtained by using a method similar to the method for preparing the compound of the Chemical Formula 1', which is the above-mentioned target compound.

In addition, when the compound according to the present invention has a benzothiazole ring, it can be prepared by the following Reaction Scheme 2.

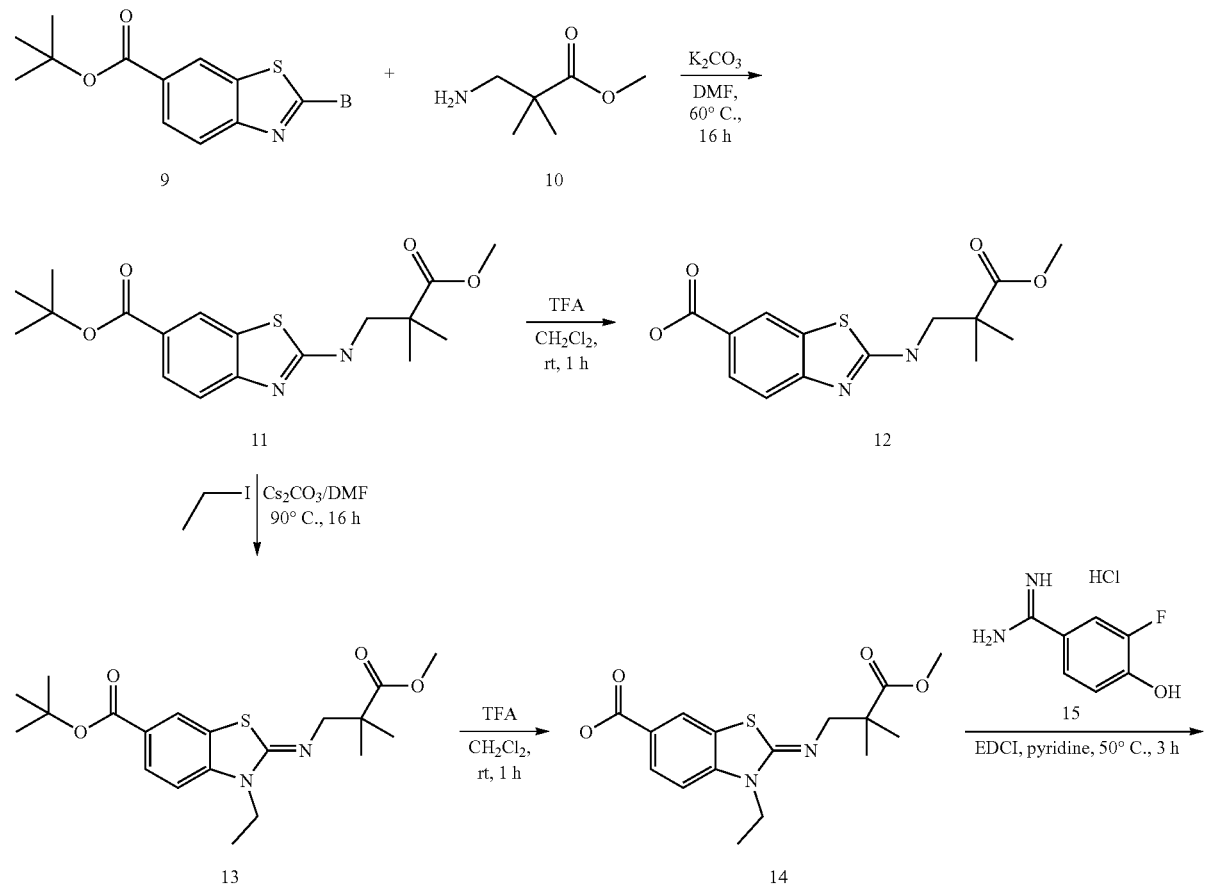

-continued

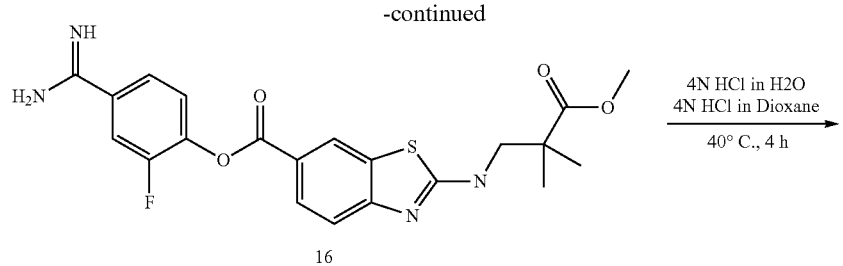

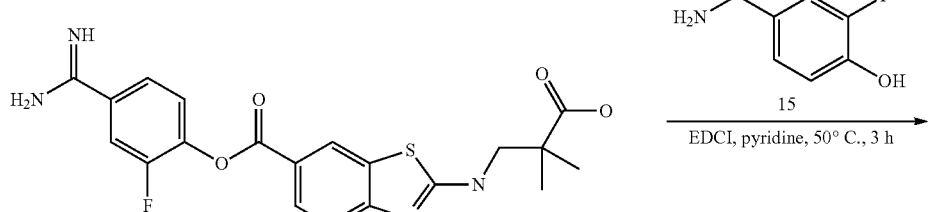

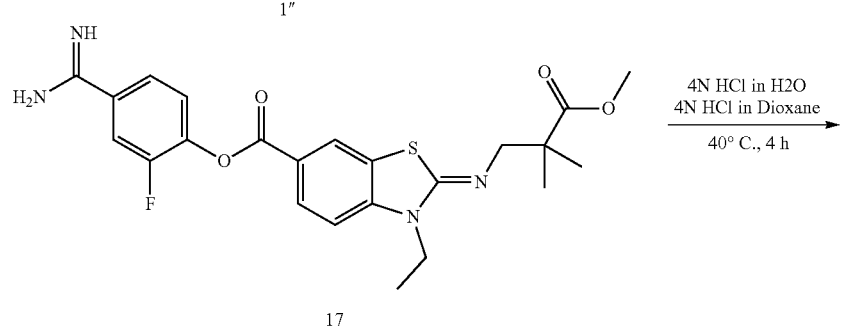

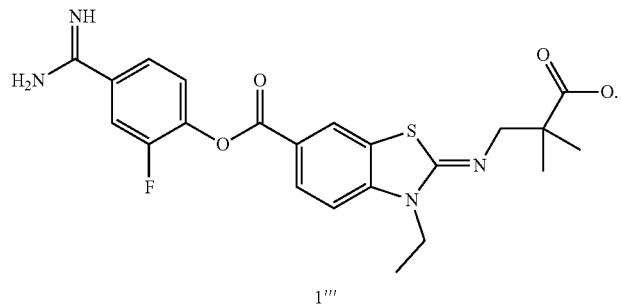

As shown in Reaction Scheme 2 above, tert-butyl 2-bromobenzo[d]thiazole-6-carboxylate (Chemical Formula 9) as a starting material and an amino alkanoic acid (Chemical Formula 10) are heated in the presence of a base such as potassium carbonate and subjected to a coupling reaction to give a compound of the Chemical Formula 11. At this time, the obtained compound is treated in the presence of an organic or inorganic acid such as trifluoro acetic acid (TFA) to selectively remove a carboxylic acid protecting group such as tert-butyl, thereby obtaining a compound of the Chemical Formula 12. Then, the obtained compound is subjected to a coupling reaction with a compound of Chemical Formula 15 using a coupling reagent such as ethyl carbodiimide hydrochloride (EDCl) to prepare a compound of Chemical Formula 16. In the final step, the alkyl carboxylic acid ester is selectively hydrolyzed in the presence of an acid to obtain the compound of Chemical Formula 1" as the desired compound.

On the other hand, for the production of a benzothiazolylidine compound having, as a substituent, an alkyl substituted or unsubstituted with nitrogen of the benzothiazole ring, a substituted or unsubstituted alkyl halide such as iodoethyl of the Reaction Scheme 2 is added to the compound of Chemical Formula 11, which is an intermediate, and heated in the presence of a base such as cesium carbonate to obtain the compound of Chemical Formula 13. At this time, the obtained compound is treated in the presence of an organic or inorganic acid such as trifluoro carboxylic acid to selectively remove a carboxylic acid protecting group such as tert-butyl, thereby obtaining a compound of Chemical Formula 7. Then, the obtained compound is subjected to a coupling reaction with a compound of Chemical Formula 15 using a coupling reagent such as ethyl carbodiimide hydrochloride (EDCl) to prepare a compound of Chemical Formula 17. In the final step, the alkyl carboxylic acid ester is selectively hydrolyzed in the presence of an acid to obtain the desired compound (Chemical Formula 1''').

EXAMPLE

Hereinafter, preferred examples and experimental examples are presented to facilitate understanding of the present invention. However, these examples and experimental examples are provided only for ab better understanding of the present invention, and the contents of the present invention are not limited thereto.

[Preparation Example 1]
2-Bromothiazole-5-carboxylic Acid

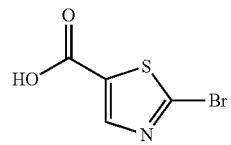

After 20.0 g (90.0 mmol) of methyl 2-bromothiazole-5-carboxylate was dissolved in 250 mL of tetrahydrofuran and 50 mL of water, 3.78 g (90.0 mmol) of lithium hydroxide monohydrate was added thereto at room temperature and stirred for 12 hours. The reaction mixture was concentrated under reduced pressure until the tetrahydrofuran was removed, and a 1N aqueous hydrogen chloride solution was added to the remaining aqueous layer until pH 2 was reached. Ethyl acetate was added to the aqueous solution, and the reaction mixture was extracted and the organic layers were combined. The combined organic layers were dried again with sodium sulfate, and then concentrated under reduced pressure to obtain 17.0 g (91%) of the target compound.
MS (ESI) m/z: 209 [M+H]$^+$

[Preparation Example 2] Tert-butyl 2-bromothiazole-5-carboxylate

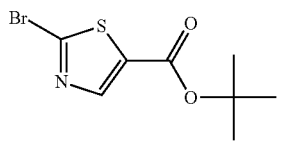

After 4.86 g (23.4 mmol) of the compound 2-bromothiazole-5-carboxylic acid obtained in [Preparation Example 1] was dissolved in 31 mL of tert-butanol and 16 mL of dichloromethane, 6.44 mL (28.0 mmol) of di-tert-butyl dicarbonate, 0.285 g (2.34 mmol) of DMAP and 0.756 mL (9.34 mmol) of pyridine were added thereto at room temperature and stirred for 24 hours. The reaction mixture was concentrated under reduced pressure, ethyl acetate and 0.5 N aqueous hydrogen chloride solution were added until pH 6 was reached. The reaction mixture was extracted twice and the organic layers were combined. The combined organic layers were washed again with 0.5 N aqueous sodium hydroxide solution and brine. The combined organic layers were dried over sodium sulfate, and then concentrated under reduced pressure to obtain 4.89 g (79%) of the target compound.
MS (ESI) m/z: 265 [M+H]$^+$

[Example 1] 3-((5-((4-carbamimidoyl-2-fluorophenoxy)carbonyl)thiazol-2-yl)(ethyl)amino)propanoic Acid

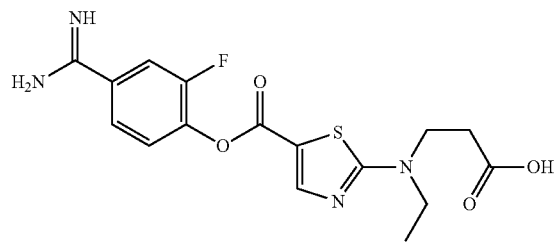

Step 1. Tert-butyl 2-((3-methoxy-3-oxopropyl)amino)thiazole-5-carboxylate

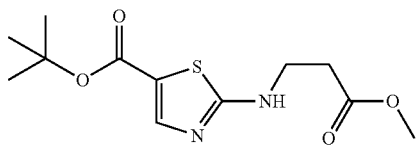

After 2.0 g (7.57 mmol) of the compound tert-butyl 2-bromothiazole-5-carboxylate obtained in [Preparation Example 2] was dissolved in 30 mL of dimethylformamide, 1.16 g (8.33 mmol) of methyl 3-aminopropanoate hydrogen chloride salt and 1.57 g (11.36 mmol) of potassium carbonate were added thereto at room temperature and stirred at 60° C. for 16 hours. After the reaction mixture was cooled to room temperature, water was poured into the reaction mixture to stop the reaction. The reaction mixture was extracted three times with ethyl acetate and the organic layers were combined. The combined organic layers were washed with brine, dried over sodium sulfate, then concentrated under reduced pressure, and purified by MPLC to give 1.8 g (83%) of the target compound as a yellow solid.
MS (ESI) m/z: 287 [M+H]$^+$ Step 2. Tert-butyl 2-(ethyl(3-methoxy-3-oxopropyl)amino)thiazole-5-carboxylate

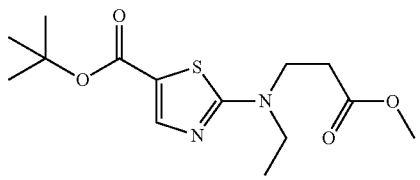

After 1.8 g (6.29 mmol) of the compound tert-butyl 2-((3-methoxy-3-oxopropyl)amino)thiazole-5-carboxylate obtained in step 1 was dissolved in 25 mL of dimethylformamide, 1.30 g (9.43 mmol) of potassium carbonate and 1.176 g (7.54 mmol) of iodoethane were added thereto and stirred at 50° C. for 5 hours. After the reaction mixture was cooled to room temperature, water was poured into the reaction mixture to stop the reaction. The reaction mixture was extracted three times with ethyl acetate and the organic layers were combined. The combined organic layers were washed with brine, dried over sodium sulfate, and then concentrated under reduced pressure, and purified by MPLC to give 1.5 g (76%) of the target compound as a pale yellow liquid.

MS (ESI) m/z: 315 [M+H]+

Step 3. 2-(Ethyl(3-methoxy-3-oxopropyl)amino) thiazole-5-carboxylic Acid

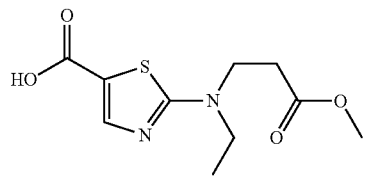

After 1.5 g (4.77 mmol) of the compound tert-butyl 2-(ethyl(3-methoxy-3-oxopropyl) amino)thiazole-5-carboxylate obtained in step 2 was dissolved in 10 mL of dichloromethane, 5.0 mL (65.3 mmol) of trifluoroacetic acid was added, and then stirred at room temperature for 1 hour. The reaction mixture was concentrated under reduced pressure to give 1.7 g (quant) of the target compound as a yellow liquid without a purification step.

MS (ESI) m/z 259 [M+H]+

Step 4. 4-Carbamimidoyl-2-fluorophenyl 2-(ethyl(3-methoxy-3-oxopropyl)amino)thiazole-5-carboxylate

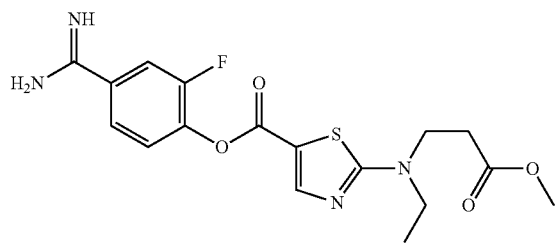

After 1.7 g (6.58 mmol) of the compound 2-(ethyl(3-methoxy-3-oxopropyl)amino)thiazole-5-carboxylic acid obtained in step 3 was dissolved in 7 mL of pyridine, 1.38 g (7.24 mmol) of 3-fluoro-4-hydroxybenzimidamide hydrogen chloride and 2.27 g (11.85 mmol) of EDCI were added thereto and stirred at 50° C. for 3 hours. The reaction mixture was concentrated under reduced pressure, and purified by prep-HPLC to give 2.0 g (77%) of the target compound as a white solid.

MS (ESI) m/z: 395 [M+H]+

Step 5. 3-((5-((4-carbamimidoyl-2-fluorophenoxy) carbonyl)thiazol-2-yl)(ethyl)amino)propanoic Acid

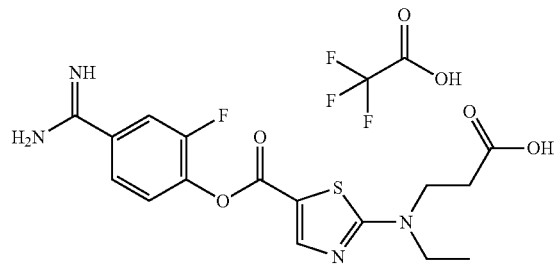

To 1.2 g (3.04 mmol) of the compound 4-carbamimidoyl-2-fluorophenyl 2-(ethyl(3-methoxy-3-oxopropyl)amino)thiazole-5-carboxylate obtained in step 4 was added 4 mL of HCL (4N in H2O) and 4 mL of HCl (4N in dioxane) at room temperature, and the mixture was stirred at 40° C. for 4 hours. After the reaction was completed, the reaction mixture was concentrated under reduced pressure, and purified by prep-HPLC to give 0.68 g (58%) of the target compound as a white solid.

1H NMR (400 MHz, TFA salt, DMSO-d6) δ 12.48 (br s, 1H), 9.41 (br s, 2H), 9.15 (br s, 2H), 8.20 (s, 1H) 7.93-7.88 (m, 1H), 7.74-7.67 (m, 2H), 3.75 (t, J=6.7 Hz, 2H), 3.60-3.53 (m, 2H), 2.66 (t, J=7.1 Hz, 2H), 1.20 (t, J=7.1 Hz, 2H); MS(ESI) m/z: 381 [M+H]+

[Example 2] 1-(5-((4-Carbamimidoylphenoxy)carbonyl)thiazol-2-yl)piperidine-4-carboxylic Acid

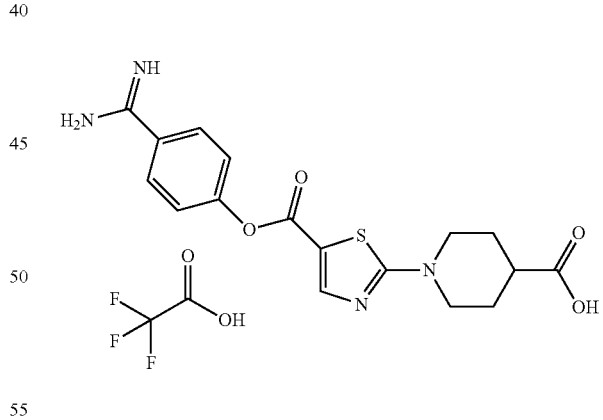

Reaction was carried out from the compound tert-butyl 2-bromothiazole-5-carboxylate obtained in [Preparation Example 2] in the same manner as in [Example 1] to give the title compound. (Yield: 48%)

1H NMR (400 MHz, TFA salt, DMSO-d6) δ 12.43 (br s, 1H), 9.33 (s, 2H), 9.11-8.98 (m, 2H), 8.14 (s, 1H), 7.87 (d, J=8.6 Hz, 2H), 7.51 (d, J=8.7 Hz, 2H), 3.97 (d, J=13.0 Hz, 2H), 3.31-3.27 (m, 2H), 2.64-2.56 (m, 1H), 1.96 (dd, J=3.2, 13.6 Hz, 2H), 1.66-1.56 (m, 2H);

MS (ESI) m/z: 375 [M+H]+

[Example 3] 4-Carbamimidoylphenyl 2-(4-(methoxycarbonyl)piperidin-1-yl)thiazole-5-carboxylate

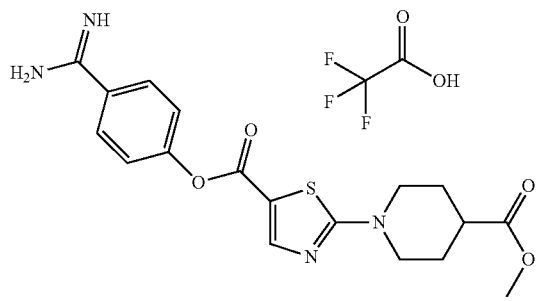

Reaction was carried out from the compound tert-butyl 2-bromothiazole-5-carboxylate obtained in [Preparation Example 2] in the same manner as in [Example 1] to give the title compound. (Yield: 53%)

1H NMR (400 MHz, TFA salt, DMSO-d$_6$) δ 9.33 (br s, 2H), 9.05 (br s, 2H), 8.13 (s, 1H), 7.86 (d, J=8.7 Hz, 2H), 7.50 (d, J=8.8 Hz, 2H), 3.96 (d, J=13.0 Hz, 2H), 3.62 (s, 3H), 3.34-3.27 (m, 2H), 2.75-2.65 (m, 1H), 1.96 (dd, J=3.2, 13.4 Hz, 2H), 1.67-1.57 (m, 2H); MS(ESI) m/z: 389 [M+H]$^+$

[Example 4] 4-Carbamimidoyl-2-fluorophenyl 2-(4-(methoxycarbonyl)piperidin-1-yl)thiazole-5-carboxylate

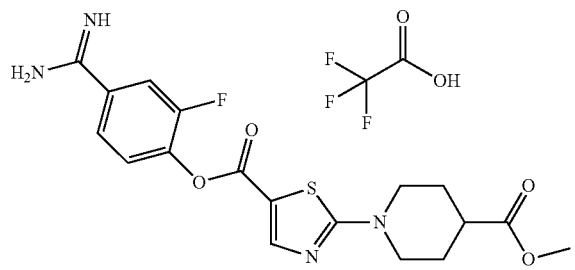

Reaction was carried out from the compound tert-butyl 2-bromothiazole-5-carboxylate obtained in [Preparation Example 2] in the same manner as in [Example 1] to give the title compound. (Yield: 6%)

1H NMR (400 MHz, TFA salt, DMSO-d$_6$) δ 9.41 (br s, 2H), 9.15 (br s, 2H), 8.19 (s, 1H), 7.91-7.88 (m, 1H), 7.73-7.68 (m, 2H), 3.98 (d, J=13.1 Hz, 2H), 3.63 (s, 3H), 3.34-3.30 (m, 2H), 2.77-2.70 (m, 1H), 1.98 (dd, J=3.1, 13.4 Hz, 2H), 1.68-1.58 (m, 2H); MS(ESI) m/z: 407 [M+H]$^+$

[Example 5] 4-Guanidinophenyl 2-(4-(methoxycarbonyl)piperidin-1-yl)thiazole-5-carboxylate

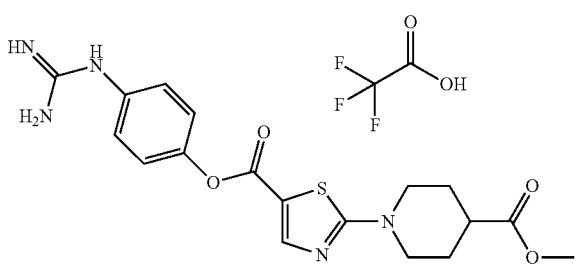

Reaction was carried out from the compound tert-butyl 2-bromothiazole-5-carboxylate obtained in [Preparation Example 2] in the same manner as in [Example 1] to give the title compound. (Yield: 46%)

1H NMR (400 MHz, TFA salt, DMSO-d$_6$) δ 9.68 (br s, 1H), 8.10 (s, 1H), 7.43 (br s, 4H), 7.30 (br s, 4H), 3.97 (d, J=13.2 Hz, 2H), 3.63 (s, 3H), 3.34-3.27 (m, 2H), 2.76-2.69 (m, 1H), 1.97 (dd, J=3.2, 13.4 Hz, 2H), 1.68-1.58 (m, 2H); MS(ESI) m/z: 404 [M+H]$^+$

[Example 6] 1-(5-((4-Guanidinophenoxy)carbonyl)thiazol-2-yl)piperidine-4-carboxylic Acid

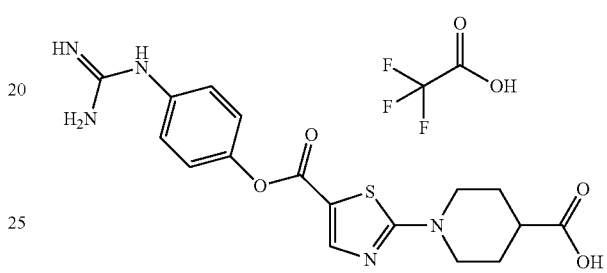

Reaction was carried out from the compound tert-butyl 2-bromothiazole-5-carboxylate obtained in [Preparation Example 2] in the same manner as in [Example 1] to give the title compound. (Yield: 12%)

1H NMR (400 MHz, TFA salt, DMSO-d$_6$) δ 12.42 (br s, 1H), 9.78 (br s, 1H), 8.10 (s, 1H), 7.47 (br s, 4H), 7.30 (br s, 4H), 3.96 (d, J=13.1 Hz, 2H), 3.30-3.26 (m, 2H), 2.62-2.60 (m, 1H), 1.96 (dd, J=3.0, 13.4 Hz, 2H), 1.66-1.56 (m, 2H); MS(ESI) m/z: 390 [M+H]$^+$

[Example 7] 1-(5-((4-Carbamimidoyl-2-fluorophenoxy)carbonyl)thiazol-2-yl)piperidine-4-carboxylic Acid

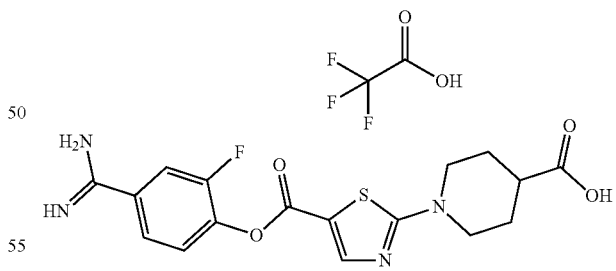

Reaction was carried out from the compound tert-butyl 2-bromothiazole-5-carboxylate obtained in [Preparation Example 2] in the same manner as in [Example 1] to give the title compound. (Yield: 39%)

1H NMR (400 MHz, TFA salt, DMSO-d$_6$) δ 12.43 (br s, 1H), 9.40 (br s, 2H), 9.16 (br s, 2H), 8.19 (s, 1H), 7.90 (d, J=11.0 Hz, 1H), 7.75-7.68 (m, 2H), 3.97 (d, J=12.8 Hz, 2H), 3.16-3.15 (m, 2H), 2.63-2.56 (m, 1H), 1.98-1.95 (m, 2H), 1.66-1.56 (m, 2H); MS(ESI) m/z: 393 [M+H]$^+$

[Example 8] 4-Carbamimidoylphenyl 2-((3-methoxy-3-oxopropyl)(methyl)amino)thiazole-5-carboxylate

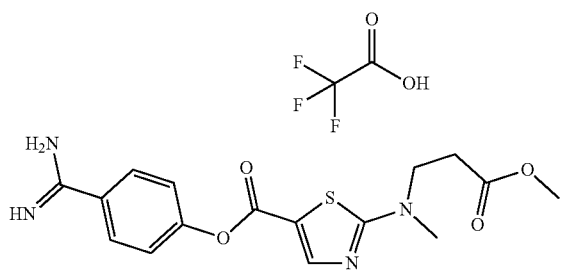

Reaction was carried out from the compound tert-butyl 2-bromothiazole-5-carboxylate obtained in [Preparation Example 2] in the same manner as in [Example 1] to give the title compound. (Yield: 36%)
1H NMR (400 MHz, TFA salt, DMSO-$d_6$) δ 9.34 (br s, 2H), 9.07 (br s, 2H), 8.16 (s, 1H), 7.88 (d, J=8.7 Hz, 2H), 7.52 (d, J=8.7 Hz, 2H), 3.84 (t, J=6.9 Hz, 2H), 3.60 (s, 3H), 3.14 (s, 3H), 2.73 (t, J=7.0 Hz, 2H); MS(ESI) m/z: 363 [M+H]$^+$

[Example 9] 3-((5-((4-Carbamimidoyl)phenoxy)carbonyl)thiazol-2-yl)(methyl)amino)propanoic Acid

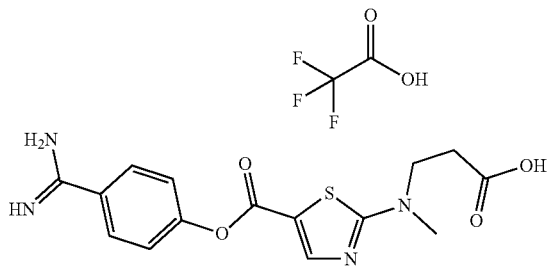

Reaction was carried out from the compound tert-butyl 2-bromothiazole-5-carboxylate obtained in [Preparation Example 2] in the same manner as in [Example 1] to give the title compound. (Yield: 10%)
1H NMR (400 MHz, TFA salt, DMSO-$d_6$) δ 9.36 (br s, 2H), 9.17 (br s, 2H), 8.16 (s, 1H), 7.88 (d, J=6.84 Hz, 2H), 7.51 (d, J=6.92 Hz, 2H), 3.79 (m, 2H), 3.15 (s, 3H), 2.64 (m, 2H); MS(ESI) m/z: 349 [M+H]$^+$

[Example 10] 4-Carbamimidoylphenyl 2-((3-methoxy-3-oxopropyl)amino)thiazole-5-carboxylate

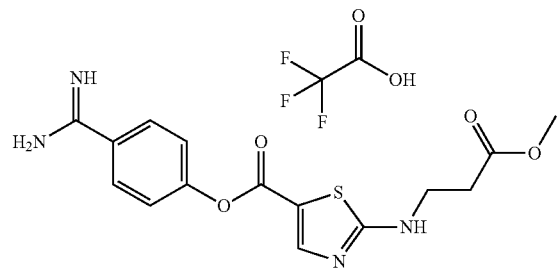

Reaction was carried out from the compound tert-butyl 2-bromothiazole-5-carboxylate obtained in [Preparation Example 2] in the same manner as in [Example 1] to give the title compound. (Yield: 50%)
1H NMR (400 MHz, TFA salt, DMSO-$d_6$) δ 9.34 (br s, 2H), 9.16 (br s, 2H), 8.87 (s, 1H), 8.07 (s, 1H), 7.88 (d, J=7.1 Hz, 2H), 7.50 (d, J=6.9 Hz, 2H), 3.62 (s, 3H), 3.62-3.54 (m, 2H), 2.70-2.65 (m, 2H); MS(ESI) m/z: 349 [M+H]$^+$

[Example 11] 4-Carbamimidoylphenyl 2-((4-methoxy-4-oxobutyl)(methyl)amino)thiazole-5-carboxylate

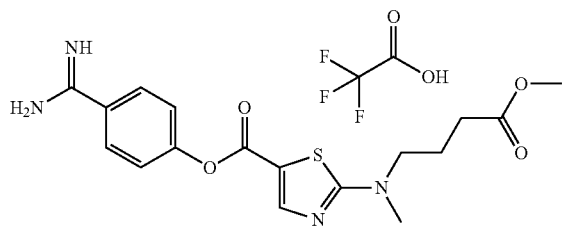

Reaction was carried out from the compound tert-butyl 2-bromothiazole-5-carboxylate obtained in [Preparation Example 2] in the same manner as in [Example 1] to give the title compound. (Yield: 21%)
1H NMR (400 MHz, TFA salt, DMSO-$d_6$) δ 9.33 (br s, 2H), 9.09 (br s, 2H), 8.14 (s, 1H), 7.88 (d, J=8.7 Hz, 2H), 7.52 (d, J=8.6 Hz, 2H), 3.64-3.57 (m, 2H), 3.62 (s, 3H), 3.13 (s, 3H), 2.37 (t, J=8.2 Hz, 2H), 1.93-1.85 (m, 2H); MS(ESI) m/z: 377 [M+H]$^+$

[Example 12] 4-Carbamimidoylphenyl 2-(ethyl(3-methoxy-3-oxopropyl)amino)thiazole-5-carboxylate

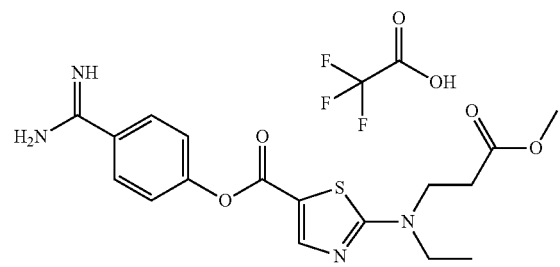

Reaction was carried out from the compound tert-butyl 2-bromothiazole-5-carboxylate obtained in [Preparation Example 2] in the same manner as in [Example 1] to give the title compound. (Yield: 21%)
1H NMR (400 MHz, TFA salt, DMSO-$d_6$) δ 9.34 (br s, 2H), 9.16 (br s, 2H), 8.15 (s, 1H), 7.88 (d, J=8.4 Hz, 2H), 7.51 (d, J=8.3 Hz, 2H), 3.79 (t, J=6.7 Hz, 2H), 3.61 (s, 3H), 3.58-3.52 (m, 2H), 2.75 (t, J=7.0 Hz, 2H), 1.19 (t, J=7.0 Hz, 3H); MS(ESI) m/z: 377 [M+H]$^+$

[Example 13] 3-((5-((4-Carbamimidoyl)phenoxy) carbonyl)thiazol-2-yl)amino)propanoic Acid

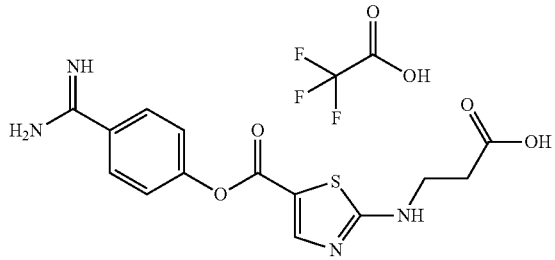

Reaction was carried out from the compound tert-butyl 2-bromothiazole-5-carboxylate obtained in [Preparation Example 2] in the same manner as in [Example 1] to give the title compound. (Yield: 29%)
1H NMR (400 MHz, TFA salt, DMSO-$d_6$) δ 12.36 (br s, 1H), 9.34 (br s, 2H), 9.19 (br s, 2H), 8.86 (t, J=5.0 Hz, 1H), 8.07 (s, 1H), 7.86 (d, J=8.6 Hz, 2H), 7.50 (d, J=8.3 Hz, 2H), 3.56-3.49 (m, 2H), 2.58 (t, J=6.5 Hz, 2H); MS(ESI) m/z: 335 [M+H]$^+$

[Example 14] 3-((5-((4-Carbamimidoyl)phenoxy) carbonyl)thiazol-2-yl)(ethyl)amino)propanoic Acid

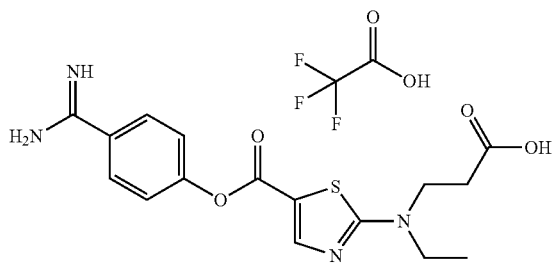

Reaction was carried out from the compound tert-butyl 2-bromothiazole-5-carboxylate obtained in [Preparation Example 2] in the same manner as in [Example 1] to give the title compound. (Yield: 16%)
1H NMR (400 MHz, TFA salt, DMSO-$d_6$) δ 12.5 (br s, 1H), 9.34 (br s, 2H), 9.18 (br s, 2H), 8.15 (s, 1H), 7.88 (d, J=8.5 Hz, 2H), 7.51 (d, J=8.6 Hz, 2H), 3.75 (t, J=6.8 Hz, 2H), 3.60-3.54 (m, 2H), 2.66 (t, J=7.0 Hz, 2H), 1.23-1.15 (m, 3H); MS(ESI) m/z: 363 [M+H]$^+$

[Example 15] 4-((5-((4-Carbamimidoyl)phenoxy) carbonyl)thiazol-2-yl)(methyl)amino)butanoic Acid

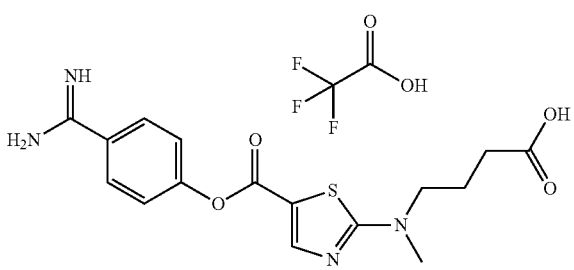

Reaction was carried out from the compound tert-butyl 2-bromothiazole-5-carboxylate obtained in [Preparation Example 2] in the same manner as in [Example 1] to give the title compound. (Yield: 17%)
1H NMR (400 MHz, TFA salt, DMSO-$d_6$) δ 12.2 (br s, 1H), 9.34 (br s, 2H), 9.11 (br s, 2H), 8.14 (s, 1H), 7.88 (d, J=8.6 Hz, 2H), 7.51 (d, J=8.6 Hz, 2H), 3.60 (t, J=5.8 Hz, 2H), 3.13 (s, 3H), 2.27 (t, J=7.2 Hz, 2H), 1.90-1.82 (m, 2H); MS(ESI) m/z: 363 [M+H]$^+$

[Example 16] 4-Carbamimidoylphenyl 2-(3-(methoxycarbonyl)pyrrolidin-1-yl)thiazole-5-carboxylate

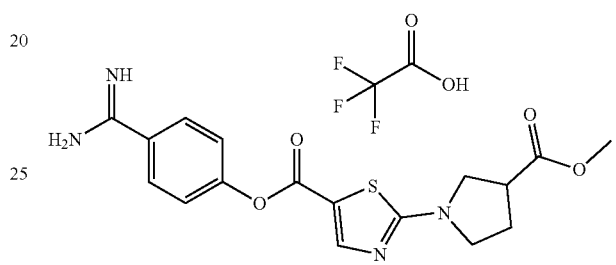

Reaction was carried out from the compound tert-butyl 2-bromothiazole-5-carboxylate obtained in [Preparation Example 2] in the same manner as in [Example 1] to give the title compound. (Yield: 5%)
1H NMR (400 MHz, TFA salt, DMSO-$d_6$) δ 9.34 (br s, 2H), 9.05 (br s, 2H), 8.18 (s, 1H), 8.18 (d, J=8.76 Hz, 2H), 7.52 (d, J=8.76 Hz, 2H), 3.67 (s, 3H), 3.46-3.42 (m, 2H), 2.37-2.21 (m, 2H); MS(ESI) m/z: 375 [M+H]$^+$

[Example 17] 1-(5-((4-Carbamimidoylphenoxy) carbonyl)thiazol-2-yl)pyrrolidine-3-carboxylic Acid

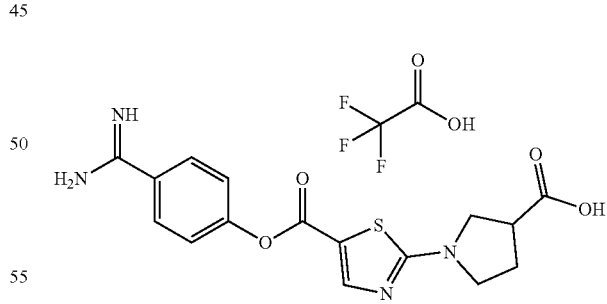

Reaction was carried out from the compound tert-butyl 2-bromothiazole-5-carboxylate obtained in [Preparation Example 2] in the same manner as in [Example 1] to give the title compound. (Yield: 50%)
1H NMR (400 MHz, TFA salt, DMSO-$d_6$) δ 12.78 (brs, 1H), 9.34 (br s, 2H), 9.03 (br s, 2H), 8.17 (s, 1H), 7.88 (d, J=8.68 Hz, 2H), 7.52 (d, J=8.68 Hz, 2H), 2.72-2.67 (m, 2H), 2.23-2.23 (m, 2H); MS(ESI) m/z: 361 [M+H]$^+$

[Example 18] 4-Carbamimidoylphenyl 2-((3-methoxy-2,2-dimethyl-3-oxopropyl)(methyl) amino) thiazole-5-carboxylate

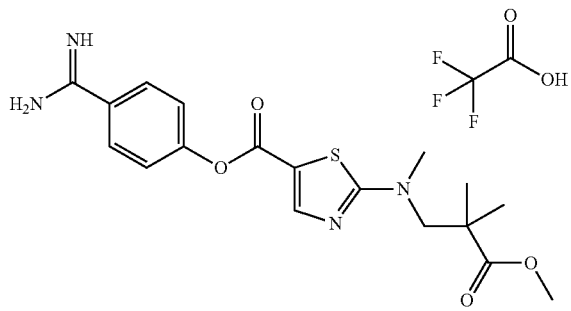

Reaction was carried out from the compound tert-butyl 2-bromothiazole-5-carboxylate obtained in [Preparation Example 2] in the same manner as in [Example 1] to give the title compound. (Yield: 37%)

1H NMR (400 MHz, TFA salt, DMSO-$d_6$) δ 9.31 (br s, 2H), 9.10 (br s, 2H), 8.14 (s, 1H), 7.87 (d, J=8.7 Hz, 2H), 7.52 (d, J=8.7 Hz, 2H), 3.85 (s, 2H), 3.61 (s, 3H), 3.09 (s, 3H), 1.19 (s, 6H); MS (ESI) m/z: 391 [M+H]$^+$

[Example 19] 3-((5-((4-carbamimidoyl)phenoxy)carbonyl)thiazol-2-yl)(methyl)amino)-2,2-dimethyl-propanoic Acid

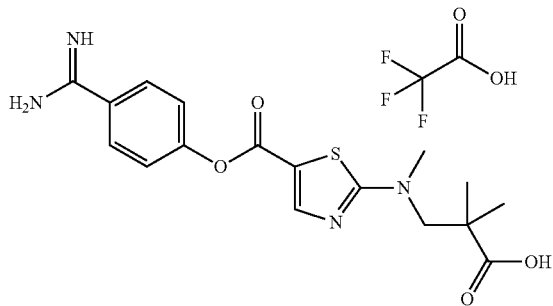

Reaction was carried out from the compound tert-butyl 2-bromothiazole-5-carboxylate obtained in [Preparation Example 2] in the same manner as in [Example 1] to give the title compound. (Yield: 27%)

1H NMR (400 MHz, TFA salt, DMSO-$d_6$) δ 9.34 (br s, 2H), 9.14 (br s, 2H), 8.14 (s, 1H), 7.86 (d, J=8.6 Hz, 2H), 7.51 (d, J=8.7 Hz, 2H), 3.84 (s, 2H), 3.11 (s, 3H), 1.15 (s, 6H); MS(ESI) m/z: 377 [M+H]$^+$

[Example 20] 4-Carbamimidoyl-2-fluorophenyl 2-(ethyl(3-methoxy-3-oxopropyl)amino) thiazole-5-carboxylate

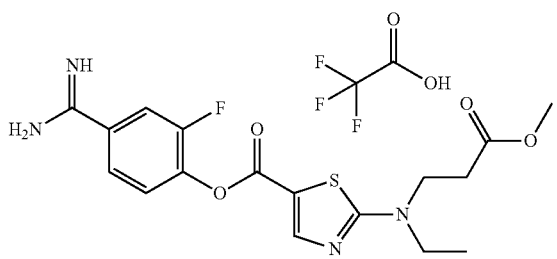

Reaction was carried out from the compound tert-butyl 2-bromothiazole-5-carboxylate obtained in [Preparation Example 2] in the same manner as in [Example 1] to give the title compound. (Yield: 40%)

1H NMR (400 MHz, TFA salt, DMSO-$d_6$) δ 9.40 (br s, 2H), 9.30 (br s, 2H), 8.20 (s, 1H), 7.92-7.89 (m, 1H), 7.74-7.67 (m, 2H), 3.80 (t, J=6.8 Hz, 2H), 3.61 (s, 3H), 3.58-3.52 (m, 2H), 2.75 (t, J=7.1 Hz, 2H), 1.19 (t, J=7.1 Hz, 3H); MS(ESI) m/z: 395 [M+H]$^+$

[Example 21] 4-Carbamimidoyl-2-fluorophenyl 2-((4-methoxy-4-oxobutyl)(methyl)amino)thiazole-5-carboxylate

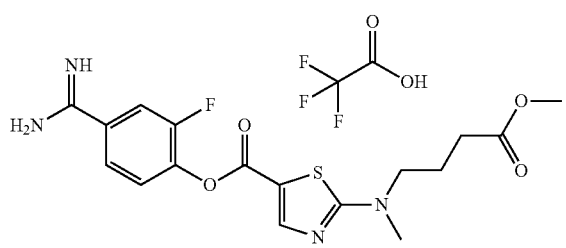

Reaction was carried out from the compound tert-butyl 2-bromothiazole-5-carboxylate obtained in [Preparation Example 2] in the same manner as in [Example 1] to give the title compound. (Yield: 51%)

1H NMR (400 MHz, TFA salt, DMSO-$d_6$) δ 9.35 (br s, 4H), 8.19 (s, 1H), 7.90 (d, J=11.5 Hz, 1H), 7.72-7.68 (m, 2H), 3.65-3.59 (m, 2H), 3.58 (s, 3H), 3.13 (s, 3H), 2.35 (t, J=8.8 Hz, 2H), 1.93-1.83 (m, 2H); MS(ESI) m/z: 395 [M+H]$^+$

[Example 22] 4-((5-((4-Carbamimidoyl-2-fluorophenoxy)carbonyl)thiazol-2-yl)(methyl)amino)butanoic Acid

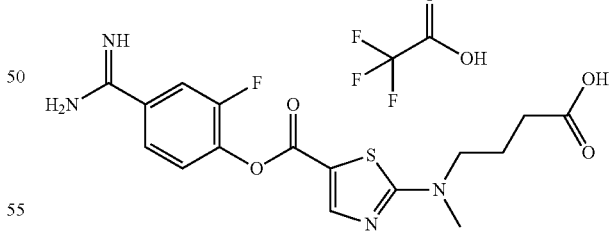

Reaction was carried out from the compound tert-butyl 2-bromothiazole-5-carboxylate obtained in [Preparation Example 2] in the same manner as in [Example 1] to give the title compound. (Yield: 36%)

1H NMR (400 MHz, TFA salt, DMSO-$d_6$) δ 12.19 (br s, 1H), 9.40 (br s, 4H), 9.12 (br s, 1H), 8.19 (s, 1H) 7.91 (d, J=9.9 Hz, 1H), 7.74-7.68 (m, 2H), 3.64-3.58 (m, 2H), 3.14 (s, 3H), 2.28 (t, J=7.2 Hz, 2H), 1.92-1.82 (m, 2H); MS(ESI) m/z: 381 [M+H]$^+$

[Example 23] Methyl 1-(5-((4-guanidinophenyl)carbamoyl)thiazol-2-yl)piperidine-4-carboxylate

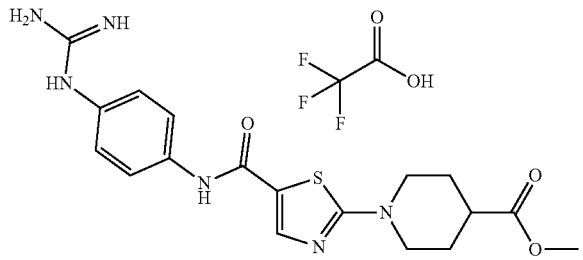

Reaction was carried out from the compound tert-butyl 2-bromothiazole-5-carboxylate obtained in [Preparation Example 2] in the same manner as in [Example 1] to give the title compound. (Yield: 39%)
1H NMR (400 MHz, TFA salt, DMSO-$d_6$) δ 10.10 (br s, 1H), 9.53 (br s, 2H), 8.06 (s, 1H), 7.72 (d, J=8.7 Hz, 2H), 7.30 (br s, 4H), 7.19 (d, J=8.7 Hz, 2H), 3.65 (d, J=13.0 Hz, 2H), 3.62 (s, 3H), 3.24-3.16 (m, 2H), 2.71-2.66 (m, 1H), 1.95-1.90 (m, 2H), 1.65-1.55 (m, 2H);
MS (ESI) m/z: 403 [M+H]$^+$

[Example 24] 4-Carbamimidoylphenyl 2-((3-methoxy-2,2-dimethyl-3-oxopropyl)amino)thiazole-5-carboxylate

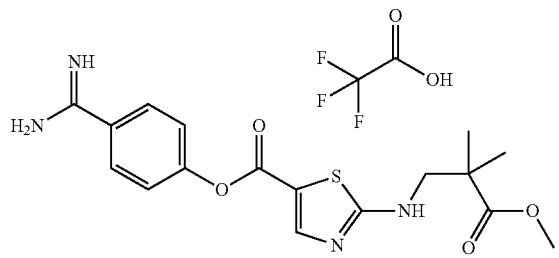

Reaction was carried out from the compound tert-butyl 2-bromothiazole-5-carboxylate obtained in [Preparation Example 2] in the same manner as in [Example 1] to give the title compound. (Yield: 28%)
1H NMR (400 MHz, TFA salt, DMSO-$d_6$) δ 9.33 (br s, 2H), 9.09 (br s, 2H), 8.73 (t, J=6.1 Hz, 1H), 8.03 (s, 1H), 7.87 (d, J=8.7 Hz, 2H), 7.50 (d, J=8.6 Hz, 2H), 3.61 (s, 3H), 3.57 (d, J=6.2 Hz, 2H), 1.17 (s, 6H); MS(ESI) m/z: 377 [M+H]$^+$

[Example 25] (1-(5-((4-Carbamimidoyl)phenoxy)carbonyl)thiazol-2-yl)piperidine-4-carbonyl)-L-aspartic Acid

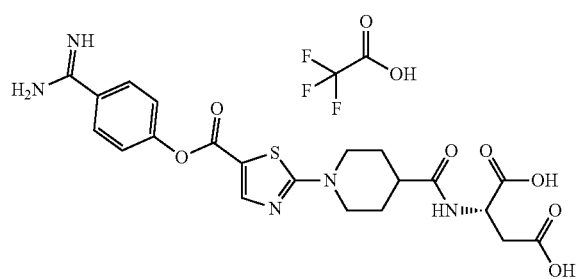

Reaction was carried out from the compound tert-butyl 2-bromothiazole-5-carboxylate obtained in [Preparation Example 2] in the same manner as in [Example 1] to give the title compound. (Yield: 5%)
MS(ESI) m/z: 490 [M+H]$^+$

[Example 26] (1-(5-((4-carbamimidoyl-2-fluorophenoxy)carbonyl)thiazol-2-yl)piperidine-4-carbonyl)-L-aspartate

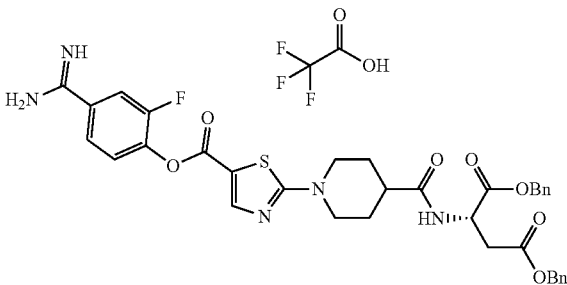

Reaction was carried out from the compound tert-butyl 2-bromothiazole-5-carboxylate obtained in [Preparation Example 2] in the same manner as in [Example 1] to give the title compound. (Yield: 22%)
1H NMR (400 MHz, TFA salt, DMSO-$d_6$) δ 9.39 (br s, 2H), 9.13 (br s, 2H), 8.48 (d, J=7.9 Hz, 1H), 8.19 (s, 1H), 7.91-7.88 (m, 1H), 7.71-7.70 (m, 2H), 7.34-7.30 (m, 10H), 5.11-5.04 (m, 4H) 4.69 (q, J=7.7 Hz, 1H), 3.97 (d, J=11.6 Hz, 2H), 3.24 (t, J=11.8 Hz, 2H), 2.91 (dd, J 5=5.8, 16.4 Hz, 1H), 2.78 (dd, J=7.8, 16.4 Hz, 1H), 1.76-1.70 (m, 2H), 1.59-1.49 (m, 2H);
MS(ESI) m/z: 688 [M+H]$^+$

[Example 27] 4-Carbamimidoylphenyl 2-(4-(phenylcarbamoyl)piperidin-1-yl)thiazole-5-carboxylate

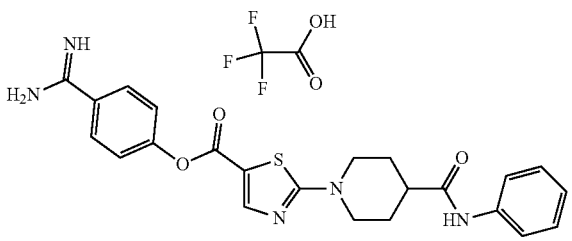

Reaction was carried out from the compound tert-butyl 2-bromothiazole-5-carboxylate obtained in [Preparation Example 2] in the same manner as in [Example 1] to give the title compound. (Yield: 34%)
1H NMR (400 MHz, TFA salt, DMSO-$d_6$) δ 9.98 (br s, 1H), 9.31 (br s, 2H), 8.98 (br s, 2H), 8.14 (s, 1H), 7.87-7.85 (m, 2H), 7.58 (d, J=7.7 Hz, 2H), 7.50 (d, J=8.7 Hz, 2H), 7.29 (t, J=7.6 Hz, 2H), 7.50 (d, J=8.7 Hz, 2H), 7.29 (t, J=7.6 Hz, 2H), 7.01 (t, J=7.4 Hz, 1H), 4.08 (d, J=13.0 Hz, 2H), 3.31-3.25 (m, 2H), 2.71-2.47 (m, 1H), 1.94-1.88 (m, 2H), 1.74-1.64 (m, 2H);
MS(ESI) m/z: 450 [M+H]$^+$

[Example 28] 4-Carbamimidoylphenyl 2-(4-benzamidopiperidin-1-yl)thiazole-5-carboxylate

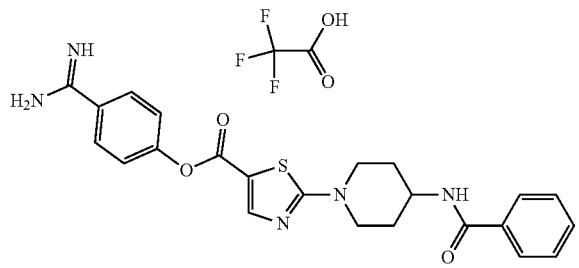

Reaction was carried out from the compound tert-butyl 2-bromothiazole-5-carboxylate obtained in [Preparation Example 2] in the same manner as in [Example 1] to give the title compound. (Yield: 32%)

1H NMR (400 MHz, TFA salt, DMSO-$d_6$) δ 9.32 (br s, 2H), 9.03 (br s, 2H), 8.35 (d, J=7.6 Hz, 1H) 8.16 (s, 1H), 7.88-7.82 (m, 4H), 7.54-7.50 (m, 3H), 7.47-7.44 (m, 2H), 4.18-4.10 (m, 1H), 4.06 (d, J=12.9 Hz, 2H), 3.40-3.37 (m, 2H), 1.97-1.94 (m, 2H), 1.69-1.59 (m, 2H);
MS(ESI) m/z: 450 [M+H]$^+$

[Example 29] 4-Carbamimidoylphenyl 2-(4-((2-methoxy-2-oxoethyl)carbamoyl)piperidin-1-yl)thiazole-5-carboxylate

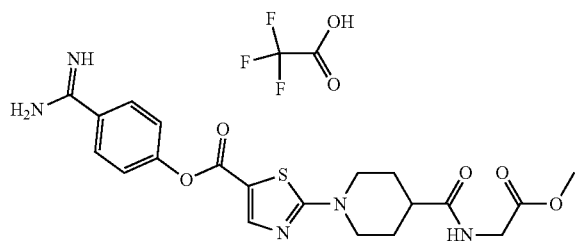

Reaction was carried out from the compound tert-butyl 2-bromothiazole-5-carboxylate obtained in [Preparation Example 2] in the same manner as in [Example 1] to give the title compound. (Yield: 55%)

1H NMR (400 MHz, TFA salt, DMSO-$d_6$) δ 9.26 (br s, 2H), 9.12 (br s, 2H), 8.38 (t, J=5.8 Hz, 1H), 8.14 (s, 1H), 7.87 (d, J=8.7 Hz, 2H), 7.51 (d, J=8.7 Hz, 2H), 4.02 (d, J=13.0 Hz, 2H), 3.82 (d, J=5.9 Hz, 2H), 3.61 (s, 3H), 3.31-3.24 (m, 2H), 2.59-2.54 (m, 1H), 1.86-1.82 (m, 2H), 1.67-1.56 (m, 2H); MS(ESI) m/z: 446 [M+H]$^+$

[Example 30] 4-Carbamimidoylphenyl 2-(4-((3-methoxy-3-oxopropyl)carbamoyl)piperidin-1-yl)thiazole-5-carboxylate

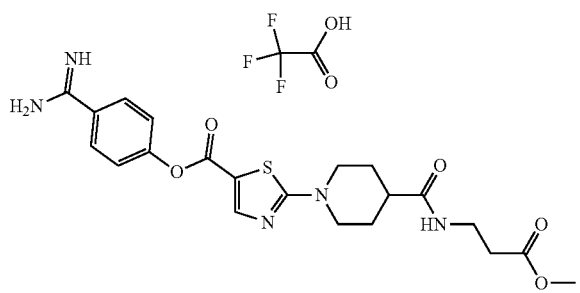

Reaction was carried out from the compound tert-butyl 2-bromothiazole-5-carboxylate obtained in [Preparation Example 2] in the same manner as in [Example 1] to give the title compound. (Yield: 51%)

1H NMR (400 MHz, TFA salt, DMSO-$d_6$) δ 9.32 (br s, 2H), 8.97 (br s, 2H), 8.14 (s, 1H), 8.01 (t, J=5.6 Hz, 1H), 7.87 (d, J=8.7 Hz, 2H), 7.51 (d, J=8.7 Hz, 2H), 4.02 (d, J=12.6 Hz, 2H), 3.58 (s, 3H), 3.29-3.15 (m, 4H), 2.49-2.43 (m, 3H), 1.80-1.76 (m, 2H), 1.64-1.53 (m, 2H);
MS(ESI) m/z: 460 [M+H]$^+$

[Example 31] 4-Carbamimidoylphenyl 2-(4-((4-methoxy-4-oxobutyl)(methyl)carbamoyl) piperidin-1-yl)thiazole-5-carboxylate

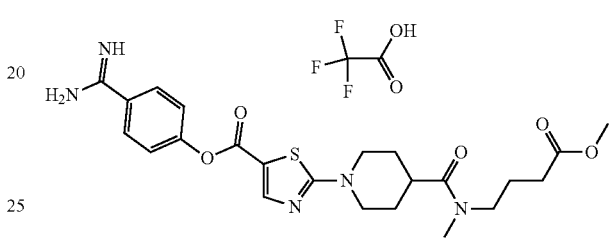

Reaction was carried out from the compound tert-butyl 2-bromothiazole-5-carboxylate obtained in [Preparation Example 2] in the same manner as in [Example 1] to give the title compound. (Yield: 33%)

1H NMR (400 MHz, TFA salt, DMSO-$d_6$) δ 9.32 (br s, 2H), 9.02 (br s, 2H), 8.14 (s, 1H), 7.88-7.86 (m, 2H), 7.52-7.50 (m, 2H), 4.03-3.95 (m, 2H), 3.60 (s, 1H, rotamer, —OCH3), 3.57 (s, 2H, rotamer-OCH3), 3.38-3.31 (m, 2H), 3.30-3.26 (m, 2H), 3.02 (s, 2H, rotamer-CH3), 2.99-2.93 (m, 1H), 2.78 (s, 1H, rotamer-CH3), 2.37 (t, J=7.2 Hz, 1H), 2.24 (t, J=7.4 Hz, 1H), 1.82-1.70 (m, 2H), 1.69-1.62 (m, 2H), 1.59-1.52 (m, 2H); MS(ESI) m/z: 488 [M+H]$^+$

[Example 32] 4-Carbamimidoylphenyl 2-(4-((3-methoxy-2,2-dimethyl-3-oxopropyl)carbamoyl)piperidin-1-yl)thiazole-5-carboxylate

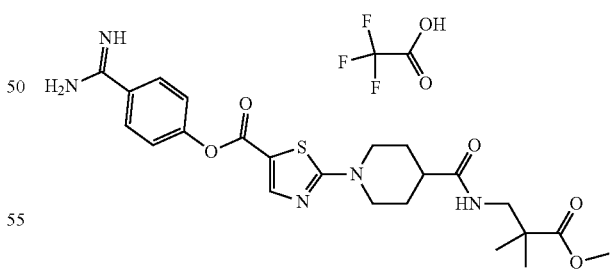

Reaction was carried out from the compound tert-butyl 2-bromothiazole-5-carboxylate obtained in [Preparation Example 2] in the same manner as in [Example 1] to give the title compound. (Yield: 4%)

1H NMR (400 MHz, TFA salt, DMSO-$d_6$) δ 9.32 (br s, 2H), 9.02 (br s, 2H), 8.14 (s, 1H), 7.90-7.86 (m, 3H), 7.51 (d, J=8.7 Hz, 2H), 4.03 (d, J=12.5 Hz, 2H), 3.56 (s, 3H), 3.27-3.20 (m, 4H), 2.55-2.53 (m, 1H), 1.80-1.77 (m, 2H), 1.65-1.55 (m, 2H), 1.06 (s, 6H); MS(ESI) m/z: 488 [M+H]$^+$

[Example 33] (1-(5-((4-Carbamimidoyl)phenoxy)carbonyl)thiazol-2-yl)piperidine-4-carbonyl)glycine

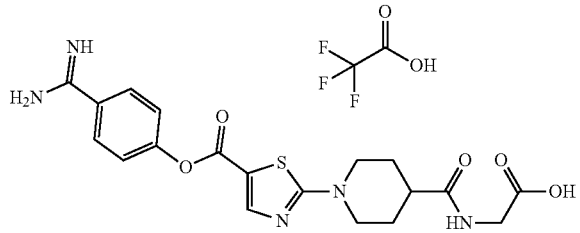

Reaction was carried out from the compound tert-butyl 2-bromothiazole-5-carboxylate obtained in [Preparation Example 2] in the same manner as in [Example 1] to give the title compound. (Yield: 48%)

1H NMR (400 MHz, TFA salt, DMSO-d$_6$) δ 12.55 (br s, 1H), 9.33 (br s, 2H), 9.01 (br s, 2H), 8.26 (t, J=5.8 Hz, 1H), 8.15 (s, 1H), 7.88 (d, J=8.7 Hz, 2H), 7.52 (d, J=8.7 Hz, 2H), 4.04 (d, J=12.8 Hz, 2H), 3.74 (d, J=5.9 Hz, 2H), 3.30-3.24 (m, 2H), 1.86-1.83 (m, 2H), 1.67-1.57 (m, 2H); MS(ESI) m/z: 432 [M+H]$^+$

[Example 34] 3-(1-(5-((4-Carbamimidoyl)phenoxy)carbonyl)thiazol-2-yl)piperidine-4-carboxamido)propanoic Acid

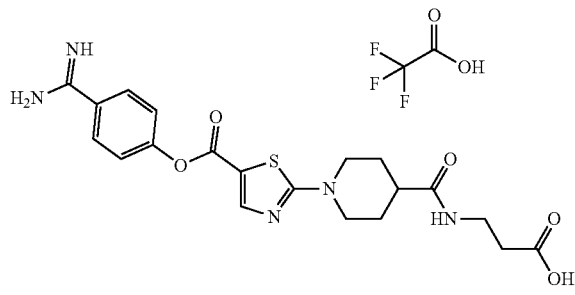

Reaction was carried out from the compound tert-butyl 2-bromothiazole-5-carboxylate obtained in [Preparation Example 2] in the same manner as in [Example 1] to give the title compound. (Yield: 53%)

1H NMR (400 MHz, TFA salt, DMSO-d$_6$) δ 9.33 (br s, 2H), 9.04 (br s, 2H), 8.15 (s, 1H), 7.99 (t, J=5.5 Hz, 1H), 7.89-7.86 (m, 2H), 7.53-7.50 (m, 2H), 4.03 (d, J=12.8 Hz, 2H), 3.26-3.20 (m, 4H), 2.46-2.41 (m, 1H), 2.37 (t, J=6.8 Hz, 2H), 1.81-1.77 (m, 2H), 1.65-1.55 (m, 2H);
MS(ESI) m/z: 446 [M+H]$^+$

[Example 35] 4-(1-(5-((4-Carbamimidoyl)phenoxy)carbonyl)thiazol-2-yl)-N-methylpiperidine-4-carboxamido)butanoic Acid

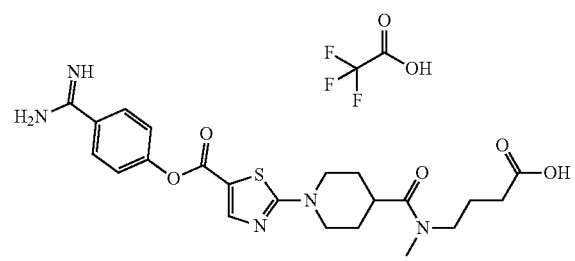

Reaction was carried out from the compound tert-butyl 2-bromothiazole-5-carboxylate obtained in [Preparation Example 2] in the same manner as in [Example 1] to give the title compound. (Yield: 56%)

1H NMR (400 MHz, TFA salt, DMSO-d$_6$) δ 9.33 (br s, 2H), 9.03 (br s, 2H), 8.15 (s, 1H), 7.89-7.87 (m, 2H), 7.53-7.51 (m, 2H), 4.04-3.96 (m, 2H), 3.39-3.35 (m, 2H), 3.34-3.26 (m, 2H), 3.04 (s, 2H, rotamer-CH3), 3.00-2.94 (m, 1H), 2.80 (s, 1H, rotamer-CH3), 2.29 (t, J=7.1 Hz, 1H), 2.15 (t, J=7.4 Hz, 1H), 1.80-1.74 (m, 2H), 1.70-1.65 (m, 2H), 1.64-1.54 (m, 2H); MS(ESI) m/z: 474 [M+H]$^+$

[Example 36] 3-(1-(5-((4-Carbamimidoyl)phenoxy)carbonyl)thiazol-2-yl)piperidine-4-carboxamido)-2,2-dimethyl Propanoic Acid

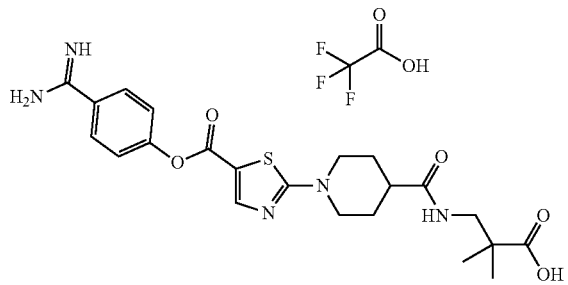

Reaction was carried out from the compound tert-butyl 2-bromothiazole-5-carboxylate obtained in [Preparation Example 2] in the same manner as in [Example 1] to give the title compound. (Yield: 41%)

1H NMR (400 MHz, TFA salt, DMSO-d$_6$) δ 12.24 (br s, 1H), 9.32 (br s, 2H), 9.01 (br s, 2H), 8.14 (s, 1H), 7.87 (d, J=8.8 Hz, 2H), 7.79 (t, J=6.1 Hz, 1H), 7.51 (d, J=8.7 Hz, 2H), 4.03 (d, J=12.5 Hz, 2H), 3.26-3.19 (m, 4H), 2.58-2.53 (m, 1H), 1.80-1.77 (m, 2H), 1.65-1.55 (m, 2H), 1.03 (s, 6H); MS(ESI) m/z: 474 [M+H]$^+$

[Example 37] 4-Carbamimidoyl-2-fluorophenyl 2-(4-((2-methoxy-2-oxoethyl)carbamoyl)piperidin-1-yl)thiazole-5-carboxylate

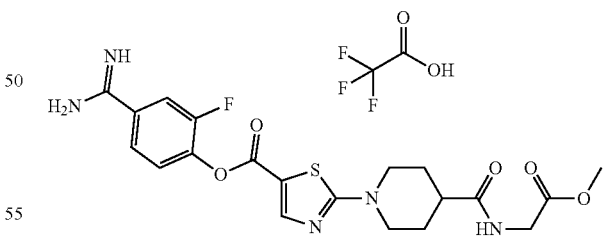

Reaction was carried out from the compound tert-butyl 2-bromothiazole-5-carboxylate obtained in [Preparation Example 2] in the same manner as in [Example 1] to give the title compound. (Yield: 23%)

1H NMR (400 MHz, TFA salt, DMSO-d$_6$) δ 9.30 (br s, 4H), 8.39 (t, J=5.9 Hz, 1H), 8.21 (s, 1H) 7.93-7.90 (m, 1H), 7.74-7.69 (m, 2H), 4.04 (d, J=12.6 Hz, 2H), 3.84 (d, J=5.9 Hz, 2H), 3.63 (s, 3H), 3.30-3.26 (m, 2H), 2.61-2.52 (m, 1H), 1.90-1.84 (m, 2H) 1.68-1.58 (m, 2H);
MS (ESI) m/z: 464 [M+H]$^+$

[Example 38] 4-Carbamimidoyl-2-fluorophenyl 2-(4-((3-methoxy-3-oxopropyl)carbamoyl)piperidin-1-yl)thiazole-5-carboxylate

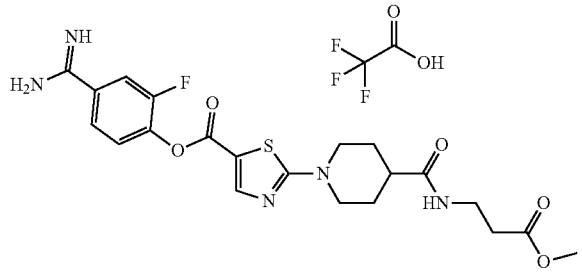

Reaction was carried out from the compound tert-butyl 2-bromothiazole-5-carboxylate obtained in [Preparation Example 2] in the same manner as in [Example 1] to give the title compound. (Yield: 50%)
1H NMR (400 MHz, TFA salt, DMSO-$d_6$) δ 9.37 (br s, 2H), 9.24 (br s, 2H), 8.19 (s, 1H), 8.01 (t, J=5.6 Hz, 1H), 7.91-7.88 (m, 1H), 7.73-7.68 (m, 2H), 4.03 (d, J=12.3 Hz, 2H), 3.58 (s, 3H), 3.29-3.21 (m, 4H), 2.46-2.43 (m, 3H), 1.81-1.77 (m, 2H), 1.64-1.54 (m, 2H); MS(ESI) m/z: 478 [M+H]$^+$

[Example 39] 4-Carbamimidoyl-2-fluorophenyl 2-(4-((3-methoxy-2,2-dimethyl-3-oxopropyl)carbamoyl)piperidin-1-yl)thiazole-5-carboxylate

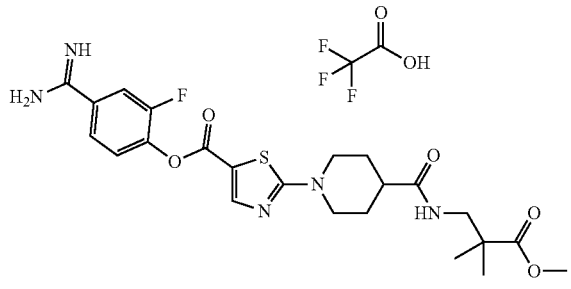

Reaction was carried out from the compound tert-butyl 2-bromothiazole-5-carboxylate obtained in [Preparation Example 2] in the same manner as in [Example 1] to give the title compound. (Yield: 50%)
1H NMR (400 MHz, TFA salt, DMSO-$d_6$) δ 9.40 (br s, 2H), 9.20 (br s, 2H), 8.19 (s, 1H), 7.91-7.87 (m, 2H), 7.73-7.68 (m, 2H), 4.04 (d, J=12.4 Hz, 2H), 3.57 (s, 3H), 3.28-3.20 (m, 4H), 2.49-2.48 (m, 1H), 1.81-1.77 (m, 2H), 1.65-1.55 (m, 2H), 1.06 (s, 6H); MS(ESI) m/z: 506 [M+H]$^+$

[Example 40] 4-carbamimidoylphenyl 2-(4-((4-methoxyphenyl)carbamoyl)piperidin-1-yl)thiazole-5-carboxylate

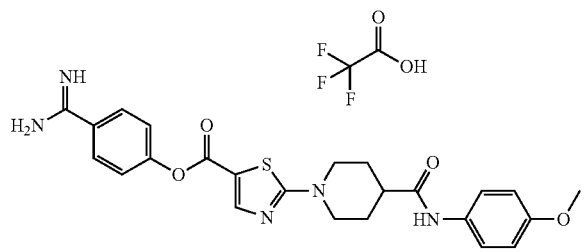

Reaction was carried out from the compound tert-butyl 2-bromothiazole-5-carboxylate obtained in [Preparation Example 2] in the same manner as in [Example 1] to give the title compound. (Yield: 9%)
1H NMR (400 MHz, TFA salt, DMSO-$d_6$) δ 9.86 (br s, 2H), 9.34 (br s, 2H), 9.10-8.96 (m, 2H), 8.16 (s, 1H), 7.88 (d, J=8.6 Hz, 2H), 7.55-7.48 (m, 4H), 6.87 (d, J=9.0 Hz, 2H), 4.14-4.06 (m, 2H), 3.71 (s, 3H), 3.35-3.25 (m, 2H), 2.70-2.64 (m, 1H), 1.96-1.90 (m, 2H), 1.77-1.64 (m, 2H); MS(ESI) m/z: 480 [M+H]$^+$

[Example 41] 4-Carbamimidoyl-2-fluorophenyl 2-(4-((4-methoxy-4-oxobutyl)(methyl)carbamoyl)piperidin-1-yl)thiazole-5-carboxylate

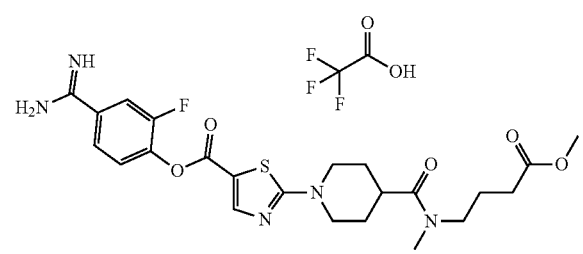

Reaction was carried out from the compound tert-butyl 2-bromothiazole-5-carboxylate obtained in [Preparation Example 2] in the same manner as in [Example 1] to give the title compound. (Yield: 16%)
1H NMR (400 MHz, TFA salt, DMSO-$d_6$) δ 9.41 (br s, 2H), 9.19 (br s, 2H), 8.21 (s, 1H), 7.93-7.90 (m, 1H), 7.77-7.70 (m, 2H), 4.05-3.96 (m, 2H), 3.62 (s, 1H, rotamer, —OCH3), 3.58 (s, 2H, rotamer-OCH3), 3.39-3.32 (m, 2H), 3.31-3.28 (m, 2H), 3.04 (s, 2H, rotamer-CH3), 3.02-2.95 (m, 1H), 2.79 (s, 1H, rotamer-CH3), 2.39 (t, J=7.2 Hz, 1H), 2.25 (t, J=7.5 Hz, 1H), 1.86-1.77 (m, 2H), 1.74-1.67 (m, 2H), 1.64-1.54 (m, 2H); MS(ESI) m/z: 506 [M+H]$^+$

[Example 42] (1-(5-((4-Carbamimidoyl-2-fluorophenoxy)carbonyl)thiazol-2-yl)piperidine-4-carbonyl)glycine

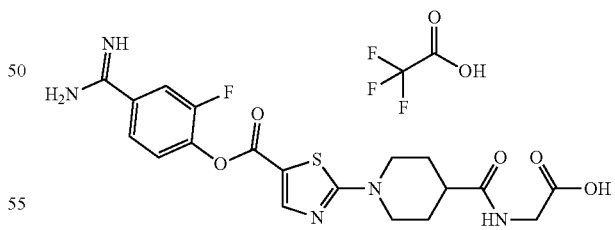

Reaction was carried out from the compound tert-butyl 2-bromothiazole-5-carboxylate obtained in [Preparation Example 2] in the same manner as in [Example 1] to give the title compound. (Yield: 15%)
1H NMR (400 MHz, TFA salt, DMSO-$d_6$) δ 12.54 (br s, 1H), 9.42 (br s, 2H), 9.15 (br s, 2H), 8.27 (t, J=5.8 Hz, 1H), 8.21 (s, 1H), 7.93-7.90 (m, 1H), 7.75-7.70 (m, 2H), 4.05 (d, J=12.4 Hz, 2H), 3.75 (d, J=5.9 Hz, 2H), 3.30-3.27 (m, 2H), 2.59-2.50 (m, 1H), 1.87-1.84 (m, 2H), 1.68-1.58 (m, 2H); MS(ESI) m/z: 450 [M+H]$^+$

[Example 43] 3-(1-(5-((4-Carbamimidoyl-2-fluorophenoxy)carbonyl)thiazol-2-yl)piperidine-4-carboxamido)propanoic Acid

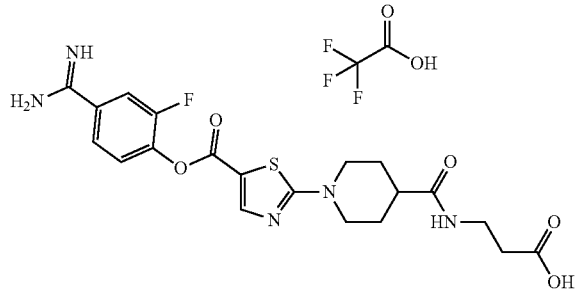

Reaction was carried out from the compound tert-butyl 2-bromothiazole-5-carboxylate obtained in [Preparation Example 2] in the same manner as in [Example 1] to give the title compound. (Yield: 17%)

1H NMR (400 MHz, TFA salt, DMSO-$d_6$) δ 12.21 (br s, 1H), 9.40 (br s, 2H), 9.17 (br s, 2H), 8.19 (s, 1H), 7.98 (t, J=5.4 Hz, 1H), 7.92-7.89 (m, 1H), 7.71-7.70 (m, 2H), 4.03 (d, J=12.3 Hz, 2H), 3.28-3.21 (m, 4H), 2.49-2.41 (m, 1H), 2.36 (t, J=6.8 Hz, 2H), 1.81-1.78 (m, 2H), 1.65-1.55 (m, 2H); MS(ESI) m/z: 464 [M+H]$^+$

[Example 44] 4-(1-(5-((4-carbamimidoyl-2-fluorophenoxy)carbonyl)thiazol-2-yl)-N-methylpiperidine-4-carboxamido)butanoic Acid

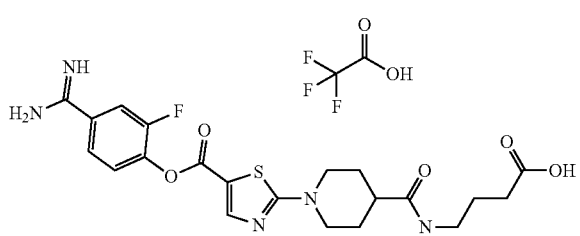

Reaction was carried out from the compound tert-butyl 2-bromothiazole-5-carboxylate obtained in [Preparation Example 2] in the same manner as in [Example 1] to give the title compound. (Yield: 56%)

1H NMR (400 MHz, TFA salt, DMSO-$d_6$) δ 9.40 (br s, 2H), 9.13 (br s, 2H), 8.19 (s, 1H), 7.92-7.89 (m, 1H), 7.73-7.68 (m, 2H), 4.03-3.94 (m, 2H), 3.38-3.34 (m, 2H), 3.32-3.27 (m, 2H), 3.03 (s, 2H, rotamer-CH3), 2.99-2.94 (m, 1H), 2.79 (s, 1H, rotamer-CH3), 2.28 (t, J=7.1 Hz, 1H), 2.14 (t, J=7.4 Hz, 1H), 1.79-1.73 (m, 2H), 1.69-1.64 (m, 2H), 1.62-1.51 (m, 2H); MS(ESI) m/z: 492 [M+H]$^+$

[Example 45] 3-(1-(5-((4-Carbamimidoyl-2-fluorophenoxy)carbonyl)thiazol-2-yl)piperidine-4-carboxamido)-2, 2-dimethylpropanoic Acid

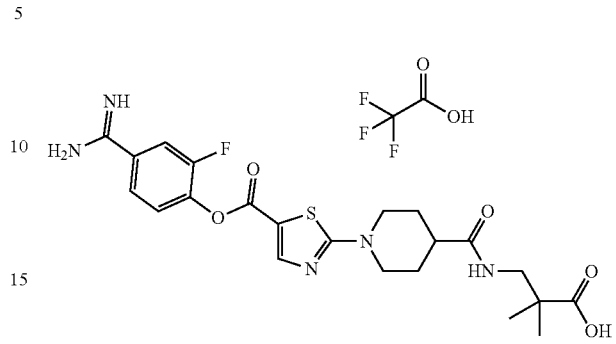

Reaction was carried out from the compound tert-butyl 2-bromothiazole-5-carboxylate obtained in [Preparation Example 2] in the same manner as in [Example 1] to give the title compound. (Yield: 36%)

1H NMR (400 MHz, TFA salt, DMSO-$d_6$) δ 9.39 (br s, 2H), 9.15 (br s, 2H), 8.19 (s, 1H), 7.91-7.89 (m, 1H), 7.80 (t, J=6.2 Hz, 1H), 7.78-7.68 (m, 2H), 4.04 (d, J=12.6 Hz, 2H), 3.27-3.20 (m, 4H), 2.59-2.53 (m, 1H), 1.81-1.78 (m, 2H), 1.66-1.56 (m, 2H), 1.04 (s, 6H); MS(ESI) m/z: 492 [M+H]$^+$

[Example 46] Di-tert-butyl(3-((5-((4-carbamimidoyl-2-fluorophenoxy)carbonyl)thiazol-2-yl)(ethyl)amino)propanoyl)-L-aspartate

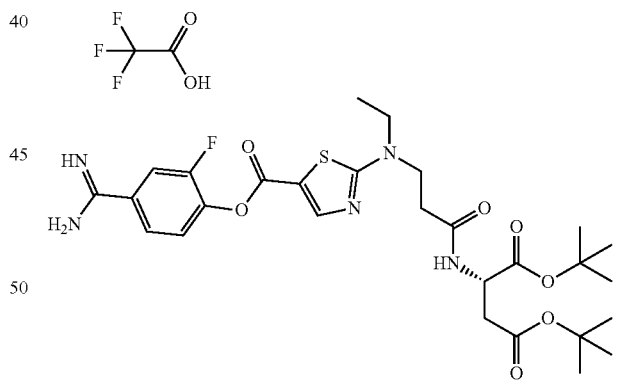

Reaction was carried out from the compound tert-butyl 2-bromothiazole-5-carboxylate obtained in [Preparation Example 2] in the same manner as in [Example 1] to give the title compound. (Yield: 48%)

1H NMR (400 MHz, TFA salt, DMSO-$d_6$) δ 9.40 (br s, 2H), 9.14 (br s, 2H), 8.42 (d, J=8.0 Hz, 1H), 8.19 (s, 1H), 7.92-7.89 (m, 1H), 7.74-7.67 (m, 2H), 4.51-4.45 (m, 1H), 3.73-3.72 (m, 2H), 3.56-3.50 (m, 2H), 2.67-2.58 (m, 1H), 2.56-2.51 (m, 3H), 1.38 (s, 9H), 1.38 (s, 9H), 1.18 (t, J=7.0 Hz, 3H); MS(ESI) m/z: 608 [M+H]$^+$

[Example 47] (3-((5-((4-Carbamimidoyl-2-fluoro-phenoxy)carbonyl)thiazol-2-yl)(ethyl)amino)pro-panoyl)-L-aspartic Acid

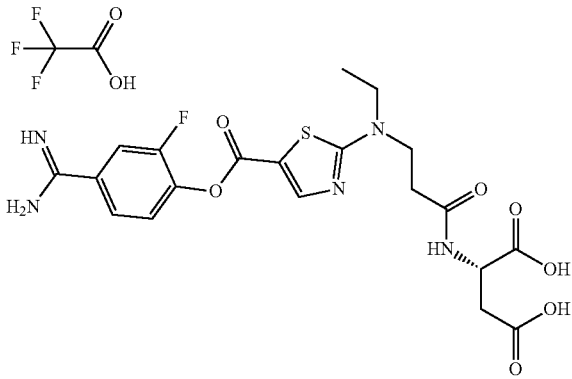

Reaction was carried out from the compound tert-butyl 2-bromothiazole-5-carboxylate obtained in [Preparation Example 2] in the same manner as in [Example 1] to give the title compound. (Yield: 37%)

1H NMR (400 MHz, TFA salt, DMSO-d$_6$) δ 9.41 (br s, 2H), 9.16 (br s, 2H), 8.41 (d, J=7.9 Hz, 1H), 8.20 (s, 1H), 7.92-7.89 (m, 1H), 7.75-7.68 (m, 2H), 4.56-4.51 (m, 1H), 3.74-3.72 (m, 2H), 3.53-3.51 (m, 2H), 2.71-2.65 (m, 1H), 2.60-2.54 (m, 3H), 1.18 (t, J=7.0 Hz, 3H); MS(ESI) m/z: 496 [M+H]$^+$

[Example 48] Di-tert-butyl (3-((5-((4-carbamim-idoyl)-2-fluorophenoxy)carbonyl)thiazol-2-yl)(ethyl) amino)propanoyl)-D-glutamate

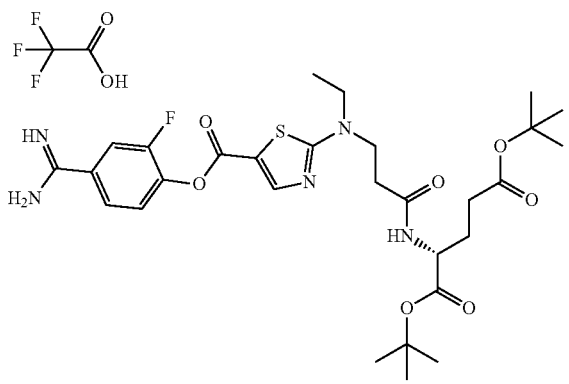

Reaction was carried out from the compound tert-butyl 2-bromothiazole-5-carboxylate obtained in [Preparation Example 2] in the same manner as in [Example 1] to give the title compound. (Yield: 44%)

1H NMR (400 MHz, TFA salt, Methanol-d$_4$) δ 8.10 (s, 1H), 7.77 (dd, J=2.0, 10.3 Hz, 1H), 7.71-7.69 (m, 1H), 7.58 (t, J=7.7 Hz, 1H), 4.31-4.28 (m, 1H), 3.87-3.86 (m, 2H), 3.61 (q, J=14.1 Hz, 2H), 2.68 (t, J=6.8 Hz, 2H), 2.29 (t, J=7.5 Hz, 2H), 2.10-2.01 (m, 1H), 1.88-1.78 (m, 1H), 1.46 (s, 9H), 1.44 (s, 9H), 1.27 (t, J=7.0 Hz, 3H); MS(ESI) m/z: 622 [M+H]$^+$

[Example 49] (3-((5-((4-Carbamimidoyl-2-fluoro-phenoxy)carbonyl)thiazol-2-yl)(ethyl)amino)pro-panoyl)-D-glutamic Acid

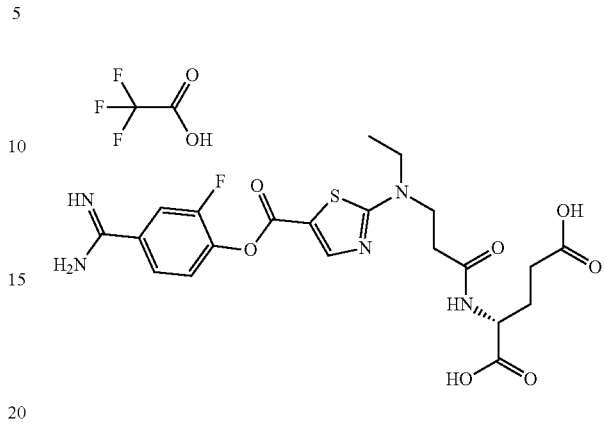

Reaction was carried out from the compound tert-butyl 2-bromothiazole-5-carboxylate obtained in [Preparation Example 2] in the same manner as in [Example 1] to give the title compound. (Yield: 30%)

1H NMR (400 MHz, TFA salt, Methanol-d$_4$) δ 8.10 (s, 1H), 7.77 (dd, J=2.0, 10.3 Hz, 1H), 7.71-7.69 (m, 1H), 7.58 (t, J=7.7 Hz, 1H), 4.31-4.28 (m, 1H), 3.87-3.86 (m, 2H), 3.61 (q, J=14.1 Hz, 2H), 2.68 (t, J=6.8 Hz, 2H), 2.29 (t, J=7.5 Hz, 2H), 2.10-2.01 (m, 1H), 1.88-1.78 (m, 1H), 1.46 (s, 9H), 1.44 (s, 9H), 1.27 (t, J=7.0 Hz, 3H); MS(ESI) m/z: 510 [M+H]$^+$

[Example 50] 4-Carbamimidoyl-2-fluorophenyl 2-(ethyl(3-((4-(methoxycarbonyl)phenyl)amino)-3-oxopropyl)amino)thiazole-5-carboxylate

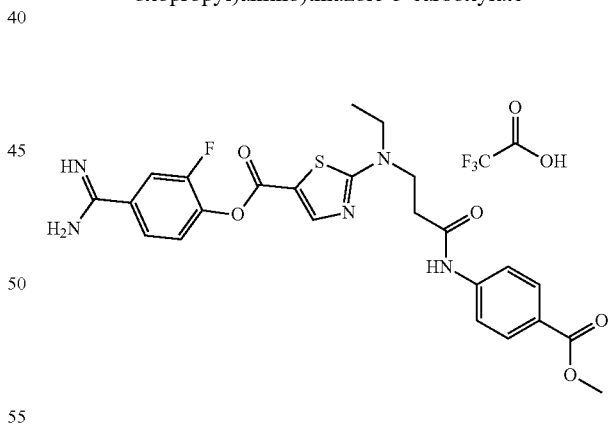

Reaction was carried out from the compound tert-butyl 2-bromothiazole-5-carboxylate obtained in [Preparation Example 2] in the same manner as in [Example 1] to give the title compound. (Yield: 20%)

1H NMR (400 MHz, TFA salt, Methanol-d$_4$) δ 8.12 (s, 1H), 7.98 (d, J=8.7 Hz, 2H), 7.80 (d, J=10.4 Hz, 1H), 7.73-7.69 (m, 2H), 7.62-7.58 (m, 1H), 3.99 (t, J=6.8 Hz, 2H), 3.90 (s, 3H), 3.70-3.65 (m, 2H), 2.87 (t, J=6.8 Hz, 2H), 1.33 (t, J=7.1 Hz, 3H); MS(ESI) m/z: 514 [M+H]$^+$

[Example 51] 4-Carbamimidoyl-2-fluorophenyl 2-(ethyl(3-((3-(methoxycarbonyl)phenyl)amino)-3-oxopropyl) amino)thiazole-5-carboxylate

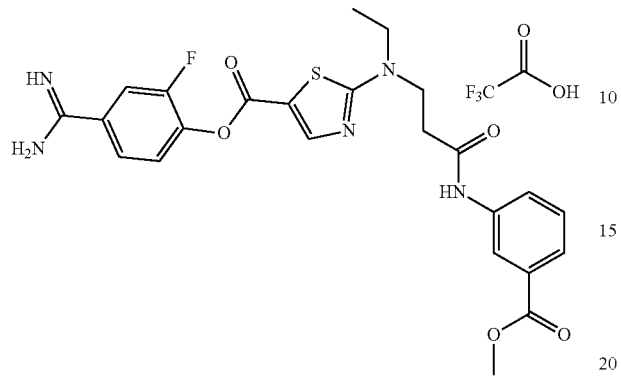

Reaction was carried out from the compound tert-butyl 2-bromothiazole-5-carboxylate obtained in [Preparation Example 2] in the same manner as in [Example 1] to give the title compound. (Yield: 25%)

1H NMR (400 MHz, TFA salt, Methanol-d$_4$) δ 8.26 (s, 1H), 8.24 (s, 1H), 8.12-7.71 (m, 4H), 7.62-7.58 (m, 1H), 7.44 (t, J=8.0 Hz, 1H), 3.99 (t, J=6.8 Hz, 2H), 3.92 (s, 3H), 3.70-3.65 (m, 2H), 2.85 (t, J=6.8 Hz, 2H), 1.33 (t, J=7.1 Hz, 3H); MS(ESI) m/z: 514 [M+H]$^+$

[Example 52] 4-Carbamimidoyl-2-fluorophenyl 2-((3-((4-(tert-butoxycarbonyl)phenyl)amino)-3-oxopropyl)(ethyl)amino)thiazole-5-carboxylate

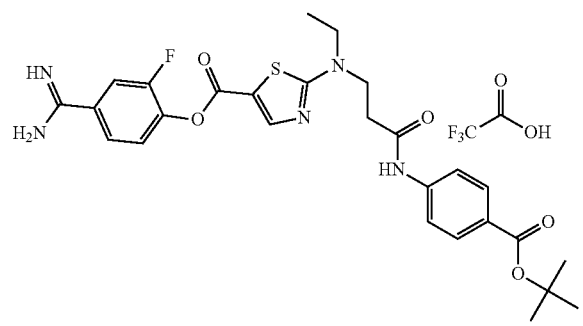

Reaction was carried out from the compound tert-butyl 2-bromothiazole-5-carboxylate obtained in [Preparation Example 2] in the same manner as in [Example 1] to give the title compound. (Yield: 59%)

1H NMR (400 MHz, TFA salt, DMSO-d6) δ 11.21 (s, 1H), 10.23 (br s, 2H), 10.00 (br s, 2H), 9.03 (s, 1H), 8.72 (d, J=10.1 Hz, 1H), 8.66 (d, J=8.7 Hz, 1H), 8.53-8.50 (m, 4H), 4.69-4.65 (m, 2H), 4.50-4.30 (m, 2H), 3.63 (t, J=6.8 Hz, 2H), 2.34 (s, 9H), 2.03 (t, J=7.1 Hz, 3H);

MS (ESI) m/z: 556 [M+H]$^+$

[Example 53] 4-Carbamimidoyl-2-fluorophenyl 2-((tert-butoxycarbonyl)phenyl)amino)-3-oxopropyl) (ethyl)amino)thiazole-5-carboxylate

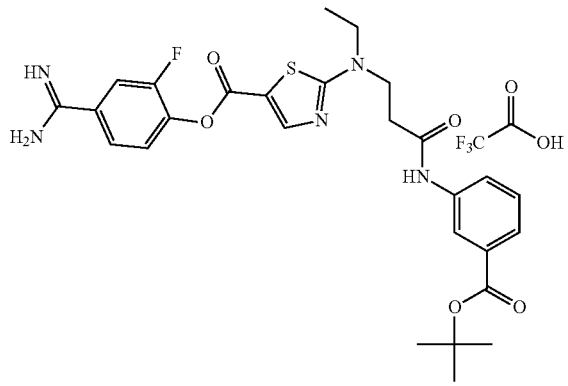

Reaction was carried out from the compound tert-butyl 2-bromothiazole-5-carboxylate obtained in [Preparation Example 2] in the same manner as in [Example 1] to give the title compound. (Yield: 62%)

1H NMR (400 MHz, TFA salt, Methanol-d$_4$) δ 8.03 (s, 1H), 8.02 (s, 1H), 7.71-7.67 (m, 2H), 7.62-7.58 (m, 2H), 7.48 (t, J=7.7 Hz, 1H), 7.29 (t, J=7.9 Hz, 1H), 3.88 (t, J=6.8 Hz, 2H), 3.58-3.53 (m, 2H), 2.73 (t, J=6.8 Hz, 2H), 1.49 (s, 9H), 1.21 (t, J=7.1 Hz, 3H); MS(ESI) m/z: 556 [M+H]$^+$

[Example 54] 3-(3-((5-((4-Carbamimidoyl-2-fluoro-phenoxy)carbonyl)thiazol-2-yl)(ethyl)amino)pro-panamido)benzoic Acid

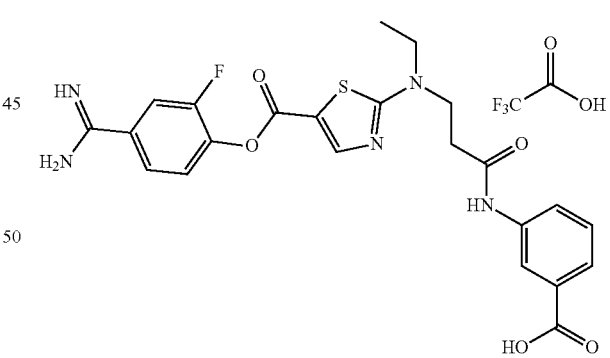

Reaction was carried out from the compound tert-butyl 2-bromothiazole-5-carboxylate obtained in [Preparation Example 2] in the same manner as in [Example 1] to give the title compound. (Yield: 23%)

1H NMR (400 MHz, TFA salt, Methanol-d$_4$) δ 8.23 (s, 1H), 8.13 (s, 1H), 7.84-7.71 (m, 4H), 7.60 (t, J=8.2 Hz, 1H), 7.43 (t, J=8.0 Hz, 1H), 3.99 (t, J=6.7 Hz, 2H), 3.71-3.65 (m, 2H), 2.86 (t, J=6.8 Hz, 2H), 1.33 (t, J=7.1 Hz, 3H); MS(ESI) m/z: 500 [M+H]$^+$

[Example 55] 4-(3-((5-((4-Carbamimidoyl-2-fluorophenoxy)carbonyl)thiazol-2-yl)(ethyl)amino)propanamido)benzoic Acid

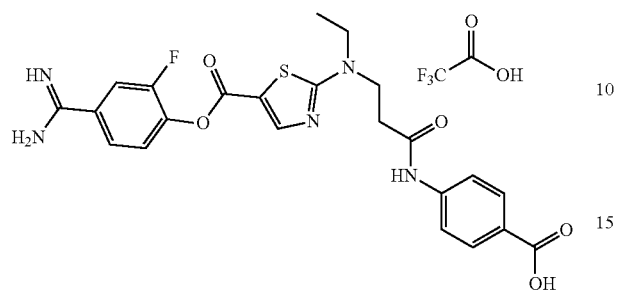

Reaction was carried out from the compound tert-butyl 2-bromothiazole-5-carboxylate obtained in [Preparation Example 2] in the same manner as in [Example 1] to give the title compound. (Yield: 20%)

1H NMR (400 MHz, TFA salt, Methanol-$d_4$) δ 8.12 (s, 1H), 7.99 (d, J=8.6 Hz, 2H), 7.82-7.78 (m, 1H), 7.73-7.69 (m, 3H), 7.60-7.58 (m, 1H), 3.99 (t, J=6.8 Hz, 2H), 3.69-3.65 (m, 2H), 2.87 (t, J=6.6 Hz, 2H), 1.33 (t, J=7.1 Hz, 3H); MS(ESI) m/z: 500 [M+H]$^+$

[Preparation Example 3] Tert-butyl 2-bromobenzo[d]thiazole-6-carboxylate

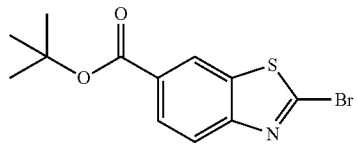

After 7.0 g (27.1 mmol) of 2-bromobenzo[d]thiazole-6-carboxylic acid was dissolved in 60 mL of tert-butanol and 30 mL of tetrahydrofuran, 7.48 mL (32.5 mmol) of di-tert-butyl dicarbonate, 0.663 g (5.42 mmol) of DMAP and 6.58 mL (81.0 mmol) of pyridine were added thereto at room temperature, and then stirred at 70° C. for 5 hours. The reaction mixture was concentrated under reduced pressure, ethyl acetate, water, and a 1 N aqueous hydrogen chloride solution were added until pH 6 was reached, then stirred for 1 hour, and the precipitated solid was filtered. The filtrate ethyl acetate and the aqueous layer were extracted and the organic layers were combined. The combined organic layers were dried again with sodium sulfate, concentrated under reduced pressure, and purified by MPLC to give 3.4 g (40%) of the target compound as a yellow solid.

MS (ESI) m/z 315 [M+H]$^+$

[Example 56] 3-((6-((4-Carbamimidoyl-2-fluorophenoxy)carbonyl)benzo[d]thiazol-2-yl)amino)-2,2-dimethylpropanoic Acid

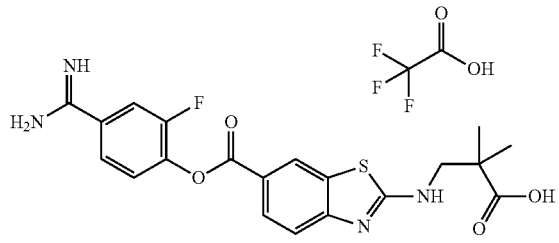

Step 1. Tert-butyl 2-((3-methoxy-2,2-dimethyl-3-oxopropyl)amino)benzo[d]thiazole-6-carboxylate

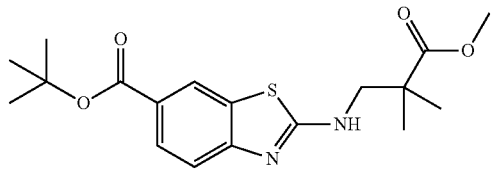

After 2.5 g (7.96 mmol) of the compound tert-butyl 2-bromobenzo[d]thiazole-6-carboxylate obtained in [Preparation Example 3] was dissolved in 30 mL of dimethylformamide, 1.39 g (8.35 mmol) of methyl 3-amino-2,2-dimethylpropanoate hydrochloride and 1.65 g (11.94 mmol) of potassium carbonate were added thereto at room temperature, and then stirred at 60° C. for 16 hours. After the reaction mixture was cooled to room temperature, it was extracted with ethyl acetate and brine, and the organic layers were combined. The combined organic layers were dried over sodium sulfate, concentrated under reduced pressure, and purified by MPLC to give 3.0 g (72%) of the target compound as a yellow solid.

MS (ESI) m/z: 365 [M+H]$^+$

Step 2. 2-((3-Methoxy-2,2-dimethyl-3-oxopropyl)amino)benzo[d]thiazole-6-carboxylic Acid

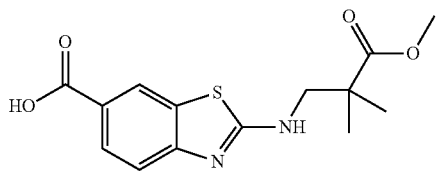

After 2.3 g (6.31 mmol) of the compound tert-butyl 2-((3-methoxy-2,2-dimethyl-3-oxopropyl)amino)benzo[d]thiazole-6-carboxylate obtained in step 1 was dissolved in 10 mL of dichloromethane, 5 mL (65.3 mmol) of trifluoroacetic acid was added thereto, and then stirred at room temperature for 1 hour. The reaction mixture was concentrated under reduced pressure to give 2.6 g (quant) of the target compound as a pale yellow liquid without purification.

MS (ESI) m/z: 309 [M+H]$^+$

Step 3. 4-Carbamidoyl-2-fluorophenyl 2-((3-methoxy-2,2-dimethyl-3-oxopropyl)amino)benzo[d]thiazole-6-carboxylate

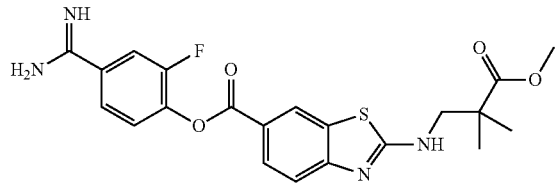

After 1.3 g (3.08 mmol) of the compound 2-((3-methoxy-2,2-dimethyl-3-oxopropyl)amino)benzo[d]thiazole-6-carboxylic acid obtained in step 2 was dissolved in 7 mL of pyridine, 0.65 g (3.39 mmol) of 3-fluoro-4-hydroxybenzimidamide hydrochloride and 1.06 g (5.54 mmol) of EDCI were added thereto, and then stirred at 50° C. for 4 hours. The reaction mixture was concentrated under reduced pressure and purified by prep-HPLC to give 0.8 g (59%) of the target compound as an ivory solid.

MS(ESI) m/z: 445 [M+H]$^+$

Step 4. 3-((6-((4-Carbamimidoyl-2-fluorophenoxy)carbonyl)benzo[d]thiazol-2-yl)amino)-2,2-dimethylpropanoic Acid

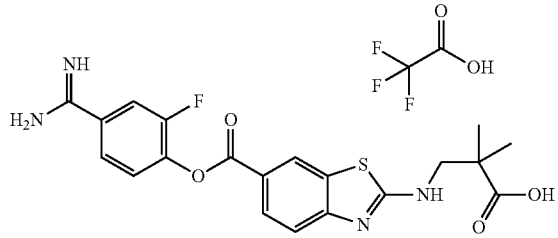

To 0.8 g (1.43 mmol) of the compound 4-carbamidoyl-2-fluorophenyl 2-((3-methoxy-2,2-dimethyl-3-oxopropyl)amino)benzo[d]thiazole-6-carboxylate obtained in step 3 was added 3 mL of HCL (4N in H$_2$O) and 3 mL of HCl (4N in dioxane), and then stirred at 40° C. for 3 hours. The reaction mixture was concentrated under reduced pressure and purified by prep-HPLC to give 0.6 g (77%) of the target compound as a white solid.

1H NMR (400 MHz, TLA salt, DMSO-d$_6$) δ 12.48 (br s, 1H), 9.43 (br s, 2H), 9.22 (br s, 2H), 8.57-8.52 (m, 2H), 7.99 (dd, J=1.8, 8.5 Hz, 1H), 7.96-7.91 (m, 1H), 7.79-7.73 (m, 2H), 7.51 (d, J=8.5 Hz, 1H), 3.63 (d, J=5.4 Hz, 2H), 1.18 (s, 6H); MS(ESI) m/z: 431 [M+H]$^+$

[Example 57] 4-Carbamimidoylphenyl 2-(4-(methoxycarbonyl)piperidin-1-yl)benzo[d]thiazole-6-carboxylate

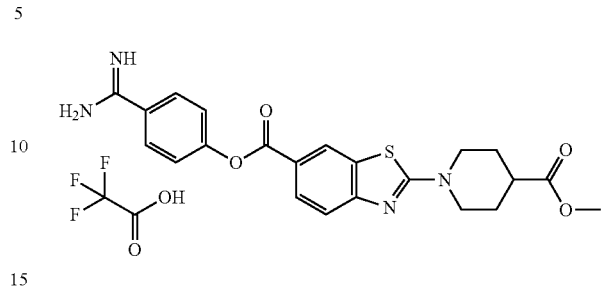

Reaction was carried out from the compound tert-butyl 2-bromobenzo[d]thiazole-6-carboxylate obtained in [Preparation Example 3] in the same manner as in [Example 56] to give the title compound. (Yield: 5%)

1H NMR (400 MHz, TFA salt, DMSO-d$_6$) δ 9.34 (br s, 2H), 9.04 (br s, 2H), 8.61 (d, J=1.8 Hz, 1H), 8.03 (dd, J=1.8, 8.5 Hz, 1H), 7.90 (d, J=8.7 Hz, 2H) 7.58-7.54 (m, 3H), 4.04 (d, J=12.8 Hz, 2H), 3.63 (s, 3H), 3.39-3.38 (m, 2H), 2.78-2.70 (m, 1H), 2.00 (dd, J=3.2, 13.4 Hz, 2H), 1.70-1.61 (m, 2H); MS(ESI) m/z: 439 [M+H]$^+$

[Example 58] 1-(6-((4-Carbamimidoylphenoxy)carbonyl)benzo[d]thiazol-2-yl)piperidine-4-carboxylic Acid

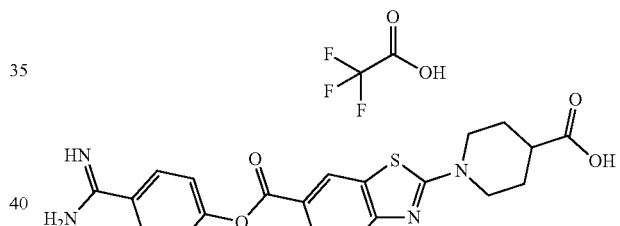

Reaction was carried out from the compound tert-butyl 2-bromobenzo[d]thiazole-6-carboxylate obtained in [Preparation Example 3] in the same manner as in [Example 56] to give the title compound. (Yield: 10%)

MS(ESI) m/z: 425 [M+H]$^+$

[Example 59] 4-Carbamimidoylphenyl 2-((3-methoxy-3-oxopropyl)amino)benzo[d]thiazole-6-carboxylate

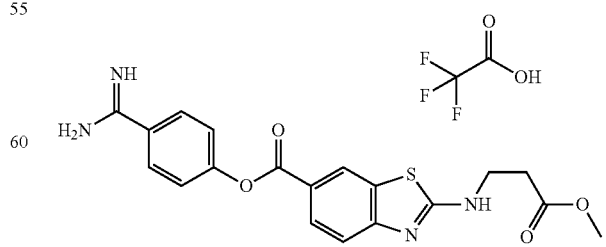

Reaction was carried out from the compound tert-butyl 2-bromobenzo[d]thiazole-6-carboxylate obtained in [Preparation Example 3] in the same manner as in [Example 56] to give the title compound. (Yield: 40%)

1H NMR (400 MHz, TFA salt, DMSO-$d_6$) δ 9.35 (br s, 2H), 9.04 (br s, 2H), 8.68 (t, J=5.0 Hz, 1H), 8.53 (s, 1H), 8.01 (d, J=8.4 Hz, 1H), 7.91 (d, J=8.6 Hz, 2H), 7.58 (d, J=8.6 Hz, 2H), 7.53 (d, J=8.4 Hz, 1H), 3.69-3.63 (m, 2H), 3.63 (s, 3H), 2.71 (t, J=6.5 Hz, 1H); MS(ESI) m/z: 399 [M+H]$^+$

[Example 60] 4-Carbamimidoylphenyl 2-((3-methoxy-3-oxopropyl)(methyl)amino)benzo[d]thiazole-6-carboxylate

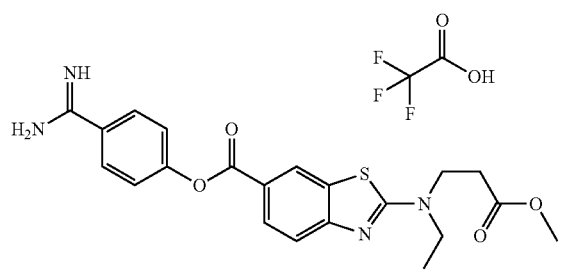

Reaction was carried out from the compound tert-butyl 2-bromobenzo[d]thiazole-6-carboxylate obtained in [Preparation Example 3] in the same manner as in [Example 56] to give the title compound. (Yield: 27%)

1H NMR (400 MHz, TFA salt, DMSO-$d_6$) δ 9.34 (br s, 2H), 9.03 (br s, 2H), 8.63 (d, J=1.8 Hz, 1H), 8.04 (dd, J=1.8, 8.5 Hz, 1H), 7.91 (d, J=8.7 Hz, 2H), 7.58 (d, J=8.6 Hz, 3H), 3.87 (t, J=8.0 Hz, 2H), 3.61 (s, 3H), 3.19 (s, 3H), 2.78 (t, J=7.0 Hz, 2H); MS(ESI) m/z: 413 [M+H]$^+$

[Example 61] 4-Carbamimidoylphenyl 2-(ethyl(3-methoxy-3-oxopropyl)amino)benzo[d]thiazole-6-carboxylate

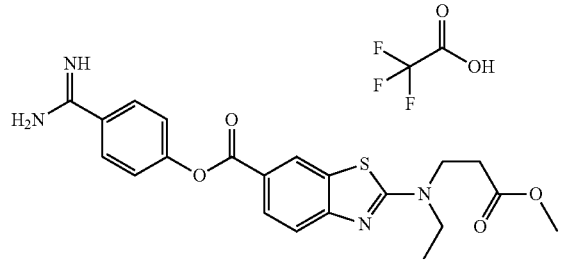

Reaction was carried out from the compound tert-butyl 2-bromobenzo[d]thiazole-6-carboxylate obtained in [Preparation Example 3] in the same manner as in [Example 56] to give the title compound. (Yield: 33%)

1H NMR (400 MHz, TFA salt, DMSO-$d_6$) δ 9.35 (br s, 2H), 9.11 (br s, 2H), 8.61 (s, 1H), 8.04 (d, J=8.6 Hz, 1H), 7.91 (d, J=8.4 Hz, 2H), 7.58 (d, J=7.4 Hz, 3H), 3.84 (t, J=6.6 Hz, 2H), 3.62 (s, 3H), 3.61-3.55 (m, 2H), 2.79 (t, J=7.0 Hz, 2H), 1.23 (t, J=7.0 Hz, 3H); MS(ESI) m/z: 427 [M+H]$^+$

[Example 62] 3-((6-((4-Carbamimidoylphenoxy)carbonyl)benzo[d]thiazol-2-yl)(methyl)amino)propanoic Acid

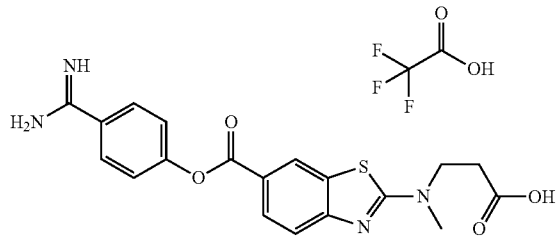

Reaction was carried out from the compound tert-butyl 2-bromobenzo[d]thiazole-6-carboxylate obtained in [Preparation Example 3] in the same manner as in [Example 56] to give the title compound. (Yield: 34%)

1H NMR (400 MHz, TFA salt, DMSO-$d_6$) δ 9.35 (br s, 2H), 9.01 (br s, 2H), 8.62 (s, 1H), 8.04 (d, J=8.4 Hz, 1H), 7.91 (d, J=8.6 Hz, 2H), 7.58 (d, J=8.6 Hz, 3H), 3.86-3.79 (m, 2H), 3.20 (s, 3H), 2.69 (t, J=7.2 Hz, 2H); MS(ESI) m/z: 399 [M+H]$^+$

[Example 63] 4-Carbamimidoylphenyl 2-((4-methoxy-4-oxobutyl)(methyl)amino)benzo[d]thiazole-6-carboxylate

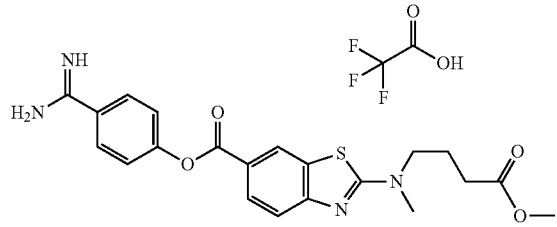

Reaction was carried out from the compound tert-butyl 2-bromobenzo[d]thiazole-6-carboxylate obtained in [Preparation Example 3] in the same manner as in [Example 56] to give the title compound. (Yield: 16%)

1H NMR (400 MHz, TFA salt, DMSO-$d_6$) δ 9.35 (br s, 2H), 9.03 (br s, 2H), 8.61 (d, J=1.8 Hz, 1H), 8.03 (dd, J=1.9, 8.5 Hz, 1H), 7.91 (d, J=8.6 Hz, 2H), 7.58 (d, J=8.7 Hz, 2H), 7.55 (d, J=8.6 Hz, 1H), 3.66-3.60 (m, 2H), 3.58 (s, 3H), 3.18 (s, 3H), 2.40 (t, J=7.2 Hz, 2H), 1.97-1.89 (m, 2H); MS(ESI) m/z: 427 [M+H]$^+$

[Example 64] 4-((6-((4-Carbamimidoylphenoxy)carbonyl)benzo[d]thiazol-2-yl)(methyl)amino)butanoic Acid

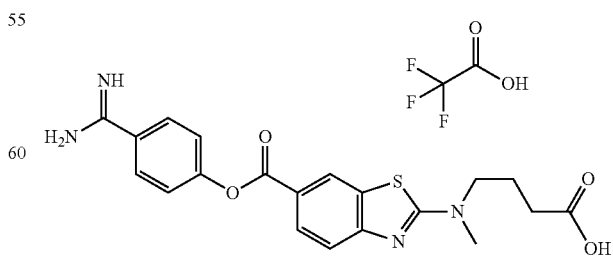

Reaction was carried out from the compound tert-butyl 2-bromobenzo[d]thiazole-6-carboxylate obtained in [Preparation Example 3] in the same manner as in [Example 56] to give the title compound. (Yield: 58%)

1H NMR (400 MHz, TFA salt, DMSO-$d_6$) δ 12.16 (br s, 1H), 9.35 (br s, 2H), 9.11 (br s, 2H), 8.60 (d, J=1.8 Hz, 1H), 8.03 (dd, J=1.8, 8.5 Hz, 1H), 7.91 (d, J=8.6 Hz, 2H), 7.60-7.54 (m, 3H), 3.66-3.58 (m, 2H), 3.19 (s, 3H), 2.31 (t, J=7.2 Hz, 2H), 1.94-1.86 (m, 2H); MS(ESI) m/z: 413 [M+H]$^+$

[Example 65] 3-((6-((4-Carbamimidoylphenoxy)carbonyl)benzo[d]thiazol-2-yl)amino)propanoic Acid

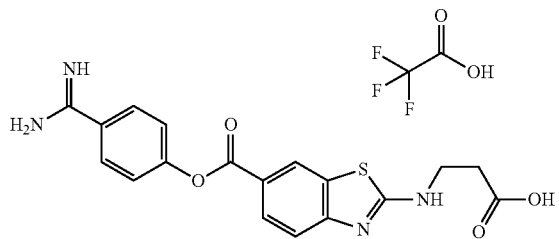

Reaction was carried out from the compound tert-butyl 2-bromobenzo[d]thiazole-6-carboxylate obtained in [Preparation Example 3] in the same manner as in [Example 56] to give the title compound. (Yield: 40%)

1H NMR (400 MHz, TFA salt, DMSO-$d_6$) δ 12.38 (br s, 1H), 9.35 (br s, 2H), 9.09 (br s, 2H), 8.65 (br s, 1H), 8.52 (s, 1H), 8.00 (dd, J=1.7, 8.5 Hz, 1H), 7.91 (d, J=8.6 Hz, 2H), 7.57 (d, J=8.6 Hz, 2H), 7.53 (d, J=8.5 Hz, 1H), 3.66-3.59 (m, 2H), 2.63 (t, J=6.4 Hz, 2H); MS(ESI) m/z: 385 [M+H]$^+$

[Example 66] 3-((6-((4-Carbamimidoylphenoxy)carbonyl)benzo[d]thiazol-2-yl)(ethyl)amino)propanoic Acid

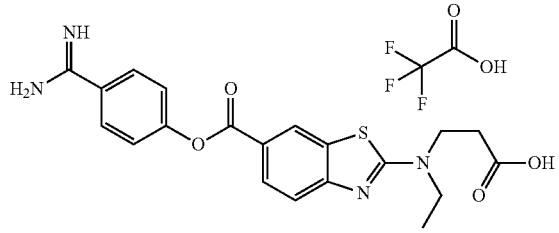

Reaction was carried out from the compound tert-butyl 2-bromobenzo[d]thiazole-6-carboxylate obtained in [Preparation Example 3] in the same manner as in [Example 56] to give the title compound. (Yield: 48%)

1H NMR (400 MHz, TFA salt, DMSO-$d_6$) δ 12.48 (br s, 1H), 9.34 (br s, 2H), 8.93 (br s, 2H), 8.61 (d, J=1.8 Hz, 1H), 8.03 (dd, J=1.8, 8.5 Hz, 1H), 7.91 (d, J=8.7 Hz, 2H), 7.58 (dd, J=2.1, 8.7 Hz, 1H), 3.82-3.76 (m, 2H), 3.65-3.57 (m, 2H), 2.71 (t, J=7.1 Hz, 2H), 1.24 (t, J=7.0 Hz, 3H); MS(ESI) m/z: 413 [M+H]$^+$

[Example 67] 4-Carbamimidoylphenyl 2-((3-methoxy-2,2-dimethyl-3-oxopropyl)amino)benzo[d]thiazole-6-carboxylate

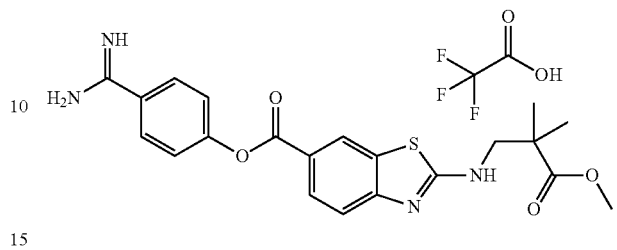

Reaction was carried out from the compound tert-butyl 2-bromobenzo[d]thiazole-6-carboxylate obtained in [Preparation Example 3] in the same manner as in [Example 56] to give the title compound. (Yield: 49%)

1H NMR (400 MHz, TFA salt, DMSO-$d_6$) δ 9.35 (br s, 2H), 9.05 (br s, 2H), 8.57-8.50 (m, 2H), 7.99 (d, J=8.5 Hz, 1H), 7.91 (d, J=8.6 Hz, 2H), 7.57 (d, J=8.6 Hz, 2H), 7.50 (d, J=8.4 Hz, 1H), 3.66-3.63 (m, 2H), 3.60 (s, 3H), 1.20 (s, 6H); MS(ESI) m/z: 427 [M+H]$^+$

[Example 68] 4-Carbamimidoylphenyl 2-((3-methoxy-2,2-dimethyl-3-oxopropyl)(methyl)amino)benzo[d]thiazole-6-carboxylate

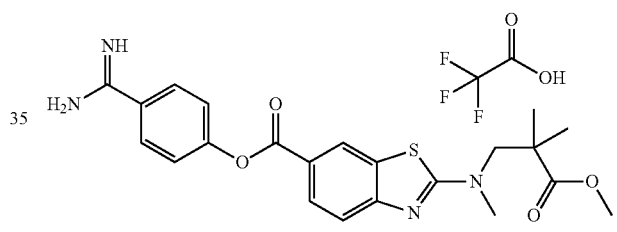

Reaction was carried out from the compound tert-butyl 2-bromobenzo[d]thiazole-6-carboxylate obtained in [Preparation Example 3] in the same manner as in [Example 56] to give the title compound. (Yield: 15%)

1H NMR (400 MHz, TFA salt, DMSO-$d_6$) δ 9.35 (br s, 2H), 9.01 (br s, 2H), 8.63 (d, J=1.7 Hz, 1H), 8.04 (dd, J=1.8, 8.6 Hz, 1H), 7.91 (d, J=8.7 Hz, 2H), 7.59-7.55 (m, 3H), 3.86 (s, 2H), 3.60 (s, 3H), 3.16 (s, 3H), 1.22 (s, 6H); MS(ESI) m/z: 441 [M+H]$^+$

[Example 69] 4-Carbamimidoylphenyl 2-(ethyl(3-methoxy-2,2-dimethyl-3-oxopropyl)amino)benzo[d]thiazole-6-carboxylate

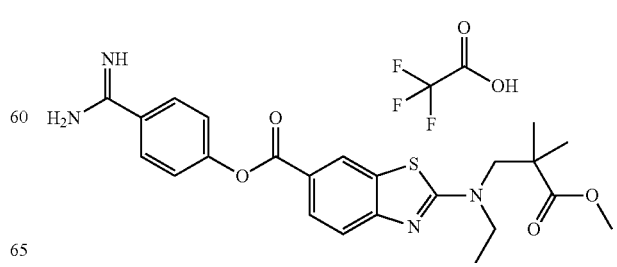

Reaction was carried out from the compound tert-butyl 2-bromobenzo[d]thiazole-6-carboxylate obtained in [Preparation Example 3] in the same manner as in [Example 56] to give the title compound. (Yield: 19%)

1H NMR (400 MHz, TFA salt, DMSO-$d_6$) δ 9.35 (br s, 2H), 9.04 (br s, 2H), 8.61 (s, 1H), 8.03 (d, J=8.8 Hz, 1H), 7.91 (d, J=8.5 Hz, 2H), 7.59-7.54 (m, 3H), 3.82 (s, 2H), 3.61 (s, 3H), 3.54-3.47 (m, 2H), 1.23 (s, 6H), 1.22-1.17 (m, 3H); MS(ESI) m/z: 455 [M+H]$^+$

[Example 70] 4-Carbamimidoyl-2-fluorophenyl 2-(ethyl(3-methoxy-2,2-dimethyl-3-oxopropyl)amino)benzo[d]thiazole-6-carboxylate

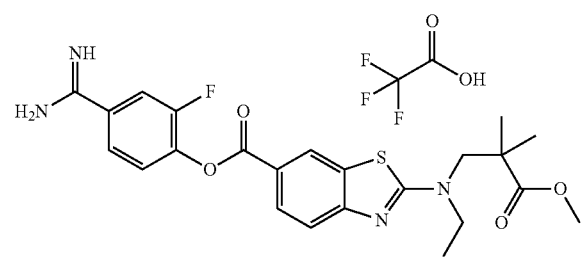

Reaction was carried out from the compound tert-butyl 2-bromobenzo[d]thiazole-6-carboxylate obtained in [Preparation Example 3] in the same manner as in [Example 56] to give the title compound. (Yield: 21%)

1H NMR (400 MHz, TFA salt, DMSO-$d_6$) δ 9.43 (br s, 2H), 9.16 (br s, 2H), 8.63 (s, J=1.4 Hz, 1H), 8.05-8.02 (m, 1H), 7.94 (d, J=10.4 Hz, 1H), 7.80-7.75 (m, 2H), 7.56 (d, J=8.5 Hz, 1H), 3.82 (s, 2H), 3.61 (s, 3H), 3.54-3.48 (m, 2H), 1.22 (s, 6H), 1.22-1.17 (m, 3H);

MS(ESI) m/z: 473 [M+H]+

[Example 71] 4-Carbamimidoyl-2-fluorophenyl 2-((4-methoxy-4-oxobutyl)(methyl)amino)benzo[d]thiazole-6-carboxylate

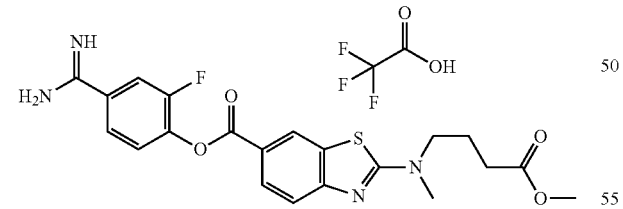

Reaction was carried out from the compound tert-butyl 2-bromobenzo[d]thiazole-6-carboxylate obtained in [Preparation Example 3] in the same manner as in [Example 56] to give the title compound. (Yield: 18%)

1H NMR (400 MHz, TFA salt, DMSO-$d_6$) δ 9.42 (br s, 2H), 9.11 (br s, 2H), 8.63 (d, J=1.8 Hz, 1H), 8.03 (dd, J=1.9, 8.5 Hz, 1H), 7.96-7.91 (m, 1H), 7.80-7.73 (m, 2H), 7.56 (d, J=8.6 Hz, 1H), 3.67-3.61 (m, 2H), 3.58 (s, 3H), 3.18 (s, 3H), 2.40 (t, J=7.2 Hz, 2H), 1.97-1.89 (m, 2H); MS(ESI) m/z: 445 [M+H]$^+$

[Example 72] 4-Carbamimidoyl-2-fluorophenyl 2-((3-methoxy-3-oxopropyl)(methyl)amino)benzo[d]thiazole-6-carboxylate

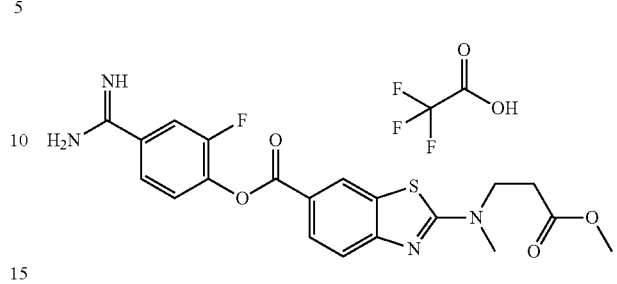

Reaction was carried out from the compound tert-butyl 2-bromobenzo[d]thiazole-6-carboxylate obtained in [Preparation Example 3] in the same manner as in [Example 56] to give the title compound. (Yield: 16%)

1H NMR (400 MHz, TFA salt, DMSO-$d_6$) δ 9.43 (br s, 2H), 9.24 (br s, 2H), 8.65 (d, J=1.8 Hz, 1H), 8.04 (dd, J=1.8, 8.5 Hz, 1H), 7.96-7.92 (m, 1H), 7.80-7.73 (m, 2H), 7.59 (d, J=8.6 Hz, 1H), 3.90-3.84 (m, 2H), 3.61 (s, 3H), 3.19 (s, 3H), 2.77 (t, J=7.0 Hz, 2H); MS(ESI) m/z: 431 [M+H]$^+$

[Example 73] 3-((6-((4-Carbamimidoylphenoxy)carbonyl)benzo[d]thiazol-2-yl)amino)-2,2-dimethylpropanoic Acid

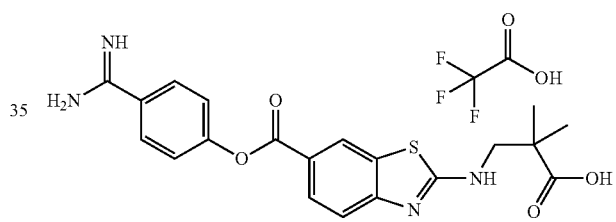

Reaction was carried out from the compound tert-butyl 2-bromobenzo[d]thiazole-6-carboxylate obtained in [Preparation Example 3] in the same manner as in [Example 56] to give the title compound. (Yield: 42%)

1H NMR (400 MHz, TFA salt, DMSO-$d_6$) δ 12.46 (br s, 1H), 9.35 (br s, 2H), 9.05 (br s, 2H), 8.53-8.48 (m, 2H), 7.99 (dd, J=1.8, 8.5 Hz, 1H), 7.91 (d, J=8.7 Hz, 2H), 7.57 (d, J=8.7 Hz, 2H), 7.50 (d, J=8.5 Hz, 1H), 3.63 (d, J=5.6 Hz, 2H), 1.18 (s, 6H); MS(ESI) m/z: 413 [M+H]$^+$

[Example 74] 3-((6-((4-Carbamimidoylphenoxy)carbonyl)benzo[d]thiazol-2-yl)(ethyl) Amino)-2,2-dimethylpropanoic Acid

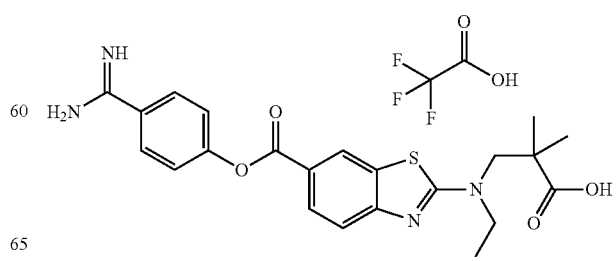

Reaction was carried out from the compound tert-butyl 2-bromobenzo[d]thiazole-6-carboxylate obtained in [Preparation Example 3] in the same manner as in [Example 56] to give the title compound. (Yield: 38%)

1H NMR (400 MHz, TFA salt, DMSO-$d_6$) δ 12.70 (br s, 1H), 9.36 (br s, 2H), 9.21 (br s, 2H), 8.60 (d, J=1.8 Hz, 1H), 8.03 (dd, J=1.8, 8.5 Hz, 1H), 7.92 (d, J=8.6 Hz, 2H), 7.60-7.55 (m, 3H), 3.82 (s, 2H), 3.60-3.53 (m, 2H), 1.24-1.18 (m, 9H); MS(ESI) m/z: 441 [M+H]$^+$

[Example 75] 3-((6-((4-Carbamimidoyl-2-fluorophenoxy)carbonyl)benzo[d]thiazol-2-yl)(ethyl)amino)-2,2-dimethyl Propanoic Acid

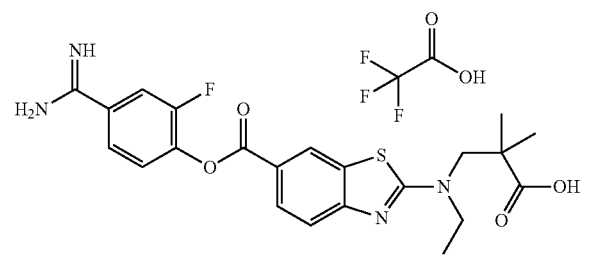

Reaction was carried out from the compound tert-butyl 2-bromobenzo[d]thiazole-6-carboxylate obtained in [Preparation Example 3] in the same manner as in [Example 56] to give the title compound. (Yield: 41%)

1H NMR (400 MHz, TFA salt, DMSO-$d_6$) δ 12.71 (br s, 1H), 9.43 (br s, 2H), 9.22 (br s, 2H), 8.63 (d, J=1.8 Hz, 1H), 8.04 (dd, J=1.8, 8.6 Hz, 1H), 7.97-7.92 (m, 1H), 7.80-7.73 (m, 2H), 7.58 (d, J=8.5 Hz, 1H), 3.83 (s, 2H), 3.60-3.52 (m, 2H), 1.24-1.18 (m, 9H); MS(ESI) m/z: 459 [M+H]$^+$

[Example 76] 4-((6-((4-Carbamimidoyl-2-fluorophenoxy)carbonyl)benzo[d]thiazol-2-yl)(methyl)amino)butanoic Acid

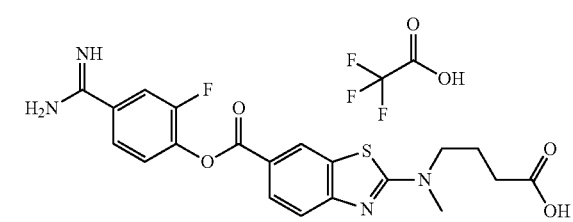

Reaction was carried out from the compound tert-butyl 2-bromobenzo[d]thiazole-6-carboxylate obtained in [Preparation Example 3] in the same manner as in [Example 56] to give the title compound. (Yield: 30%)

1H NMR (400 MHz, TFA salt, DMSO-$d_6$) δ 12.19 (br s, 1H), 9.43 (br s, 2H), 9.22 (br s, 2H), 8.63 (d, J=1.8 Hz, 1H), 8.03 (dd, J=1.9, 8.5 Hz, 1H), 7.96-7.92 (m, 1H), 7.80-7.73 (m, 2H), 7.56 (d, J=8.5 Hz, 1H), 3.66-3.58 (m, 2H), 3.19 (s, 3H), 2.31 (t, J=7.3 Hz, 2H), 1.90 (p, J=7.2, 14.4 Hz, 2H); MS(ESI) m/z: 431 [M+H]$^+$

[Example 77] 3-((6-((4-Carbamimidoyl-2-fluorophenoxy)carbonyl)benzo[d]thiazol-2-yl)(methyl)Amino)propanoic Acid

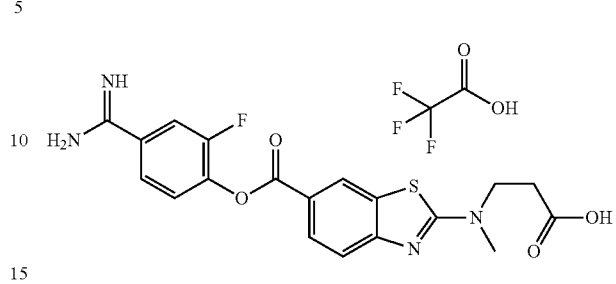

Reaction was carried out from the compound tert-butyl 2-bromobenzo[d]thiazole-6-carboxylate obtained in [Preparation Example 3] in the same manner as in [Example 56] to give the title compound. (Yield: 34%)

1H NMR (400 MHz, TFA salt, DMSO-$d_6$) δ 12.47 (br s, 1H), 9.43 (br s, 2H), 9.23 (br s, 2H), 8.65 (d, J=1.8 Hz, 1H), 8.04 (dd, J=1.9, 8.5 Hz, 1H), 7.96-7.92 (m, 1H), 7.80-7.73 (m, 2H), 7.59 (d, J=8.5 Hz, 1H), 3.86-3.79 (m, 2H), 3.20 (s, 3H), 2.69 (t, J=7.2 Hz, 2H); MS(ESI) m/z: 417 [M+H]$^+$

[Example 78] 4-Carbamimidoyl-2-fluorophenyl 2-(4-(methoxycarbonyl piperidin-1-yl)benzo[d]thiazole-6-carboxylate

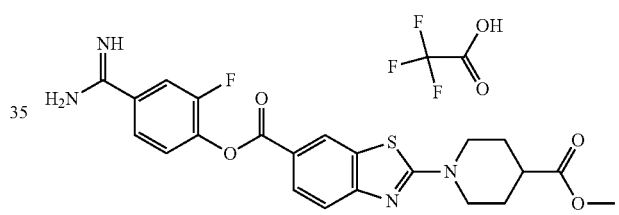

Reaction was carried out from the compound tert-butyl 2-bromobenzo[d]thiazole-6-carboxylate obtained in [Preparation Example 3] in the same manner as in [Example 56] to give the title compound. (Yield: 53%)

1H NMR (400 MHz, TFA salt, DMSO-$d_6$) δ 11.30 (br s, 1H), 10.93 (br s, 2H), 8.61 (d, J 5=1.8 Hz, 1H), 8.04 (dd, J=1.4, 8.5 Hz, 1H), 7.96 (dd, J=2.0, 11.9 Hz, 1H), 7.76 (d, J=7.7 Hz, 1H), 7.54 (d, J=8.5 Hz, 1H), 7.16 (t, J=8.6 Hz, 1H), 4.04 (d, J=12.8 Hz, 2H), 3.63 (s, 3H), 3.36-3.33 (m, 2H), 2.78-2.71 (m, 1H), 2.02-1.98 (m, 2H), 1.70-1.60 (m, 2H); MS(ESI) m/z: 457 [M+H]$^+$

[Example 79] 1-(6-((4-Carbamimidoyl-2-fluorophenoxy)carbonyl)benzo[d]thiazol-2-yl)piperidine-4-carboxylic Acid

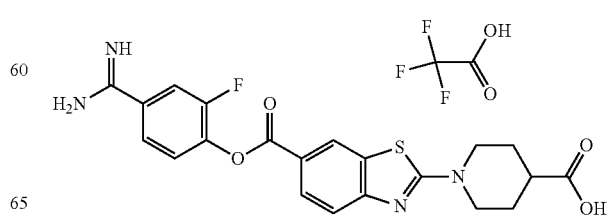

Reaction was carried out from the compound tert-butyl 2-bromobenzo[d]thiazole-6-carboxylate obtained in [Preparation Example 3] in the same manner as in [Example 56] to give the title compound. (Yield: 33%)

1H NMR (400 MHz, TFA salt, DMSO-d$_6$) δ 11.29 (br s, 1H), 10.97 (br s, 2H), 8.61 (d, J=1.7 Hz, 1H), 8.04 (d, J=8.6 Hz, 1H), 7.83 (d, J=1.8 Hz, 1H), 7.81-7.76 (m, 1H), 7.54 (d, J=8.5 Hz, 1H), 7.14 (t, J=8.6 Hz, 1H), 4.04 (d, J=12.1 Hz, 2H), 3.38-3.32 (m, 2H), 2.64-2.58 (m, 1H), 2.00-1.96 (m, 2H), 1.68-1.58 (m, 2H); MS(ESI) m/z: 443 [M+H]$^+$

[Example 80] 4-Carbamimidoylphenyl 2-(4-(phenylcarbamoyl)piperidin-1-yl)benzo[d]thiazole-6-carboxylate

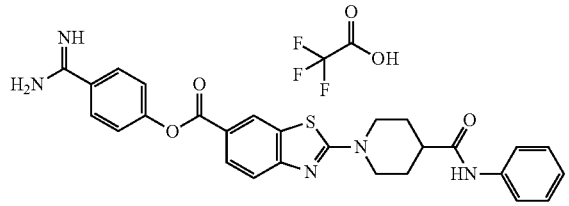

Reaction was carried out from the compound tert-butyl 2-bromobenzo[d]thiazole-6-carboxylate obtained in [Preparation Example 3] in the same manner as in [Example 56] to give the title compound. (Yield: 70%)

1H NMR (400 MHz, TFA salt, Methanol-d$_4$) δ 8.43 (s, 1H), 8.04 (d, J=8.6 Hz, 1H), 7.82 (d, J=8.6 Hz, 2H), 7.47-7.42 (m, 5H), 7.22 (t, J=7.9 Hz, 2H), 7.00 (t, J=7.4 Hz, 1H), 4.24-4.14 (m, 2H), 3.33-3.23 (m, 2H), 2.70-2.60 (m, 1H), 1.99-1.88 (m, 2H), 1.89-1.75 (m, 2H);

MS(ESI) m/z: 500 [M+H]$^+$

[Example 81] 4-Carbamimidoyl-2-fluorophenyl 2-(4-(phenylcarbamoyl)piperidin-1-yl)benzo [d]thiazole-6-carboxylate

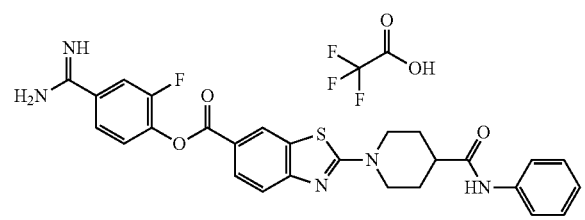

Reaction was carried out from the compound tert-butyl 2-bromobenzo[d]thiazole-6-carboxylate obtained in [Preparation Example 3] in the same manner as in [Example 56] to give the title compound. (Yield: 8%)

1H NMR (400 MHz, TFA salt, Methanol-d$_4$) δ 8.36 (s, 1H), 7.94 (d, J=8.6 Hz, 1H), 7.73 (d, J=9.0 Hz, 1H), 7.61 (d, J=8.6 Hz, 1H), 7.42-7.47 (m, 3H), 7.20 (t, J=7.6 Hz, 2H), 7.10 (t, J=6.4 Hz, 1H), 6.99 (t, J=7.4 Hz, 1H), 4.20 (m, 2H), 3.30 (m, 2H), 2.67 (m, 1H), 1.94 (m, 2H), 1.84 (m, 2H); MS(ESI) m/z: 518 [M+H]$^+$

[Example 82] 4-Carbamimidoyl-2-fluorophenyl 2-(4-benzoamidopiperidin-1-yl)benzo[d]thiazole-6-carboxylate

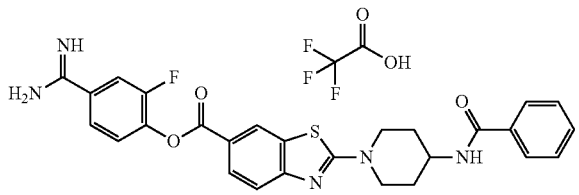

Reaction was carried out from the compound tert-butyl 2-bromobenzo[d]thiazole-6-carboxylate obtained in [Preparation Example 3] in the same manner as in [Example 56] to give the title compound. (Yield: 29%)

1H NMR (400 MHz, TFA salt, DMSO-d$_6$) δ 9.40 (br, 2H), 9.14 (br, 2H), 8.65 (d, 1.8 Hz, 1H), 8.36 (d, J=7.7 Hz, 1H), 8.07-8.04 (m, 1H), 7.96-7.93 (m, 1H), 7.86-7.84 (m, 2H), 7.80-7.74 (m, 2H), 7.59 (d, 8.56 Hz, 1H), 7.55-7.51 (m, 1H), 7.48-7.44 (m, 2H), 4.18-4.14 (m, 3H), 3.46-3.40 (m, 2H), 2.01-1.98 (m, 2H), 1.73-1.63 (m, 2H); MS(ESI) m/z: 518 [M+H]$^+$

[Example 83] 4-Carbamimidoylphenyl 2-(4-benzoamidopiperidin-1-yl)benzo[d]thiazole-6-carboxylate

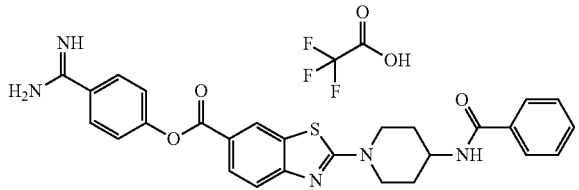

Reaction was carried out from the compound tert-butyl 2-bromobenzo[d]thiazole-6-carboxylate obtained in [Preparation Example 3] in the same manner as in [Example 56] to give the title compound. (Yield: 4%)

1H NMR (400 MHz, TFA salt, DMSO-d$_6$) δ 9.35 (s, 2H), 9.06 (s, 2H), 8.63-8.63 (d, 1H), 8.36-8.34 (s, J=7.7 Hz, 1H), 8.06-8.04 (d, J=8 Hz, 1H), 7.93-7.91 (d, J=8.6 Hz, 2H), 7.86-7.84 (d, J=7.2 Hz, 2H), 7.59-7.57 (d, J=8.6 Hz, 3H), 7.53-7.51 (d, J=7.2 Hz, 1H), 7.48-7.44 (t, 2H), 4.15-4.13 (d, 3H), 3.45-3.39 (t, 2H), 2.00-1.97 (d, J=12 Hz, 2H), 1.73-1.63 (m, 2H);

MS (ESI) m/z: 500 [M+H]$^+$

[Example 84] 4-Carbamimidoyl-2-fluorophenyl 2-(ethyl(3-methoxy-3-oxopropyl)amino)benzo[d]thiazole-6-carboxylate

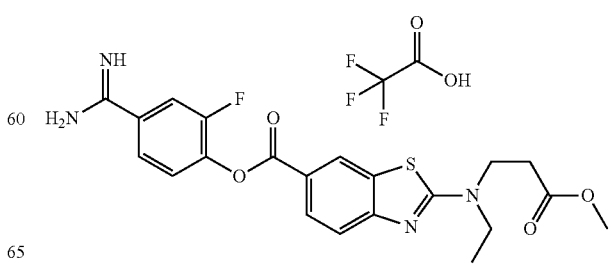

Reaction was carried out from the compound tert-butyl 2-bromobenzo[d]thiazole-6-carboxylate obtained in [Preparation Example 3] in the same manner as in [Example 56] to give the title compound. (Yield: 50%)

1H NMR (400 MHz, TFA salt, DMSO-$d_6$) δ 9.42 (br s, 2H), 9.20 (br s, 2H), 8.64 (d, J=1.8 Hz, 1H), 8.04 (dd, J=1.8, 8.5 Hz, 1H), 7.96-7.91 (m, 1H), 7.80-7.73 (m, 2H), 7.58 (d, J=8.6 Hz, 1H), 3.84 (t, J=6.9 Hz, 2H), 3.62 (s, 3H), 3.62-3.54 (m, 2H), 2.79 (t, J=7.1 Hz, 2H), 2.23 (t, J=7.1 Hz, 3H); MS(ESI) m/z: 445 [M+H]$^+$

[Example 85] 3-((6-((4-Carbamimidoyl-2-fluorophenoxy)carbonyl)benzo[d]thiazol-2-yl)(ethyl)amino)propanoic Acid

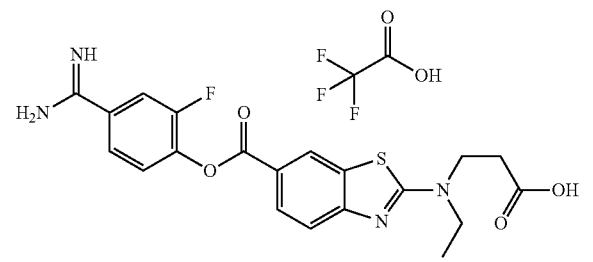

Reaction was carried out from the compound tert-butyl 2-bromobenzo[d]thiazole-6-carboxylate obtained in [Preparation Example 3] in the same manner as in [Example 56] to give the title compound. (Yield: 64%)

1H NMR (400 MHz, TFA salt, DMSO-$d_6$) δ 9.43 (br s, 2H), 9.33 (br s, 2H), 8.63 (s, 1H), 8.07-8.01 (m, 1H), 7.97-7.91 (m, 1H), 7.80-7.73 (m, 2H), 7.58 (d, J=8.5 Hz, 1H), 3.81-3.77 (m, 2H), 3.63-3.58 (m, 2H), 2.71 (t, J=7.1 Hz, 2H), 1.24 (t, J=7.0 Hz, 3H); MS(ESI) m/z: 431 [M+H]$^+$

[Example 86] 3-((6-((4-Carbamimidoylphenoxy)carbonyl)benzo[d]thiazol-2-yl)(methyl)amino)-2,2-dimethylpropanoic Acid

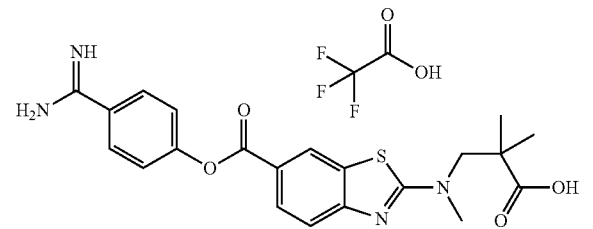

Reaction was carried out from the compound tert-butyl 2-bromobenzo[d]thiazole-6-carboxylate obtained in [Preparation Example 3] in the same manner as in [Example 56] to give the title compound. (Yield: 37%)

1H NMR (400 MHz, TFA salt, DMSO-$d_6$) δ 12.68 (br s, 1H), 9.36 (br s, 2H), 9.24 (br s, 2H), 8.62 (d, J=1.7 Hz, 1H), 8.04 (dd, J=1.8, 8.5 Hz, 1H), 7.92 (d, J=8.6 Hz, 2H), 7.60-7.55 (m, 3H), 3.85 (s, 2H), 3.18 (s, 3H), 1.19 (s, 6H); MS(ESI) m/z: 427 [M+H]$^+$

[Example 87] 4-Carbamimidoyl-2-fluorophenyl (Z)-3-ethyl-2-((3-methoxy-2,2-dimethyl-3-oxopropyl)imino)-2,3-dihydrobenzo[d]thiazole-6-carboxylate

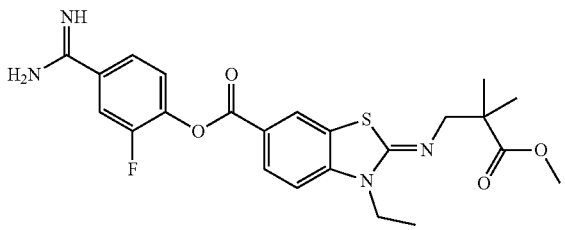

Step 1. Tert-butyl(Z)-3-ethyl-2-((3-methoxy-2,2-dimethyl-3-oxopropyl)imino)-2,3-dihydrobenzo[d]thiazole-6-carboxylate

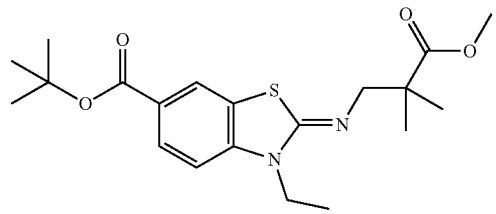

After 4.67 g (12.82 mmol) of the compound tert-butyl 2-((3-methoxy-2,2-dimethyl-3-oxopropyl)amino)benzo[d]thiazole-6-carboxylate obtained in step 2 of [Example 56] was dissolved in 26 mL of dimethylformamide, 8.35 g (25.60 mmol) of cesium carbonate and 1.55 ml (19.23 mmol) of iodoethane were added thereto and then stirred at 90° C. for 16 hours. The reaction mixture was cooled to room temperature, then extracted with ethyl acetate and brine, and the organic layers were combined. The combined organic layers were dried over sodium sulfate, concentrated under reduced pressure and purified by MPLC to give 2.10 g (41%) of the target compound as a pale yellow solid.
MS (ESI) m/z: 393 [M+H]$^+$ Step 2. (Z)-3-ethyl-2-((3-methoxy-2,2-dimethyl-3-oxopropyl)imino)-2,3-dihydrobenzo[d]thiazole-6-carboxylic Acid

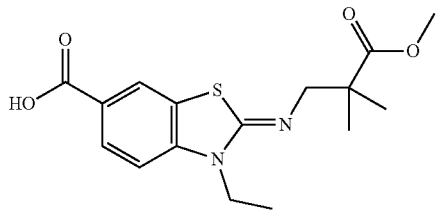

After 2.10 g (5.36 mmol) of the compound tert-butyl(Z)-3-ethyl-2-((3-methoxy-2,2-dimethyl-3-oxopropyl)imino)-2,3-dihydrobenzo[d]thiazole-6-carboxylate obtained in step 1 was dissolved in 25 mL of dichloromethane, 6 ml (78 mmol) of trifluoroacetic acid was added thereto, and then stirred at room temperature for 1 hour. The reaction mixture was concentrated under reduced pressure to give 1.80 g (quant) of the target compound as a yellow liquid without a purification step.

MS (ESI) m/z: 337 [M+H]+

Step 3. 4-Carbamimidoyl-2-fluorophenyl (Z)-3-ethyl-2-((3-methoxy-2,2-dimethyl-3-oxopropyl)imino)-2,3-dihydrobenzo[d]thiazole-6-carboxylate

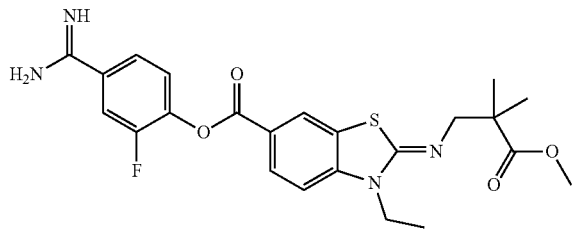

After 1.80 g (5.36 mmol) of the compound (Z)-3-ethyl-2-((3-methoxy-2,2-dimethyl-3-oxopropyl)imino)-2,3-dihydrobenzo[d]thiazole-6-carboxylic acid obtained in step 2 was dissolved in 18 mL of pyridine, 1.12 g (5.89 mmol) of 3-fluoro-4-hydroxybenzimidamide hydrochloride and 1.85 g (9.64 mmol) of EDCI were added thereto, and stirred at 50° C. for 16 hours. The reaction mixture was concentrated under reduced pressure, and purified by prep HPLC to give the target compound as a white solid. The starting material remaining after the reaction was recovered and the above reaction procedure was repeated to give the desired compound in a total yield of 1.28 g (51%).

1H NMR (400 MHz, TFA salt, DMSO-d6) δ 9.42 (br s, 2H), 9.18 (br s, 2H), 8.39 (s, 1H), 8.07 (d, 2H J=8.56 Hz), 7.94 (d, 2H J=10.16 Hz), 7.76 (s, 2H), 7.36 (d, 1H J=8.64 Hz), 4.06-4.01 (m, 2H), 3.58 (s, 3H), 3.21 (s, 2H), 1.21 (s, 6H) 1.12-1.17 (m, 3H); MS(ESI) m/z: 473 [M+H]+

[Example 88] (Z)-3-((6-((4-Carbamimidoyl-2-fluorophenoxy)carbonyl)-3-ethylbenzo[d]thiazole-2(3H)-ylidine)amino)-2,2-dimethylpropanoic Acid

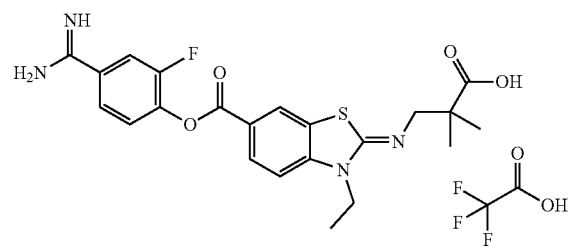

To 1.284 g (2.72 mmol) of the compound 4-carbamimidoyl-2-fluorophenyl (Z)-3-ethyl-2-((3-methoxy-2,2-dimethyl-3-oxopropyl)imino)-2,3-dihydrobenzo[d]thiazole-6-carboxylate obtained in [step 3 of Example 87] was added 4 mL of HCL (4N in H2O) and 4 mL of HCl (4N in dioxane), and the mixture was stirred at room temperature for 4 hours, and then at 70° C. for 1 hour. The reaction mixture was concentrated under reduced pressure and purified by prep HPLC to give 0.66 g (53%) of the target compound as a white solid.

1H NMR (400 MHz, TFA salt, DMSO-d6) δ 12.19 (br s, 1H), 9.43 (br s, 2H), 9.30 (br s, 2H), 8.41 (s, 1H), 8.0 (d, 2H J=6.8 Hz), 7.93 (d, 2H J=10.12 Hz), 7.76 (s, 2H), 7.39 (d, 1H J=8.68 Hz), 4.08-4.06 (m, 2H), 3.22 (s, 2H), 1.19 (s, 6H) 1.18-1.15 (m, 3H); MS(ESI) m/z: 459 [M+H]+

[Experimental Example] Confirmation of Enteropeptidase-Inhibiting Activity of the Compounds According to the Present Invention The following tests were performed to measure the enteropeptidase-inhibiting activity of the compounds according to the present invention.

Enteropeptidase Inhibition Assay

The inhibitory activity of the enteropeptidase inhibitor synthesized using the purified Recombinant Human Enteropeptidase and the substrate Acetyl-Asp-Asp-Asp-Asp-Lys-AFC (BioVision) was measured. 7.2 ng/mL of Enteropeptidase diluted with a buffer (20 mM Tris, 50 mM NaCl, pH 7.5) in a 96 well plate (Costar), 30 μM of Acetyl-Asp-Asp-Asp-Asp-Lys-AFC, several concentrations of Enteropeptidase inhibitors (1% DMSO concentration) were dispensed such that a final volume was 100 μL, and then the enzyme reaction was carried out at 30° C. for 1 hour. At this time, 1% DMSO, a substrate and Enteropeptidase instead of the compound were dispensed onto positive control wells, and 1% DMSO and a substrate were dispensed onto negative control wells. The enzyme reaction was started using an excitation wavelength of 380 nm and an emission wavelength of 500 nm in a fluorescence spectrometer, and then the rate of increase in fluorescence (milli-units per min) between 20 and 60 minutes was measured.

The fluorescence measurement values reduced by the inhibitor diluted at each concentration were converted into relative values % of the positive control group (100% reactivity) and the negative control group (0% reactivity), and used to calculate $IC_{50}$ values. $IC_{50}$ is the concentration of the inhibitor that inhibits the enzyme activity by 50%, and was calculated using PRISM (GraphPad). Ki values were calculated from the $IC_{50}$ values using Cheng-Prusoff equation.

TABLE 1

| Enteropeptidase-inhibiting activity | | | |
|---|---|---|---|
| Example | Enteropeptidase (Ki, nM) | Example | Enteropeptidase (Ki, nM) |
| 1 | 0.68 | 31 | 17 |
| 2 | 4.9 | 32 | 18 |
| 3 | 17.0 | 33 | 8.2 |
| 4 | 0.92 | 34 | 8.9 |
| 5 | 510.0 | 35 | 9.7 |
| 6 | 220.0 | 36 | 9.7 |
| 7 | 0.6 | 37 | 1.8 |
| 8 | 28.0 | 38 | 2.6 |
| 9 | 28.0 | 39 | 2.5 |
| 10 | 11.0 | 40 | 9.7 |
| 11 | 21.0 | 41 | 1.8 |
| 12 | 9.7 | 42 | 1.0 |
| 13 | 4.8 | 43 | 1.7 |
| 14 | 5.1 | 44 | 1.6 |
| 15 | 5.7 | 45 | 1.5 |
| 16 | 19.0 | 46 | 40 |
| 17 | 5.4 | 47 | 0.52 |
| 18 | 8.9 | 48 | 37 |
| 19 | 4.8 | 49 | 0.57 |
| 20 | 2.5 | 50 | 14 |
| 21 | 3.0 | 51 | 9.7 |
| 22 | 0.57 | 52 | 82 |

TABLE 1-continued

Enteropeptidase-inhibiting activity

| Example | Enteropeptidase (Ki, nM) | Example | Enteropeptidase (Ki, nM) |
|---|---|---|---|
| 23 | | 53 | 12 |
| 24 | 8.9 | 54 | 2.5 |
| 25 | 4.7 | 55 | 8.2 |
| 26 | 8.2 | | |
| 27 | 12.0 | | |
| 28 | 6.5 | | |
| 29 | 18.0 | | |
| 30 | 18.0 | | |

(ND: measured but no value detected, blank: not measured)

TABLE 2

Enteropeptidase-inhibiting activity

| Example | Enteropeptidase (Ki, nM) | Example | Enteropeptidase (Ki, nM) |
|---|---|---|---|
| 56 | 0.59 | 76 | 0.57 |
| 57 | 13.0 | 77 | 0.57 |
| 58 | 7.4 | 78 | |
| 59 | 14.0 | 79 | |
| 60 | 10.0 | 80 | 23.0 |
| 61 | 10.0 | 81 | |
| 62 | 4.3 | 82 | 1.9 |
| 63 | 13.0 | 83 | 9.7 |
| 64 | 6.4 | 84 | 2.2 |
| 65 | 5.7 | 85 | 0.55 |
| 66 | 4.8 | 86 | 10.0 |
| 67 | 19.0 | 87 | 4.0 |
| 68 | 06.0 | 88 | 0.16 |
| 69 | 21.0 | | |
| 70 | 3.5 | | |
| 71 | 1.1 | | |
| 72 | 1.3 | | |
| 73 | 0.89 | | |
| 74 | 8.9 | | |
| 75 | 0.7 | | |

(ND: measured but no value detected, blank: not measured)

As can be seen from Tables 1 and 2, it was confirmed that the compounds according to the present invention exhibit TMPRSS15-inhibiting activity.

As such, it was confirmed that the compound of the present invention exhibits excellent enteropeptidase-inhibiting activity. Therefore, the compound of the present invention having enteropeptidase-inhibiting activity reduces the digestive ability of proteins, lipids, and carbohydrates while having fewer side effects such as fat stool, and is effective as a therapeutic or prophylactic drug for various metabolic diseases such as obesity, diabetes mellitus or hyperlipidemia.

The invention claimed is:

1. A compound having the following Chemical Formula 1a or 1b, an optical isomer thereof, or a pharmaceutically acceptable salt thereof:

[Chemical Formula 1a]

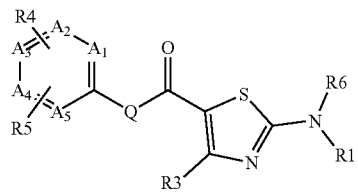

wherein,
A1, A2, A3, A4 and A5 are each independently C;
Q is O or N;
R1 and R6 are each independently H or an unsubstituted or substituted alkyl, or R1 and R6 together with the nitrogen atom to which they are attached form an unsubstituted or substituted 5- to 7-membered heterocyclic ring;
R3 and R4 are each independently H, halo or an unsubstituted or substituted alkyl; and
R5 is amidine or guanidine

[Chemical Formula 1b]

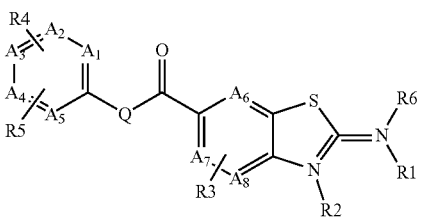

wherein,
A1, A2, A3, A4, A5, A6, A7 and A8 are each independently C;
Q is O or N;
R1 and R6 are each independently H, an unsubstituted or substituted alkyl, or R1 and R6 together with the nitrogen atom to which they are attached form an unsubstituted or substituted 5- to 7-membered heterocyclic ring;
R2 is H or an unsubstituted or substituted alkyl;
R3 and R4 are each independently H, halo or an unsubstituted or substituted alkyl; and
R5 is amidine or guanidine,
the dotted line represents the presence or absence of a bond, and when the bond is present, either a double bond forms between the N in the 5-membered heterocycle and the carbon atom between S and N and the exocyclic nitrogen atom N of NR1R6 becomes an amino group as a substituent for the 5-membered hetero ring and R2 is not present, or a double bond forms between the carbon atom between S and N in the 5-membered heterocycle and the exocyclic nitrogen atom, so that the exocyclic nitrogen atom becomes an imino group and R6 is not present;
wherein the substituent in any of formula 1a and 1b is one to three selected from the group consisting of —(CR$^a_2$)$_n$ R$^b$, —C(O)OR$^a$, —(CH$_2$)$_n$—C(O)OR$^a$, —(CH$_2$)$_n$—C(O)NR$^a$R$^b$, —C(O)NR$^a$R$^b$, and —NR$^a$C(O)R$^b$, where R$^a$ and R$^b$ are each independently hydrogen, halo, —C(O)OR$^c$, C1-C4 alkyl or phenyl, n is an integer from 1 to 4, the C1-C4 alkyl or phenyl is unsubstituted or substituted with one or two —C(O)OR$^c$, or C1-C4 alkoxy, and R$^c$ is hydrogen, C1-C4 alkyl or benzyl.

2. The compound, an optical isomer thereof, or a pharmaceutically acceptable salt thereof according to claim 1, wherein in the Chemical Formula 1a,
R1 and R6 are each independently H or an unsubstituted or substituted C1-C6 alkyl, or R1 and R6 together with the nitrogen atom to which they are attached form an unsubstituted or substituted 5- or 6-membered heterocyclic ring, and
R3 and R4 are each independently H, F, Cl, Br, I, or an unsubstituted or substituted C1-C6 alkyl.

3. The compound, an optical isomer thereof, or a pharmaceutically acceptable salt thereof according to claim 1, wherein in the Chemical Formula 1a,
R1 and R6 are H or C1-C3 alkyl, or R1 and R6 together with the nitrogen atom to which they are attached form pyrrolidinyl or piperidinyl; and
R3 and R4 are H, F or an unsubstituted or substituted C1-C3 alkyl.

4. The compound, an optical isomer thereof, or a pharmaceutically acceptable salt thereof according to claim 1, wherein in the Chemical Formula 1b,
the R1 and R6 are each independently H or an unsubstituted or substituted C1-C3 alkyl, or the R1 and R6 together with the nitrogen atom to which they are attached form piperidinyl;
R2 is H or an unsubstituted or substituted C1-C3 alkyl;
R3 and R4 are each independently H, F, or an unsubstituted or substituted C1-C3 alkyl; and
the substituent is one to three selected from the group consisting of C1-C4 alkyl, —C(O)OR', —C(O)NR'R" or —NR'C(O)R" (where R' and R" are each independently hydrogen, halo, C1-C4 alkyl or phenyl).

5. The compound, an optical isomer thereof, or a pharmaceutically acceptable salt thereof according to claim 1, wherein the compound of the Chemical Formula 1b is a compound represented by the following Chemical Formula 1b-1:

[Chemical Formula 1b-1]

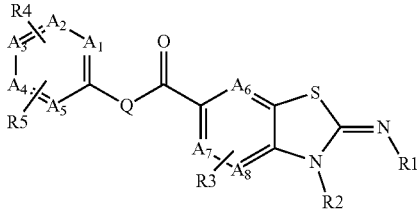

wherein,
A1, A2, A3, A4, A5, A6, A7 and A8 are each independently C;
Q is O or N;
R1 and R2 are each independently H or an unsubstituted or substituted alkyl; and
R3 and R4 are each independently H, halo or an unsubstituted or substituted alkyl.

6. The compound, an optical isomer thereof, or a pharmaceutically acceptable salt thereof according to claim 1, wherein the compound of the Chemical Formula 1b is a compound represented by the following Chemical Formula 1b-2:

[Chemical Formula 1b-2]

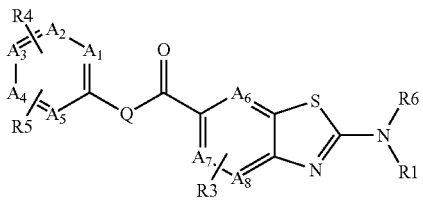

wherein,
A1, A2, A3, A4, A5, A6, A7 and A8 are each independently C or N;
Q is O or N;
R1, and R6 are each independently H or an unsubstituted or substituted alkyl, or R1 and R6 together with the nitrogen atom to which they are attached form an unsubstituted or substituted 5- to 7-membered heterocyclic ring; and
R3 and R4 are each independently H, halo or an unsubstituted or substituted alkyl.

7. The compound, an optical isomer thereof, or a pharmaceutically acceptable salt thereof according to claim 1, which is selected from the group consisting of the following compounds 1] to 88]:
1] 3-((5-((4-carbamimidoyl-2-fluorophenoxy)carbonyl)thiazol-2-yl)(ethyl)amino)propanoic acid;
2] 1-(5-((4-carbamimidoylphenoxy)carbonyl)thiazol-2-yl)piperidine-4-carboxylic acid;
3] 4-carbamimidoylphenyl 2-(4-(methoxycarbonyl)piperidin-1-yl)thiazole-5-carboxylate;
4] 4-carbamimidoyl-2-fluorophenyl 2-(4-(methoxycarbonyl)piperidin-1-yl)thiazole-5-carboxylate;
5] 4-guanidinophenyl 2-(4-(methoxycarbonyl)piperidin-1-yl)thiazole-5-carboxylate;
6] 1-(5-((4-guanidinophenoxy)carbonyl)thiazol-2-yl)piperidine-4-carboxylic acid;
7] 1-(5-((4-carbamimidoyl-2-fluorophenoxy)carbonyl)thiazol-2-yl)piperidine-4-carboxylic acid;
8] 4-carbamimidoylphenyl 2-((3-methoxy-3-oxopropyl)(methyl)amino)thiazole-5-carboxylate;
9] 3-((5-((4-carbamimidoyl)phenoxy)carbonyl)thiazol-2-yl)(methyl)amino)propanoic acid;
10] 4-carbamimidoylphenyl 2-((3-methoxy-3-oxopropyl)amino)thiazole-5-carboxylate;
11] 4-carbamimidoylphenyl 2-((4-methoxy-4-oxobutyl)(methyl)amino)thiazole-5-carboxylate;
12] 4-carbamimidoylphenyl 2-(ethyl(3-methoxy-3-oxopropyl)amino)thiazole-5-carboxylate;
13] 3-((5-((4-carbamimidoyl)phenoxy)carbonyl)thiazol-2-yl)amino)propanoic acid;
14] 3-((5-((4-carbamimidoyl)phenoxy)carbonyl)thiazol-2-yl)(ethyl)amino)propanoic acid;
15] 4-((5-((4-carbamimidoyl)phenoxy)carbonyl)thiazol-2-yl)(methyl)amino)butanoic acid;
16] 4-carbamimidoylphenyl 2-(3-(methoxycarbonyl)pyrrolidin-1-yl)thiazole-5-carboxylate;
17] 1-(5-((4-carbamimidoyl)phenoxy)carbonyl)thiazol-2-yl)pyrrolidine-3-carboxylic acid;
18] 4-carbamimidoylphenyl 2-((3-methoxy-2,2-dimethyl-3-oxopropyl)(methyl) amino)thiazole-5-carboxylate;
19] 3-((5-((4-carbamimidoyl)phenoxy)carbonyl)thiazol-2-yl)(methyl)amino)-2,2-dimethylpropanoic acid;
20] 4-carbamimidoyl-2-fluorophenyl 2-(ethyl(3-methoxy-3-oxopropyl)amino) thiazole-5-carboxylate;
21] 4-carbamimidoyl-2-fluorophenyl 2-((4-methoxy-4-oxobutyl)(methyl)amino)thiazole-5-carboxylate;
22] 4-((5-((4-carbamimidoyl-2-fluorophenoxy)carbonyl)thiazol-2-yl)(methyl)amino)butanoic acid;
23] methyl 1-(5-((4-guanidinophenyl)carbamoyl)thiazol-2-yl)piperidine-4-carboxylate;
24] 4-carbamimidoylphenyl 2-((3-methoxy-2,2-dimethyl-3-oxopropyl)amino)thiazole-5-carboxylate;
25] (1-(5-((4-carbamimidoyl) phenoxy)carbonyl)thiazol-2-yl)piperidine-4-carbonyl)-L-aspartic acid;
26] (1-(5-((4-carbamimidoyl-2-fluorophenoxy)carbonyl)thiazol-2-yl)piperidine-4-carbonyl)-L-aspartate;

27] 4-carbamimidoylphenyl 2-(4-(phenylcarbamoyl)piperidin-1-yl)thiazole-5-carboxylate;
28] 4-carbamimidoylphenyl 2-(4-benzamidopiperidin-1-yl)thiazole-5-carboxylate;
29] 4-carbamimidoylphenyl 2-(4-((2-methoxy-2-oxoethyl)carbamoyl)piperidin-1-yl)thiazole-5-carboxylate;
30] 4-carbamimidoylphenyl 2-(4-((3-methoxy-3-oxopropyl)carbamoyl)piperidin-1-yl)thiazole-5-carboxylate;
31] 4-carbamimidoylphenyl 2-(4-((4-methoxy-4-oxobutyl)(methyl)carbamoyl) piperidin-1-yl)thiazole-5-carboxylate;
32] 4-carbamimidoylphenyl 2-(4-((3-methoxy-2,2-dimethyl-3-oxopropyl)carbamoyl)piperidin-1-yl)thiazole-5-carboxylate;
33] (1-(5-((4-carbamimidoyl)phenoxy)carbonyl)thiazol-2-yl)piperidine-4-carbonyl)glycine;
34] 3-(1-(5-((4-carbamimidoyl)phenoxy)carbonyl)thiazol-2-yl)piperidine-4-carboxamido)propanoic acid;
35] 4-(1-(5-((4-carbamimidoyl)phenoxy)carbonyl)thiazol-2-yl)-N-methylpiperidine-4-carboxamido)butanoic acid;
36] 3-(1-(5-((4-carbamimidoyl)phenoxy)carbonyl)thiazol-2-yl)piperidine-4-carboxamido)-2,2-dimethyl propanoic acid;
37] 4-carbamimidoyl-2-fluorophenyl 2-(4-((2-methoxy-2-oxoethyl)carbamoyl)piperidin-1-yl)thiazole-5-carboxylate;
38] 4-carbamimidoyl-2-fluorophenyl 2-(4-((3-methoxy-3-oxopropyl)carbamoyl)piperidin-1-yl)thiazole-5-carboxylate;
39] 4-carbamimidoyl-2-fluorophenyl 2-(4-((3-methoxy-2,2-dimethyl-3-oxopropyl) carbamoyl)piperidin-1-yl) thiazole-5-carboxylate;
40] 4-carbamimidoylphenyl 2-(4-((4-methoxyphenyl)carbamoyl)piperidin-1-yl)thiazole-5-carboxylate;
41] 4-carbamimidoyl-2-fluorophenyl 2-(4-((4-methoxy-4-oxobutyl)(methyl)carbamoyl) piperidin-1-yl)thiazole-5-carboxylate;
42] (1-(5-((4-carbamimidoyl-2-fluorophenoxy)carbonyl)thiazol-2-yl)piperidine-4-carbonyl)glycine;
43] 3-(1-(5-((4-carbamimidoyl-2-fluorophenoxy)carbonyl)thiazol-2-yl)piperidine-4-carboxamido)propanoic acid;
44] 4-(1-(5-((4-carbamimidoyl-2-fluorophenoxy)carbonyl)thiazol-2-yl)-N-methylpiperidine-4-carboxamido)butanoic acid;
45] 3-(1-(5-((4-carbamimidoyl-2-fluorophenoxy)carbonyl)thiazol-2-yl)piperidine-4-carboxamido)-2, 2-dimethylpropanoic acid;
46] di-tert-butyl(3-((5-((4-carbamimidoyl-2-fluorophenoxy)carbonyl)thiazol-2-yl)(ethyl)amino)propanoyl)-L-aspartate;
47] (3-((5-((4-carbamimidoyl-2-fluorophenoxy)carbonyl)thiazol-2-yl)(ethyl)amino)propanoyl)-L-aspartic acid;
48] di-tert-butyl (3-((5-((4-carbamimidoyl)-2-fluorophenoxy)carbonyl)thiazol-2-yl)(ethyl)amino)propanoyl)-D-glutamate;
49] (3-((5-((4-carbamimidoyl-2-fluorophenoxy)carbonyl)thiazol-2-yl)(ethyl)amino)propanoyl)-D-glutamic acid;
50] 4-carbamimidoyl-2-fluorophenyl 2-(ethyl(3-((4-(methoxycarbonyl)phenyl)amino)-3-oxopropyl)amino)thiazole-5-carboxylate;
51] 4-carbamimidoyl-2-fluorophenyl 2-(ethyl(3-((3-(methoxycarbonyl)phenyl)amino)-3-oxopropyl)amino)thiazole-5-carboxylate;
52] 4-carbamimidoyl-2-fluorophenyl 2-((3-((4-(tert-butoxycarbonyl)phenyl)amino)-3-oxopropyl)(ethyl)amino)thiazole-5-carboxylate;
53] 4-carbamimidoyl-2-fluorophenyl 2-((tert-butoxycarbonyl)phenyl)amino)-3-oxopropyl)(ethyl)amino)thiazole-5-carboxylate;
54] 3-(3-((5-((4-carbamimidoyl-2-fluorophenoxy)carbonyl)thiazol-2-yl)(ethyl)amino)propanamido)benzoic acid;
55] 4-(3-((5-((4-carbamimidoyl-2-fluorophenoxy)carbonyl)thiazol-2-yl)(ethyl)amino)propanamido)benzoic acid;
56] 3-((6-((4-carbamimidoyl-2-fluorophenoxy)carbonyl)benzo[d]thiazol-2-yl)amino)-2,2-dimethylpropanoic acid;
57] 4-carbamimidoylphenyl 2-(4-(methoxycarbonyl)piperidin-1-yl)benzo[d]thiazole-6-carboxylate;
58] 1-(6-((4-carbamimidoylphenoxy)carbonyl)benzo[d]thiazol-2-yl)piperidine-4-carboxylic acid;
59] 4-carbamimidoylphenyl 2-((3-methoxy-3-oxopropyl)amino)benzo[d]thiazole-6-carboxylate;
60] 4-carbamimidoylphenyl 2-((3-methoxy-3-oxopropyl)(methyl)amino)benzo[d]thiazole-6-carboxylate;
61] 4-carbamimidoylphenyl 2-(ethyl(3-methoxy-3-oxopropyl)amino)benzo[d]thiazole-6-carboxylate;
62] 3-((6-((4-carbamimidoylphenoxy)carbonyl)benzo[d]thiazol-2-yl)(methyl)amino)propanoic acid;
63] 4-carbamimidoylphenyl 2-((4-methoxy-4-oxobutyl)(methyl)amino)benzo[d]thiazole-6-carboxylate;
64] 4-((6-((4-carbamimidoylphenoxy)carbonyl)benzo[d]thiazol-2-yl)(methyl)amino)butanoic acid;
65] 3-((6-((4-carbamimidoylphenoxy)carbonyl)benzo[d]thiazol-2-yl)amino)propanoic acid;
66] 3-((6-((4-carbamimidoylphenoxy)carbonyl)benzo[d]thiazol-2-yl)(ethyl)amino)propanoic acid;
67] 4-carbamimidoylphenyl 2-((3-methoxy-2,2-dimethyl-3-oxopropyl)amino)benzo[d]thiazole-6-carboxylate;
68] 4-carbamimidoylphenyl 2-((3-methoxy-2,2-dimethyl-3-oxopropyl)(methyl)amino)benzo[d]thiazole-6-carboxylate;
69] 4-carbamimidoylphenyl 2-(ethyl(3-methoxy-2,2-dimethyl-3-oxopropyl)amino)benzo[d]thiazole-6-carboxylate;
70] 4-carbamimidoyl-2-fluorophenyl 2-(ethyl(3-methoxy-2,2-dimethyl-3-oxopropyl)amino)benzo[d]thiazole-6-carboxylate;
71] 4-carbamimidoyl-2-fluorophenyl 2-((4-methoxy-4-oxobutyl)(methyl)amino)benzo[d]thiazole-6-carboxylate;
72] 4-carbamimidoyl-2-fluorophenyl 2-((3-methoxy-3-oxopropyl)(methyl)amino)benzo[d]thiazole-6-carboxylate;
73] 3-((6-((4-carbamimidoylphenoxy)carbonyl)benzo[d]thiazol-2-yl)amino)-2,2-dimethylpropanoic acid;
74] 3-((6-((4-carbamimidoylphenoxy)carbonyl)benzo[d]thiazol-2-yl)(ethyl) amino)-2,2-dimethylpropanoic acid;
75] 3-((6-((4-carbamimidoyl-2-fluorophenoxy)carbonyl)benzo[d]thiazol-2-yl)(ethyl)amino)-2,2-dimethyl propanoic acid;
76] 4-((6-((4-carbamimidoyl-2-fluorophenoxy)carbonyl)benzo[d]thiazol-2-yl)(methyl)amino)butanoic acid;
77] 3-((6-((4-carbamimidoyl-2-fluorophenoxy)carbonyl)benzo[d]thiazol-2-yl)(methyl) amino)propanoic acid;
78] 4-carbamimidoyl-2-fluorophenyl 2-(4-(methoxycarbonyl piperidin-1-yl)benzo[d]thiazole-6-carboxylate;

79] 1-(6-((4-carbamimidoyl-2-fluorophenoxy)carbonyl)benzo[d]thiazol-2-yl)piperidine-4-carboxylic acid;

80] 4-carbamimidoylphenyl 2-(4-(phenylcarbamoyl)piperidin-1-yl)benzo[d]thiazole-6-carboxylate;

81] 4-carbamimidoyl-2-fluorophenyl 2-(4-(phenylcarbamoyl)piperidin-1-yl)benzo [d]thiazole-6-carboxylate;

82] 4-carbamimidoyl-2-fluorophenyl 2-(4-benzoamidopiperidin-1-yl)benzo[d]thiazole-6-carboxylate;

83] 4-carbamimidoylphenyl 2-(4-benzoamidopiperidin-1-yl)benzo[d]thiazole-6-carboxylate;

84] 4-carbamimidoyl-2-fluorophenyl 2-(ethyl(3-methoxy-3-oxopropyl)amino)benzo[d]thiazole-6-carboxylate;

85] 3-((6-((4-carbamimidoyl-2-fluorophenoxy)carbonyl)benzo[d]thiazol-2-yl)(ethyl)amino)propanoic acid;

86] 3-((6-((4-carbamimidoylphenoxy)carbonyl)benzo[d]thiazol-2-yl)(methyl)amino)-2,2-dimethylpropanoic acid;

87] 4-carbamimidoyl-2-fluorophenyl (Z)-3-ethyl-2-((3-methoxy-2,2-dimethyl-3-oxopropyl)imino)-2,3-dihydrobenzo[d]thiazole-6-carboxylate; and 88] (Z)-3-((6-((4-carbamimidoyl-2-fluorophenoxy)carbonyl)-3-ethylbenzo[d]thiazole-2(3H)-ylidine)amino)-2,2-dimethylpropanoic acid.

8. A pharmaceutical composition for inhibiting enteropeptidase comprising the compound of claim 1, an optical isomer thereof, or a pharmaceutically acceptable salt thereof and a diluent or an excipient.

9. A pharmaceutical composition for the prevention or treatment of metabolic diseases, comprising the compound of claim 1, an optical isomer thereof, or a pharmaceutically acceptable salt thereof and a diluent or an excipient.

10. The pharmaceutical composition for the prevention or treatment of metabolic diseases according to claim 9, wherein the metabolic disease is obesity, diabetes mellitus or hyperlipidemia.

11. The compound, an optical isomer thereof, or a pharmaceutically acceptable salt thereof according to claim 1,
wherein in the Chemical Formulae 1a and 1b,
the R1 and R6 are each independently H or an unsubstituted or substituted C1-C6 alkyl, or together with the nitrogen atom to which they are attached form an unsubstituted or substituted 6-membered heterocyclic ring;
R3 and R4 are each independently H, F, Cl, Br, I, or an unsubstituted or substituted C1-C6 alkyl; and
R5 is amidine, or guanidine; and
wherein in the Chemical Formula 1b, R2 is H or an unsubstituted or substituted C1-C6 alkyl.

* * * * *